US006096320A

United States Patent [19]

[11] Patent Number: 6,096,320
[45] Date of Patent: Aug. 1, 2000

Potter et al.

[54] VACCINES WITH CHIMERIC PROTEIN COMPRISING GAMMA-INTERFERON AND LEUKOTOXIN DERIVED FROM PASTEURELLA HAEMOLYTICA

[75] Inventors: Andrew Potter, Saskatoon, Canada; Manuel Campos, Lincoln, Nebr.; Huw P. A. Hughes, Saskatoon, Canada

[73] Assignees: University of Saskatchewan, Saskatoon; Ciba-Geigy Canada Ltd., Mississauga, both of Canada

[21] Appl. No.: 08/954,418

[22] Filed: Oct. 20, 1997

Related U.S. Application Data

[60] Continuation of application No. 08/681,479, Jul. 22, 1996, abandoned, which is a division of application No. 08/170,126, Dec. 20, 1993, Pat. No. 5,594,107, which is a continuation-in-part of application No. 07/777,715, Oct. 16, 1991, Pat. No. 5,273,889, which is a continuation-in-part of application No. 07/571,301, Aug. 22, 1990, Pat. No. 5,238,823.

[51] Int. Cl.[7] .................... A61K 39/102

[52] U.S. Cl. .................... 424/255.1; 424/192.1; 424/193.1; 424/195.11; 424/85.1; 424/85.4; 424/85.5; 435/69.5; 435/69.7; 530/350; 530/351

[58] Field of Search .................... 424/255.1, 85.1, 424/192.1, 193.1, 195.11, 85.4, 85.5; 435/69.5, 69.7; 530/350, 351

[56] References Cited

U.S. PATENT DOCUMENTS

| | | |
|---|---|---|
| 3,328,252 | 6/1967 | Mora . |
| 4,167,560 | 9/1979 | Wohler, Jr. . |
| 4,171,354 | 10/1979 | Smith . |
| 4,328,210 | 5/1982 | Kucera . |
| 4,346,074 | 8/1982 | Gilmour et al. . |
| 4,366,246 | 12/1982 | Riggs . |
| 4,675,382 | 6/1987 | Murphy . |
| 4,704,362 | 11/1987 | Itakura et al. . |
| 4,818,769 | 4/1989 | Nunberg et al. . |
| 4,933,299 | 6/1990 | Greenfield . |
| 4,935,233 | 6/1990 | Bell et al. . |
| 4,957,739 | 9/1990 | Berget et al. . |
| 5,028,423 | 7/1991 | Prickett . |
| 5,071,761 | 12/1991 | Meyer et al. . |
| 5,095,096 | 3/1992 | Miki et al. . |
| 5,108,910 | 4/1992 | Curtis et al. . |
| 5,114,711 | 5/1992 | Bell et al. . |
| 5,476,657 | 12/1995 | Potter . |

FOREIGN PATENT DOCUMENTS

| | | |
|---|---|---|
| 008622 | 9/1983 | European Pat. Off. . |
| 0230119 | 7/1987 | European Pat. Off. . |
| 0369316 | 5/1990 | European Pat. Off. . |
| 0396387 | 11/1990 | European Pat. Off. . |
| WO 88/00971 | 2/1988 | WIPO . |
| WO 91/01004 | 1/1991 | WIPO . |

OTHER PUBLICATIONS

Cho et al., *Can. J. Vet. Res.* (1986) 50:27–31.

Cho et al., *Can. J. Comp. Med.* (1984) 48:151–155.

Conlon et al., *Infect. Immun.* (1991) 59(2):587–591.

Czarniecki et al., *J. Interferon Res.* (1986) 6:29–37.

Donanche et al., *J. Gen. Microbiol.* (1984) 130:1209–1216.

Gentry et al., *Vet. Immunology and Immunopathology* (1985) 9:239–250.

Highlander et al., *DNA* (1989) 8:15–28.

Himmel et al., *Am. J. Vet. Res.* (1982) 43:764–767.

Lally et al., *Biochem Biophys. Res. Comm.* (1989) 159(1):256–262.

Lawman et al., *Comprehensive Biotech, First Supplement, Animal Biotechnology* (1989) Pergamon Press, London, pp. 63–106.

Lessley et al., *Veterinary Immunology and Immunopathology* (1985) 10:279–296.

Lo et al., *Infect. Immun.* (1985) 50:667–671.

Lorberboum–Galski et al., *Proc. Natl. Acad. Sci. USA* (1988) 85:1922–1926.

Martin et al., *Can. J. Comp. Med.* (1980) 44:1–10.

Shewen et al., *Am. J. Vet. Res.* (1983) 44:715–719.

Shewen et al., *Can. J. Vet. Res.* (1988) 52:30–36.

Strathdee et al., *J. Bacteriol.* (1989) 171(2):916–928.

Strathdee et al., *Infect. Immun.* (1987) 55(12):3233–3236.

R. A. Welch, Pore–forming cytolysins of Gram–negative bacteria, *Molecular Microbiology*, (1991), 5(3):521–528.

Williams et al., *Protein Eng.* (1987) 1(6):493–498.

Yates *Can. J. Comp. Med.* (1982) 46:225–263.

*Primary Examiner*—Christopher L. Chin
*Assistant Examiner*—Jennifer Graser
*Attorney, Agent, or Firm*—Robins & Associates

[57] ABSTRACT

New chimeric proteins, DNA encoding the same, and the use of these proteins in stimulating immunity against respiratory diseases such as pneumonia, including shipping fever pneumonia, are disclosed. The chimeric proteins include at least one epitope of an RTX cytotoxin fused to an active fragment of a cytokine. The chimeric proteins can be used in a vaccine composition. Also disclosed are methods of vaccination as well as methods of making the proteins employed in the vaccines.

13 Claims, 29 Drawing Sheets

```
          10          20          30          40
    *     *     *     *     *     *     *     *     *
ATG GCT ACT GTT AAT AGA TCT GCA CCT ACT TCA AGC TCT ACG GGG AAC
TAC CGA TGA CAA TTA TCT AGA CGT GGA TGA AGT TCG AGA TGC CCC TTG
Met Ala Thr Val Asn Arg Ser Ala Pro Thr Ser Ser Ser Thr Gly Asn>
___a___a___a___a___a____FUSION PROTEIN_a___a___a___a___a___a___>

50          60          70          80          90
 *     *     *     *     *     *     *     *     *     *
ACA ATG AAA GAA GTG AAG TCA TTG CTG CTG GAT TTA CAG TTG CTT TTG
TGT TAC TTT CTT CAC TTC AGT AAC GAC GAC CTA AAT GTC AAC GAA AAC
Thr Met Lys Glu Val Lys Ser Leu Leu Leu Asp Leu Gln Leu Leu Leu>
___a___a___a___a___a____FUSION PROTEIN_a___a___a___a___a___a___>

  100         110         120         130         140
     *     *     *     *     *     *     *     *     *
GAG AAA GTT AAA AAT CCT GAG AAC CTC AAG CTC TCC AGG ATG CAT ACA
CTC TTT CAA TTT TTA GGA CTC TTG GAG TTC GAG AGG TCC TAC GTA TGT
Glu Lys Val Lys Asn Pro Glu Asn Leu Lys Leu Ser Arg Met His Thr>
___a___a___a___a___a____FUSION PROTEIN_a___a___a___a___a___a___>

    150         160         170         180         190
 *     *     *     *     *     *     *     *     *     *
TTT GAC TTT TAC GTG CCC AAG GTT AAC GCT ACA GAA TTG AAA CAT CTT
AAA CTG AAA ATG CAC GGG TTC CAA TTG CGA TGT CTT AAC TTT GTA GAA
Phe Asp Phe Tyr Val Pro Lys Val Asn Ala Thr Glu Leu Lys His Leu>
___a___a___a___a___a____FUSION PROTEIN_a___a___a___a___a___a___>
```

FIG. 3A

```
        200         210          220          230         240
 *       *     *     *     *     *     *      *     *     *
AAG TGT TTA CTA GAA GAA CTC AAA CTT CTA GAG GAA GTG CTA AAT TTA
TTC ACA AAT GAT CTT CTT GAG TTT GAA GAT CTC CTT CAC GAT TTA AAT
Lys Cys Leu Leu Glu Glu Leu Lys Leu Leu Glu Glu Val Leu Asn Leu>
___a___a___a___a___a____FUSION PROTEIN_a___a___a___a___a___a___>

          250         260         270         280
     *     *     *     *     *     *     *     *     *
GCT CCA AGC AAA AAC CTG AAC CCC AGA GAG ATC AAG GAT TCA ATG GAC
CGA GGT TCG TTT TTG GAC TTG GGG TCT CTC TAG TTC CTA AGT TAC CTG
Ala Pro Ser Lys Asn Leu Asn Pro Arg Glu Ile Lys Asp Ser Met Asp>
___a___a___a___a___a____FUSION PROTEIN_a___a___a___a___a___a___>

290         300          310         320         330
 *     *     *     *     *     *     *     *     *     *
AAT ATC AAG AGA ATC GTT TTG GAA CTA CAG GGA TCT GAA ACA AGA TTC
TTA TAG TTC TCT TAG CAA AAC CTT GAT GTC CCT AGA CTT TGT TCT AAG
Asn Ile Lys Arg Ile Val Leu Glu Leu Gln Gly Ser Glu Thr Arg Phe>
___a___a___a___a___a____FUSION PROTEIN_a___a___a___a___a___a___>

  340         350         360          370         380
     *     *     *     *     *     *     *     *     *
ACA TGT GAA TAT GAT GAT GCA ACA GTA AAC GCT GTA GAA TTT CTG AAC
TGT ACA CTT ATA CTA CTA CGT TGT CAT TTG CGA CAT CTT AAA GAC TTG
Thr Cys Glu Tyr Asp Asp Ala Thr Val Asn Ala Val Glu Phe Leu Asn>
___a___a___a___a___a____FUSION PROTEIN_a___a___a___a___a___a___>

    390          400         410          420          430
 *     *     *     *     *     *     *     *     *     *
AAA TGG ATT ACC TTT TGT CAA AGC ATC TAC TCA ACA ATG ACT GGG GAT
TTT ACC TAA TGG AAA ACA GTT TCG TAG ATG AGT TGT TAC TGA CCC CTA
Lys Trp Ile Thr Phe Cys Gln Ser Ile Tyr Ser Thr Met Thr Gly Asp>
___a___a___a___a___a____FUSION PROTEIN_a___a___a___a___a___a___>

       440         450          460          470         480
 *     *     *     *     *     *     *     *     *     *
CTA AGC TTC CCT AGA CTT ACA ACC CTA TCA AAT GGG CTA AAA AAC ACT
GAT TCG AAG GGA TCT GAA TGT TGG GAT AGT TTA CCC GAT TTT TTG TGA
Leu Ser Phe Pro Arg Leu Thr Thr Leu Ser Asn Gly Leu Lys Asn Thr>
___a___a___a___a___a____FUSION PROTEIN_a___a___a___a___a___a___>

          490         500          510          520
     *     *     *     *     *     *     *     *     *
TTA ACG GCA ACC AAA AGT GGC TTA CAT AAA GCC GGT CAA TCA TTA ACC
AAT TGC CGT TGG TTT TCA CCG AAT GTA TTT CGG CCA GTT AGT AAT TGG
Leu Thr Ala Thr Lys Ser Gly Leu His Lys Ala Gly Gln Ser Leu Thr>
___a___a___a___a___a____FUSION PROTEIN_a___a___a___a___a___a___>
```

*FIG. 3B*

```
530        540        550        560        570
 *      *      *      *      *      *      *      *      *      *
CAA GCC GGC AGT TCT TTA AAA ACT GGG GCA AAA AAA ATT ATC CTC TAT
GTT CGG CCG TCA AGA AAT TTT TGA CCC CGT TTT TTT TAA TAG GAG ATA
Gln Ala Gly Ser Ser Leu Lys Thr Gly Ala Lys Lys Ile Ile Leu Tyr>
___a___a___a___a___a____FUSION PROTEIN_a___a___a___a___a___a___>

  580        590        600        610        620
   *      *      *      *      *      *      *      *      *
ATT CCC CAA AAT TAC CAA TAT GAT ACT GAA CAA GGT AAT GGT TTA CAG
TAA GGG GTT TTA ATG GTT ATA CTA TGA CTT GTT CCA TTA CCA AAT GTC
Ile Pro Gln Asn Tyr Gln Tyr Asp Thr Glu Gln Gly Asn Gly Leu Gln>
___a___a___a___a___a____FUSION PROTEIN_a___a___a___a___a___a___>

    630        640        650        660        670
*      *      *      *      *      *      *      *      *      *
GAT TTA GTC AAA GCG GCC GAA GAG TTG GGG ATT GAG GTA CAA AGA GAA
CTA AAT CAG TTT CGC CGG CTT CTC AAC CCC TAA CTC CAT GTT TCT CTT
Asp Leu Val Lys Ala Ala Glu Glu Leu Gly Ile Glu Val Gln Arg Glu>
___a___a___a___a___a____FUSION PROTEIN_a___a___a___a___a___a___>

      680        690        700        710        720
  *      *      *      *      *      *      *      *      *      *
GAA CGC AAT AAT ATT GCA ACA GCT CAA ACC AGT TTA GGC ACG ATT CAA
CTT GCG TTA TTA TAA CGT TGT CGA GTT TGG TCA AAT CCG TGC TAA GTT
Glu Arg Asn Asn Ile Ala Thr Ala Gln Thr Ser Leu Gly Thr Ile Gln>
___a___a___a___a___a____FUSION PROTEIN_a___a___a___a___a___a___>

        730        740        750        760
    *      *      *      *      *      *      *      *      *
ACC GCT ATT GGC TTA ACT GAG CGT GGC ATT GTG TTA TCC GCT CCA CAA
TGG CGA TAA CCG AAT TGA CTC GCA CCG TAA CAC AAT AGG CGA GGT GTT
Thr Ala Ile Gly Leu Thr Glu Arg Gly Ile Val Leu Ser Ala Pro Gln>
___a___a___a___a___a____FUSION PROTEIN_a___a___a___a___a___a___>

770        780        790        800        810
 *      *      *      *      *      *      *      *      *      *
ATT GAT AAA TTG CTA CAG AAA ACT AAA GCA GGC CAA GCA TTA GGT TCT
TAA CTA TTT AAC GAT GTC TTT TGA TTT CGT CCG GTT CGT AAT CCA AGA
Ile Asp Lys Leu Leu Gln Lys Thr Lys Ala Gly Gln Ala Leu Gly Ser>
___a___a___a___a___a____FUSION PROTEIN_a___a___a___a___a___a___>
```

*FIG. 3C*

```
  820         830         840         850         860
    *     *     *     *     *     *     *     *     *
GCC GAA AGC ATT GTA CAA AAT GCA AAT AAA GCC AAA ACT GTA TTA TCT
CGG CTT TCG TAA CAT GTT TTA CGT TTA TTT CGG TTT TGA CAT AAT AGA
Ala Glu Ser Ile Val Gln Asn Ala Asn Lys Ala Lys Thr Val Leu Ser>
___a___a___a___a___a____FUSION PROTEIN_a___a___a___a___a___a___>

    870         880         890         900         910
*     *     *     *     *     *     *     *     *     *
GGC ATT CAA TCT ATT TTA GGC TCA GTA TTG GCT GGA ATG GAT TTA GAT
CCG TAA GTT AGA TAA AAT CCG AGT CAT AAC CGA CCT TAC CTA AAT CTA
Gly Ile Gln Ser Ile Leu Gly Ser Val Leu Ala Gly Met Asp Leu Asp>
___a___a___a___a___a____FUSION PROTEIN_a___a___a___a___a___a___>

       920         930         940         950         960
  *     *     *     *     *     *     *     *     *     *
GAG GCC TTA CAG AAT AAC AGC AAC CAA CAT GCT CTT GCT AAA GCT GGC
CTC CGG AAT GTC TTA TTG TCG TTG GTT GTA CGA GAA CGA TTT CGA CCG
Glu Ala Leu Gln Asn Asn Ser Asn Gln His Ala Leu Ala Lys Ala Gly>
___a___a___a___a___a____FUSION PROTEIN_a___a___a___a___a___a___>

          970         980         990        1000
    *     *     *     *     *     *     *     *     *
TTG GAG CTA ACA AAT TCA TTA ATT GAA AAT ATT GCT AAT TCA GTA AAA
AAC CTC GAT TGT TTA AGT AAT TAA CTT TTA TAA CGA TTA AGT CAT TTT
Leu Glu Leu Thr Asn Ser Leu Ile Glu Asn Ile Ala Asn Ser Val Lys>
___a___a___a___a___a____FUSION PROTEIN_a___a___a___a___a___a___>

1010        1020         1030        1040        1050
  *     *     *     *     *     *     *     *     *     *
ACA CTT GAC GAA TTT GGT GAG CAA ATT AGT CAA TTT GGT TCA AAA CTA
TGT GAA CTG CTT AAA CCA CTC GTT TAA TCA GTT AAA CCA AGT TTT GAT
Thr Leu Asp Glu Phe Gly Glu Gln Ile Ser Gln Phe Gly Ser Lys Leu>
___a___a___a___a___a____FUSION PROTEIN_a___a___a___a___a___a___>

 1060        1070        1080         1090        1100
    *     *     *     *     *     *     *     *     *
CAA AAT ATC AAA GGC TTA GGG ACT TTA GGA GAC AAA CTC AAA AAT ATC
GTT TTA TAG TTT CCG AAT CCC TGA AAT CCT CTG TTT GAG TTT TTA TAG
Gln Asn Ile Lys Gly Leu Gly Thr Leu Gly Asp Lys Leu Lys Asn Ile>
___a___a___a___a___a____FUSION PROTEIN_a___a___a___a___a___a___>

   1110        1120        1130        1140        1150
*     *     *     *     *     *     *     *     *     *
GGT GGA CTT GAT AAA GCT GGC CTT GGT TTA GAT GTT ATC TCA GGG CTA
CCA CCT GAA CTA TTT CGA CCG GAA CCA AAT CTA CAA TAG AGT CCC GAT
Gly Gly Leu Asp Lys Ala Gly Leu Gly Leu Asp Val Ile Ser Gly Leu>
___a___a___a___a___a____FUSION PROTEIN_a___a___a___a___a___a___>
```

FIG. 3D

```
        1160           1170            1180           1190           1200
   *        *        *       *       *       *       *       *       *       *
TTA TCG GGC GCA ACA GCT GCA CTT GTA CTT GCA GAT AAA AAT GCT TCA
AAT AGC CCG CGT TGT CGA CGT GAA CAT GAA CGT CTA TTT TTA CGA AGT
Leu Ser Gly Ala Thr Ala Ala Leu Val Leu Ala Asp Lys Asn Ala Ser>
___a___a___a___a___a____FUSION PROTEIN_a___a___a___a___a___a___>

            1210           1220           1230           1240
       *        *       *        *        *       *       *       *       *
ACA GCT AAA AAA GTG GGT GCG GGT TTT GAA TTG GCA AAC CAA GTT GTT
TGT CGA TTT TTT CAC CCA CGC CCA AAA CTT AAC CGT TTG GTT CAA CAA
Thr Ala Lys Lys Val Gly Ala Gly Phe Glu Leu Ala Asn Gln Val Val>
___a___a___a___a___a____FUSION PROTEIN_a___a___a___a___a___a___>

1250           1260            1270           1280           1290
  *        *       *        *        *       *       *        *       *       *
GGT AAT ATT ACC AAA GCC GTT TCT TCT TAC ATT TTA GCC CAA CGT GTT
CCA TTA TAA TGG TTT CGG CAA AGA AGA ATG TAA AAT CGG GTT GCA CAA
Gly Asn Ile Thr Lys Ala Val Ser Ser Tyr Ile Leu Ala Gln Arg Val>
___a___a___a___a___a____FUSION PROTEIN_a___a___a___a___a___a___>

  1300           1310           1320            1330           1340
     *      *        *       *      *        *      *      *       *
GCA GCA GGT TTA TCT TCA ACT GGG CCT GTG GCT GCT TTA ATT GCT TCT
CGT CGT CCA AAT AGA AGT TGA CCC GGA CAC CGA CGA AAT TAA CGA AGA
Ala Ala Gly Leu Ser Ser Thr Gly Pro Val Ala Ala Leu Ile Ala Ser>
___a___a___a___a___a____FUSION PROTEIN_a___a___a___a___a___a___>

    1350           1360           1370           1380           1390
 *       *       *       *       *       *       *       *       *       *
ACT GTT TCT CTT GCG ATT AGC CCA TTA GCA TTT GCC GGT ATT GCC GAT
TGA CAA AGA GAA CGC TAA TCG GGT AAT CGT AAA CGG CCA TAA CGG CTA
Thr Val Ser Leu Ala Ile Ser Pro Leu Ala Phe Ala Gly Ile Ala Asp>
___a___a___a___a___a____FUSION PROTEIN_a___a___a___a___a___a___>

        1400           1410            1420           1430           1440
   *        *        *       *       *       *       *       *       *       *
AAA TTT AAT CAT GCA AAA AGT TTA GAG AGT TAT GCC GAA CGC TTT AAA
TTT AAA TTA GTA CGT TTT TCA AAT CTC TCA ATA CGG CTT GCG AAA TTT
Lys Phe Asn His Ala Lys Ser Leu Glu Ser Tyr Ala Glu Arg Phe Lys>
___a___a___a___a___a____FUSION PROTEIN_a___a___a___a___a___a___>
```

*FIG. 3E*

```
            1450         1460         1470          1480
        *       *      *       *       *      *       *      *      *
AAA TTA GGC TAT GAC GGA GAT AAT TTA TTA GCA GAA TAT CAG CGG GGA
TTT AAT CCG ATA CTG CCT CTA TTA AAT AAT CGT CTT ATA GTC GCC CCT
Lys Leu Gly Tyr Asp Gly Asp Asn Leu Leu Ala Glu Tyr Gln Arg Gly>
___a___a___a___a___a____FUSION PROTEIN_a___a___a___a___a___a___>

1490          1500         1510         1520         1530
  *       *      *       *       *      *       *      *      *      *
ACA GGG ACT ATT GAT GCA TCG GTT ACT GCA ATT AAT ACC GCA TTG GCC
TGT CCC TGA TAA CTA CGT AGC CAA TGA CGT TAA TTA TGG CGT AAC CGG
Thr Gly Thr Ile Asp Ala Ser Val Thr Ala Ile Asn Thr Ala Leu Ala>
___a___a___a___a___a____FUSION PROTEIN_a___a___a___a___a___a___>

 1540          1550         1560          1570         1580
     *      *       *       *      *       *      *       *      *
GCT ATT GCT GGT GGT GTG TCT GCT GCT GCA GCC GGC TCG GTT ATT GCT
CGA TAA CGA CCA CCA CAC AGA CGA CGA CGT CGG CCG AGC CAA TAA CGA
Ala Ile Ala Gly Gly Val Ser Ala Ala Ala Ala Gly Ser Val Ile Ala>
___a___a___a___a___a____FUSION PROTEIN_a___a___a___a___a___a___>

   1590          1600         1610         1620          1630
*      *       *       *      *       *      *       *      *      *
TCA CCG ATT GCC TTA TTA GTA TCT GGG ATT ACC GGT GTA ATT TCT ACG
AGT GGC TAA CGG AAT AAT CAT AGA CCC TAA TGG CCA CAT TAA AGA TGC
Ser Pro Ile Ala Leu Leu Val Ser Gly Ile Thr Gly Val Ile Ser Thr>
___a___a___a___a___a____FUSION PROTEIN_a___a___a___a___a___a___>

      1640         1650          1660         1670         1680
  *       *       *      *       *      *       *      *      *     *
ATT CTG CAA TAT TCT AAA CAA GCA ATG TTT GAG CAC GTT GCA AAT AAA
TAA GAC GTT ATA AGA TTT GTT CGT TAC AAA CTC GTG CAA CGT TTA TTT
Ile Leu Gln Tyr Ser Lys Gln Ala Met Phe Glu His Val Ala Asn Lys>
___a___a___a___a___a____FUSION PROTEIN_a___a___a___a___a___a___>

            1690         1700         1710          1720
        *       *      *       *       *      *       *      *      *
ATT CAT AAC AAA ATT GTA GAA TGG GAA AAA AAT AAT CAC GGT AAG AAC
TAA GTA TTG TTT TAA CAT CTT ACC CTT TTT TTA TTA GTG CCA TTC TTG
Ile His Asn Lys Ile Val Glu Trp Glu Lys Asn Asn His Gly Lys Asn>
___a___a___a___a___a____FUSION PROTEIN_a___a___a___a___a___a___>

1730          1740         1750         1760         1770
  *       *      *       *       *      *       *      *      *      *
TAC TTT GAA AAT GGT TAC GAT GCC CGT TAT CTT GCG AAT TTA CAA GAT
ATG AAA CTT TTA CCA ATG CTA CGG GCA ATA GAA CGC TTA AAT GTT CTA
Tyr Phe Glu Asn Gly Tyr Asp Ala Arg Tyr Leu Ala Asn Leu Gln Asp>
___a___a___a___a___a____FUSION PROTEIN_a___a___a___a___a___a___>
```

*FIG. 3F*

```
 1780       1790       1800        1810       1820
   *     *     *     *     *     *     *     *     *
AAT ATG AAA TTC TTA CTG AAC TTA AAC AAA GAG TTA CAG GCA GAA CGT
TTA TAC TTT AAG AAT GAC TTG AAT TTG TTT CTC AAT GTC CGT CTT GCA
Asn Met Lys Phe Leu Leu Asn Leu Asn Lys Glu Leu Gln Ala Glu Arg>
___a___a___a___a___a____FUSION PROTEIN_a___a___a___a___a___a___>

   1830       1840       1850       1860       1870
 *     *     *     *     *     *     *     *     *     *
GTC ATC GCT ATT ACT CAG CAG CAA TGG GAT AAC AAC ATT GGT GAT TTA
CAG TAG CGA TAA TGA GTC GTC GTT ACC CTA TTG TTG TAA CCA CTA AAT
Val Ile Ala Ile Thr Gln Gln Gln Trp Asp Asn Asn Ile Gly Asp Leu>
___a___a___a___a___a____FUSION PROTEIN_a___a___a___a___a___a___>

     1880       1890       1900       1910       1920
  *     *     *     *     *     *     *     *     *     *
GCT GGT ATT AGC CGT TTA GGT GAA AAA GTC CTT AGT GGT AAA GCC TAT
CGA CCA TAA TCG GCA AAT CCA CTT TTT CAG GAA TCA CCA TTT CGG ATA
Ala Gly Ile Ser Arg Leu Gly Glu Lys Val Leu Ser Gly Lys Ala Tyr>
___a___a___a___a___a____FUSION PROTEIN_a___a___a___a___a___a___>

        1930       1940       1950       1960
     *     *     *     *     *     *     *     *     *
GTG GAT GCG TTT GAA GAA GGC AAA CAC ATT AAA GCC GAT AAA TTA GTA
CAC CTA CGC AAA CTT CTT CCG TTT GTG TAA TTT CGG CTA TTT AAT CAT
Val Asp Ala Phe Glu Glu Gly Lys His Ile Lys Ala Asp Lys Leu Val>
___a___a___a___a___a____FUSION PROTEIN_a___a___a___a___a___a___>

1970       1980       1990       2000       2010
  *     *     *     *     *     *     *     *     *     *
CAG TTG GAT TCG GCA AAC GGT ATT ATT GAT GTG AGT AAT TCG GGT AAA
GTC AAC CTA AGC CGT TTG CCA TAA TAA CTA CAC TCA TTA AGC CCA TTT
Gln Leu Asp Ser Ala Asn Gly Ile Ile Asp Val Ser Asn Ser Gly Lys>
___a___a___a___a___a____FUSION PROTEIN_a___a___a___a___a___a___>

 2020       2030       2040       2050       2060
    *     *     *     *     *     *     *     *     *
GCG AAA ACT CAG CAT ATC TTA TTC AGA ACG CCA TTA TTG ACG CCG GGA
CGC TTT TGA GTC GTA TAG AAT AAG TCT TGC GGT AAT AAC TGC GGC CCT
Ala Lys Thr Gln His Ile Leu Phe Arg Thr Pro Leu Leu Thr Pro Gly>
___a___a___a___a___a____FUSION PROTEIN_a___a___a___a___a___a___>
```

FIG. 3G

```
    2070           2080          2090          2100          2110
 *      *      *       *      *      *      *      *      *      *
ACA GAG CAT CGT GAA CGC GTA CAA ACA GGT AAA TAT GAA TAT ATT ACC
TGT CTC GTA GCA CTT GCG CAT GTT TGT CCA TTT ATA CTT ATA TAA TGG
Thr Glu His Arg Glu Arg Val Gln Thr Gly Lys Tyr Glu Tyr Ile Thr>
___a___a___a___a___a____FUSION PROTEIN_a___a___a___a___a___a___>

       2120          2130          2140          2150          2160
  *      *       *      *      *      *      *      *      *      *
AAG CTC AAT ATT AAC CGT GTA GAT AGC TGG AAA ATT ACA GAT GGT GCA
TTC GAG TTA TAA TTG GCA CAT CTA TCG ACC TTT TAA TGT CTA CCA CGT
Lys Leu Asn Ile Asn Arg Val Asp Ser Trp Lys Ile Thr Asp Gly Ala>
___a___a___a___a___a____FUSION PROTEIN_a___a___a___a___a___a___>

          2170          2180          2190          2200
     *       *      *      *      *      *      *      *      *
GCA AGT TCT ACC TTT GAT TTA ACT AAC GTT GTT CAG CGT ATT GGT ATT
CGT TCA AGA TGG AAA CTA AAT TGA TTG CAA CAA GTC GCA TAA CCA TAA
Ala Ser Ser Thr Phe Asp Leu Thr Asn Val Val Gln Arg Ile Gly Ile>
___a___a___a___a___a____FUSION PROTEIN_a___a___a___a___a___a___>

2210          2220          2230          2240          2250
  *      *       *      *      *      *      *      *      *      *
GAA TTA GAC AAT GCT GGA AAT GTA ACT AAA ACC AAA GAA ACA AAA ATT
CTT AAT CTG TTA CGA CCT TTA CAT TGA TTT TGG TTT CTT TGT TTT TAA
Glu Leu Asp Asn Ala Gly Asn Val Thr Lys Thr Lys Glu Thr Lys Ile>
___a___a___a___a___a____FUSION PROTEIN_a___a___a___a___a___a___>

 2260          2270          2280          2290          2300
    *      *      *      *      *      *      *      *      *
ATT GCC AAA CTT GGT GAA GGT GAT GAC AAC GTA TTT GTT GGT TCT GGT
TAA CGG TTT GAA CCA CTT CCA CTA CTG TTG CAT AAA CAA CCA AGA CCA
Ile Ala Lys Leu Gly Glu Gly Asp Asp Asn Val Phe Val Gly Ser Gly>
___a___a___a___a___a____FUSION PROTEIN_a___a___a___a___a___a___>

   2310          2320          2330          2340          2350
 *      *      *      *      *      *      *      *      *      *
ACG ACG GAA ATT GAT GGC GGT GAA GGT TAC GAC CGA GTT CAC TAT AGC
TGC TGC CTT TAA CTA CCG CCA CTT CCA ATG CTG GCT CAA GTG ATA TCG
Thr Thr Glu Ile Asp Gly Gly Glu Gly Tyr Asp Arg Val His Tyr Ser>
___a___a___a___a___a____FUSION PROTEIN_a___a___a___a___a___a___>

      2360          2370          2380          2390          2400
  *      *      *      *      *      *      *      *      *      *
CGT GGA AAC TAT GGT GCT TTA ACT ATT GAT GCA ACC AAA GAG ACC GAG
GCA CCT TTG ATA CCA CGA AAT TGA TAA CTA CGT TGG TTT CTC TGG CTC
Arg Gly Asn Tyr Gly Ala Leu Thr Ile Asp Ala Thr Lys Glu Thr Glu>
___a___a___a___a___a____FUSION PROTEIN_a___a___a___a___a___a___>
```

*FIG. 3H*

```
        2410        2420        2430        2440
     *     *     *     *     *     *     *     *     *
CAA GGT AGT TAT ACC GTA AAT CGT TTC GTA GAA ACC GGT AAA GCA CTA
GTT CCA TCA ATA TGG CAT TTA GCA AAG CAT CTT TGG CCA TTT CGT GAT
Gln Gly Ser Tyr Thr Val Asn Arg Phe Val Glu Thr Gly Lys Ala Leu>
___a___a___a___a___a____FUSION PROTEIN_a___a___a___a___a___a___>

2450        2460        2470        2480        2490
  *     *     *     *     *     *     *     *     *     *
CAC GAA GTG ACT TCA ACC CAT ACC GCA TTA GTG GGC AAC CGT GAA GAA
GTG CTT CAC TGA AGT TGG GTA TGG CGT AAT CAC CCG TTG GCA CTT CTT
His Glu Val Thr Ser Thr His Thr Ala Leu Val Gly Asn Arg Glu Glu>
___a___a___a___a___a____FUSION PROTEIN_a___a___a___a___a___a___>

  2500        2510        2520        2530        2540
     *     *     *     *     *     *     *     *     *
AAA ATA GAA TAT CGT CAT AGC AAT AAC CAG CAC CAT GCC GGT TAT TAC
TTT TAT CTT ATA GCA GTA TCG TTA TTG GTC GTG GTA CGG CCA ATA ATG
Lys Ile Glu Tyr Arg His Ser Asn Asn Gln His His Ala Gly Tyr Tyr>
___a___a___a___a___a____FUSION PROTEIN_a___a___a___a___a___a___>

    2550        2560        2570        2580        2590
*     *     *     *     *     *     *     *     *     *
ACC AAA GAT ACC TTG AAA GCT GTT GAA GAA ATT ATC GGT ACA TCA CAT
TGG TTT CTA TGG AAC TTT CGA CAA CTT CTT TAA TAG CCA TGT AGT GTA
Thr Lys Asp Thr Leu Lys Ala Val Glu Glu Ile Ile Gly Thr Ser His>
___a___a___a___a___a____FUSION PROTEIN_a___a___a___a___a___a___>

       2600        2610        2620        2630        2640
  *     *     *     *     *     *     *     *     *     *
AAC GAT ATC TTT AAA GGT AGT AAG TTC AAT GAT GCC TTT AAC GGT GGT
TTG CTA TAG AAA TTT CCA TCA TTC AAG TTA CTA CGG AAA TTG CCA CCA
Asn Asp Ile Phe Lys Gly Ser Lys Phe Asn Asp Ala Phe Asn Gly Gly>
___a___a___a___a___a____FUSION PROTEIN_a___a___a___a___a___a___>

        2650        2660        2670        2680
     *     *     *     *     *     *     *     *     *
GAT GGT GTC GAT ACT ATT GAC GGT AAC GAC GGC AAT GAC CGC TTA TTT
CTA CCA CAG CTA TGA TAA CTG CCA TTG CTG CCG TTA CTG GCG AAT AAA
Asp Gly Val Asp Thr Ile Asp Gly Asn Asp Gly Asn Asp Arg Leu Phe>
___a___a___a___a___a____FUSION PROTEIN_a___a___a___a___a___a___>
```

*FIG. 3I*

```
2690          2700          2710          2720          2730
  *     *     *     *     *     *     *     *     *     *
GGT GGT AAA GGC GAT GAT ATT CTC GAT GGT GGA AAT GGT GAT GAT TTT
CCA CCA TTT CCG CTA CTA TAA GAG CTA CCA CCT TTA CCA CTA CTA AAA
Gly Gly Lys Gly Asp Asp Ile Leu Asp Gly Gly Asn Gly Asp Asp Phe>
___a___a___a___a___a____FUSION PROTEIN_a___a___a___a___a___a___>

  2740          2750          2760          2770          2780
     *     *     *     *     *     *     *     *     *
ATC GAT GGC GGT AAA GGC AAC GAC CTA TTA CAC GGT GGC AAG GGC GAT
TAG CTA CCG CCA TTT CCG TTG CTG GAT AAT GTG CCA CCG TTC CCG CTA
Ile Asp Gly Gly Lys Gly Asn Asp Leu Leu His Gly Gly Lys Gly Asp>
___a___a___a___a___a____FUSION PROTEIN_a___a___a___a___a___a___>

    2790          2800          2810          2820          2830
  *     *     *     *     *     *     *     *     *     *
GAT ATT TTC GTT CAC CGT AAA GGC GAT GGT AAT GAT ATT ATT ACC GAT
CTA TAA AAG CAA GTG GCA TTT CCG CTA CCA TTA CTA TAA TAA TGG CTA
Asp Ile Phe Val His Arg Lys Gly Asp Gly Asn Asp Ile Ile Thr Asp>
___a___a___a___a___a____FUSION PROTEIN_a___a___a___a___a___a___>

       2840          2850          2860          2870          2880
   *     *     *     *     *     *     *     *     *     *
TCT GAC GGC AAT GAT AAA TTA TCA TTC TCT GAT TCG AAC TTA AAA GAT
AGA CTG CCG TTA CTA TTT AAT AGT AAG AGA CTA AGC TTG AAT TTT CTA
Ser Asp Gly Asn Asp Lys Leu Ser Phe Ser Asp Ser Asn Leu Lys Asp>
___a___a___a___a___a____FUSION PROTEIN_a___a___a___a___a___a___>

          2890          2900          2910          2920
     *     *     *     *     *     *     *     *     *
TTA ACA TTT GAA AAA GTT AAA CAT AAT CTT GTC ATC ACG AAT AGC AAA
AAT TGT AAA CTT TTT CAA TTT GTA TTA GAA CAG TAG TGC TTA TCG TTT
Leu Thr Phe Glu Lys Val Lys His Asn Leu Val Ile Thr Asn Ser Lys>
___a___a___a___a___a____FUSION PROTEIN_a___a___a___a___a___a___>

2930          2940          2950          2960          2970
  *     *     *     *     *     *     *     *     *     *
AAA GAG AAA GTG ACC ATT CAA AAC TGG TTC CGA GAG GCT GAT TTT GCT
TTT CTC TTT CAC TGG TAA GTT TTG ACC AAG GCT CTC CGA CTA AAA CGA
Lys Glu Lys Val Thr Ile Gln Asn Trp Phe Arg Glu Ala Asp Phe Ala>
___a___a___a___a___a____FUSION PROTEIN_a___a___a___a___a___a___>

  2980          2990          3000          3010          3020
     *     *     *     *     *     *     *     *     *
AAA GAA GTG CCT AAT TAT AAA GCA ACT AAA GAT GAG AAA ATC GAA GAA
TTT CTT CAC GGA TTA ATA TTT CGT TGA TTT CTA CTC TTT TAG CTT CTT
Lys Glu Val Pro Asn Tyr Lys Ala Thr Lys Asp Glu Lys Ile Glu Glu>
___a___a___a___a___a____FUSION PROTEIN_a___a___a___a___a___a___>
```

*FIG. 3J*

```
     3030          3040         3050         3060         3070
 *     *     *      *     *      *     *      *     *      *
ATC ATC GGT CAA AAT GGC GAG CGG ATC ACC TCA AAG CAA GTT GAT GAT
TAG TAG CCA GTT TTA CCG CTC GCC TAG TGG AGT TTC GTT CAA CTA CTA
Ile Ile Gly Gln Asn Gly Glu Arg Ile Thr Ser Lys Gln Val Asp Asp>
___a___a___a___a___a____FUSION PROTEIN_a___a___a___a___a___a___>

       3080          3090          3100         3110        3120
   *     *      *     *      *      *     *      *     *     *
CTT ATC GCA AAA GGT AAC GGC AAA ATT ACC CAA GAT GAG CTA TCA AAA
GAA TAG CGT TTT CCA TTG CCG TTT TAA TGG GTT CTA CTC GAT AGT TTT
Leu Ile Ala Lys Gly Asn Gly Lys Ile Thr Gln Asp Glu Leu Ser Lys>
___a___a___a___a___a____FUSION PROTEIN_a___a___a___a___a___a___>

           3130         3140         3150         3160
       *     *     *      *     *     *     *     *     *
GTT GTT GAT AAC TAT GAA TTG CTC AAA CAT AGC AAA AAT GTG ACA AAC
CAA CAA CTA TTG ATA CTT AAC GAG TTT GTA TCG TTT TTA CAC TGT TTG
Val Val Asp Asn Tyr Glu Leu Leu Lys His Ser Lys Asn Val Thr Asn>
___a___a___a___a___a____FUSION PROTEIN_a___a___a___a___a___a___>

3170          3180         3190         3200         3210
  *      *     *      *     *     *      *     *     *     *
AGC TTA GAT AAG TTA ATC TCA TCT GTA AGT GCA TTT ACC TCG TCT AAT
TCG AAT CTA TTC AAT TAG AGT AGA CAT TCA CGT AAA TGG AGC AGA TTA
Ser Leu Asp Lys Leu Ile Ser Ser Val Ser Ala Phe Thr Ser Ser Asn>
___a___a___a___a___a____FUSION PROTEIN_a___a___a___a___a___a___>

 3220          3230         3240          3250         3260
    *     *     *      *     *     *      *     *     *
GAT TCG AGA AAT GTA TTA GTG GCT CCA ACT TCA ATG TTG GAT CAA AGT
CTA AGC TCT TTA CAT AAT CAC CGA GGT TGA AGT TAC AAC CTA GTT TCA
Asp Ser Arg Asn Val Leu Val Ala Pro Thr Ser Met Leu Asp Gln Ser>
___a___a___a___a___a____FUSION PROTEIN_a___a___a___a___a___a___>

   3270          3280         3290         3300       3310
 *     *     *     *     *      *      *     *    *    *
TTA TCT TCT CTT CAA TTT GCT AGG GGA TCC TAG CTAGCTAGCCATGG
AAT AGA AGA GAA GTT AAA CGA TCC CCT AGG ATC GATCGATCGGTACC
Leu Ser Ser Leu Gln Phe Ala Arg Gly Ser End>
___a___a___a__FUSION PROTEIN___a___a___a___>
```

FIG. 3K

```
            10          20          30          40
    *       *     *     *     *     *     *     *     *
ATG GCT ACT GTT ATA GAT CTA AGC TTC CCA AAA ACT GGG GCA AAA AAA
TAC CGA TGA CAA TAT CTA GAT TCG AAG GGT TTT TGA CCC CGT TTT TTT
Met Ala Thr Val Ile Asp Leu Ser Phe Pro Lys Thr Gly Ala Lys Lys>
___c___c___RECOMBINANT LEUKOTOXIN PEPTIDE [SPLIT]_c___c___c___>
___d___d___10_d___d___d20__PAA352_d_30d___d___d___40_d___d___>
___a___a___VECTOR SEQUENCE_a___a___a__>

50          60          70          80          90
 *     *     *     *     *     *     *     *     *     *
ATT ATC CTC TAT ATT CCC CAA AAT TAC CAA TAT GAT ACT GAA CAA GGT
TAA TAG GAG ATA TAA GGG GTT TTA ATG GTT ATA CTA TGA CTT GTT CCA
Ile Ile Leu Tyr Ile Pro Gln Asn Tyr Gln Tyr Asp Thr Glu Gln Gly>
___c___c___RECOMBINANT LEUKOTOXIN PEPTIDE [SPLIT]_c___c___c___>
50_d___d___d_60d___d___d____PAA352_d___d80_d___d___d_90d___d___>

  100         110         120         130         140
    *     *     *     *     *     *     *     *     *
AAT GGT TTA CAG GAT TTA GTC AAA GCG GCC GAA GAG TTG GGG ATT GAG
TTA CCA AAT GTC CTA AAT CAG TTT CGC CGG CTT CTC AAC CCC TAA CTC
Asn Gly Leu Gln Asp Leu Val Lys Ala Ala Glu Glu Leu Gly Ile Glu>
___c___c___RECOMBINANT LEUKOTOXIN PEPTIDE [SPLIT]_c___c___c___>
___100__d___d___110_d___d____PAA352_d___d__130__d___d___140_d___>

   150         160         170         180         190
*     *     *     *     *     *     *     *     *     *
GTA CAA AGA GAA GAA CGC AAT AAT ATT GCA ACA GCT CAA ACC AGT TTA
CAT GTT TCT CTT CTT GCG TTA TTA TAA CGT TGT CGA GTT TGG TCA AAT
Val Gln Arg Glu Glu Arg Asn Asn Ile Ala Thr Ala Gln Thr Ser Leu>
___c___c___RECOMBINANT LEUKOTOXIN PEPTIDE [SPLIT]_c___c___c___>
___d150d___d___d__160__d____PAA352_d___d___d180d___d___d__190__>
```

*FIG. 7A*

```
         200        210        220        230        240
   *     *     *    *     *    *    *     *     *     *
GGC ACG ATT CAA ACC GCT ATT GGC TTA ACT GAG CGT GGC ATT GTG TTA
CCG TGC TAA GTT TGG CGA TAA CCG AAT TGA CTC GCA CCG TAA CAC AAT
Gly Thr Ile Gln Thr Ala Ile Gly Leu Thr Glu Arg Gly Ile Val Leu>
___c___c____RECOMBINANT LEUKOTOXIN PEPTIDE [SPLIT]_c___c___c___>
___d___200_d___d___d210d____PAA352_20__d___d___230_d___d___d240>

            250        260        270        280
       *     *     *    *     *    *     *     *     *
TCC GCT CCA CAA ATT GAT AAA TTG CTA CAG AAA ACT AAA GCA GGC CAA
AGG CGA GGT GTT TAA CTA TTT AAC GAT GTC TTT TGA TTT CGT CCG GTT
Ser Ala Pro Gln Ile Asp Lys Leu Leu Gln Lys Thr Lys Ala Gly Gln>
___c___c____RECOMBINANT LEUKOTOXIN PEPTIDE [SPLIT]_c___c___c___>
___d___d__250__d___d___260__PAA352_d270d___d___d__280__d___d___>

290          300        310        320        330
 *     *     *    *     *    *     *     *     *     *
GCA TTA GGT TCT GCC GAA AGC ATT GTA CAA AAT GCA AAT AAA GCC AAA
CGT AAT CCA AGA CGG CTT TCG TAA CAT GTT TTA CGT TTA TTT CGG TTT
Ala Leu Gly Ser Ala Glu Ser Ile Val Gln Asn Ala Asn Lys Ala Lys>
___c___c____RECOMBINANT LEUKOTOXIN PEPTIDE [SPLIT]_c___c___c___>
290_d___d___d300d___d___d___PAA352__d___320_d___d___d330d___d___>

  340          350        360        370        380
    *     *     *    *     *    *     *     *     *
ACT GTA TTA TCT GGC ATT CAA TCT ATT TTA GGC TCA GTA TTG GCT GGA
TGA CAT AAT AGA CCG TAA GTT AGA TAA AAT CCG AGT CAT AAC CGA CCT
Thr Val Leu Ser Gly Ile Gln Ser Ile Leu Gly Ser Val Leu Ala Gly>
___c___c____RECOMBINANT LEUKOTOXIN PEPTIDE [SPLIT]_c___c___c___>
__340__d___d___350_d___d____PAA352_d___d__370__d___d___380_d___>

     390        400        410        420        430
 *     *     *    *     *    *     *     *     *     *
ATG GAT TTA GAT GAG GCC TTA CAG AAT AAC AGC AAC CAA CAT GCT CTT
TAC CTA AAT CTA CTC CGG AAT GTC TTA TTG TCG TTG GTT GTA CGA GAA
Met Asp Leu Asp Glu Ala Leu Gln Asn Asn Ser Asn Gln His Ala Leu>
___c___c____RECOMBINANT LEUKOTOXIN PEPTIDE [SPLIT]_c___c___c___>
___d390d___d___d__400__d____PAA352_d___d___d420d___d___d__430__>

          440        450        460        470        480
   *     *     *    *     *    *     *     *     *     *
GCT AAA GCT GGC TTG GAG CTA ACA AAT TCA TTA ATT GAA AAT ATT GCT
CGA TTT CGA CCG AAC CTC GAT TGT TTA AGT AAT TAA CTT TTA TAA CGA
Ala Lys Ala Gly Leu Glu Leu Thr Asn Ser Leu Ile Glu Asn Ile Ala>
___c___c____RECOMBINANT LEUKOTOXIN PEPTIDE [SPLIT]_c___c___c___>
___d___440_d___d___d450d____PAA352_60__d___d___470_d___d___d480>
```

*FIG. 7B*

```
                490         500         510         520
          *     *     *     *     *     *     *     *     *
AAT TCA GTA AAA ACA CTT GAC GAA TTT GGT GAG CAA ATT AGT CAA TTT
TTA AGT CAT TTT TGT GAA CTG CTT AAA CCA CTC GTT TAA TCA GTT AAA
Asn Ser Val Lys Thr Leu Asp Glu Phe Gly Glu Gln Ile Ser Gln Phe>
___c___c____RECOMBINANT LEUKOTOXIN PEPTIDE [SPLIT]_c___c___c___>
___d___d__490__d___d___500__PAA352_d510d___d___d__520__d___d___>

530         540         550         560         570
 *     *     *     *     *     *     *     *     *     *
GGT TCA AAA CTA CAA AAT ATC AAA GGC TTA GGG ACT TTA GGA GAC AAA
CCA AGT TTT GAT GTT TTA TAG TTT CCG AAT CCC TGA AAT CCT CTG TTT
Gly Ser Lys Leu Gln Asn Ile Lys Gly Leu Gly Thr Leu Gly Asp Lys>
___c___c____RECOMBINANT LEUKOTOXIN PEPTIDE [SPLIT]_c___c___c___>
530_d___d___d540d___d___d___PAA352__d___560_d___d___d570d___d___>

  580         590         600         610         620
   *     *     *     *     *     *     *     *     *
CTC AAA AAT ATC GGT GGA CTT GAT AAA GCT GGC CTT GGT TTA GAT GTT
GAG TTT TTA TAG CCA CCT GAA CTA TTT CGA CCG GAA CCA AAT CTA CAA
Leu Lys Asn Ile Gly Gly Leu Asp Lys Ala Gly Leu Gly Leu Asp Val>
___c___c____RECOMBINANT LEUKOTOXIN PEPTIDE [SPLIT]_c___c___c___>
__580__d___d___590_d___d____PAA352_d___d__610__d___d___620_d___>

    630         640         650         660         670
*     *     *     *     *     *     *     *     *     *
ATC TCA GGG CTA TTA TCG GGC GCA ACA GCT GCA CTT GTA CTT GCA GAT
TAG AGT CCC GAT AAT AGC CCG CGT TGT CGA CGT GAA CAT GAA CGT CTA
Ile Ser Gly Leu Leu Ser Gly Ala Thr Ala Ala Leu Val Leu Ala Asp>
___c___c____RECOMBINANT LEUKOTOXIN PEPTIDE [SPLIT]_c___c___c___>
___d630d___d___d__640_d____PAA352_d___d___d660d___d___d__670__>

        680         690         700         710         720
  *     *     *     *     *     *     *     *     *     *
AAA AAT GCT TCA ACA GCT AAA AAA GTG GGT GCG GGT TTT GAA TTG GCA
TTT TTA CGA AGT TGT CGA TTT TTT CAC CCA CGC CCA AAA CTT AAC CGT
Lys Asn Ala Ser Thr Ala Lys Lys Val Gly Ala Gly Phe Glu Leu Ala>
___c___c____RECOMBINANT LEUKOTOXIN PEPTIDE [SPLIT]_c___c___c___>
___d___680_d___d___d690d____PAA352_00__d___d___710_d___d___d720>

                730         740         750         760
          *     *     *     *     *     *     *     *     *
AAC CAA GTT GTT GGT AAT ATT ACC AAA GCC GTT TCT TCT TAC ATT TTA
TTG GTT CAA CAA CCA TTA TAA TGG TTT CGG CAA AGA AGA ATG TAA AAT
Asn Gln Val Val Gly Asn Ile Thr Lys Ala Val Ser Ser Tyr Ile Leu>
___c___c____RECOMBINANT LEUKOTOXIN PEPTIDE [SPLIT]_c___c___c___>
___d___d__730__d___d___740__PAA352_d750d___d___d__760__d___d___>
```

*FIG. 7C*

```
770         780         790         800         810
 *     *     *     *     *     *     *     *     *     *
GCC CAA CGT GTT GCA GCA GGT TTA TCT TCA ACT GGG CCT GTG GCT GCT
CGG GTT GCA CAA CGT CGT CCA AAT AGA AGT TGA CCC GGA CAC CGA CGA
Ala Gln Arg Val Ala Ala Gly Leu Ser Ser Thr Gly Pro Val Ala Ala>
___c___c___RECOMBINANT LEUKOTOXIN PEPTIDE [SPLIT]_c___c___c___>
770_d___d___d780d___d___d___PAA352__d___800_d___d___d810d___d___>

  820         830         840         850         860
   *     *     *     *     *     *     *     *     *
TTA ATT GCT TCT ACT GTT TCT CTT GCG ATT AGC CCA TTA GCA TTT GCC
AAT TAA CGA AGA TGA CAA AGA GAA CGC TAA TCG GGT AAT CGT AAA CGG
Leu Ile Ala Ser Thr Val Ser Leu Ala Ile Ser Pro Leu Ala Phe Ala>
___c___c___RECOMBINANT LEUKOTOXIN PEPTIDE [SPLIT]_c___c___c___>
__820__d___d___830_d___d____PAA352_d___d__850__d___d___860_d___>

    870         880         890         900         910
 *     *     *     *     *     *     *     *     *     *
GGT ATT GCC GAT AAA TTT AAT CAT GCA AAA AGT TTA GAG AGT TAT GCC
CCA TAA CGG CTA TTT AAA TTA GTA CGT TTT TCA AAT CTC TCA ATA CGG
Gly Ile Ala Asp Lys Phe Asn His Ala Lys Ser Leu Glu Ser Tyr Ala>
___c___c___RECOMBINANT LEUKOTOXIN PEPTIDE [SPLIT]_c___c___c___>
___d870d___d___d__880__d____PAA352_d___d___d900d___d___d__910__>

       920         930         940         950         960
 *     *     *     *     *     *     *     *     *     *
GAA CGC TTT AAA AAA TTA GGC TAT GAC GGA GAT AAT TTA TTA GCA GAA
CTT GCG AAA TTT TTT AAT CCG ATA CTG CCT CTA TTA AAT AAT CGT CTT
Glu Arg Phe Lys Lys Leu Gly Tyr Asp Gly Asp Asn Leu Leu Ala Glu>
___c___c___RECOMBINANT LEUKOTOXIN PEPTIDE [SPLIT]_c___c___c___>
___d___920_d___d___d930d____PAA352_40__d___d___950_d___d___d960>

         970         980         990         1000
    *     *     *     *     *     *     *     *     *
TAT CAG CGG GGA ACA GGG ACT ATT GAT GCA TCG GTT ACT GCA ATT AAT
ATA GTC GCC CCT TGT CCC TGA TAA CTA CGT AGC CAA TGA CGT TAA TTA
Tyr Gln Arg Gly Thr Gly Thr Ile Asp Ala Ser Val Thr Ala Ile Asn>
___c___c___RECOMBINANT LEUKOTOXIN PEPTIDE [SPLIT]_c___c___c___>
___d___d_970__d___d___980__PAA352_d990d___d___d_1000__d___d___>

1010        1020        1030        1040        1050
 *     *     *     *     *     *     *     *     *     *
ACC GCA TTG GCC GCT ATT GCT GGT GGT GTG TCT GCT GCT GCA GCC GGC
TGG CGT AAC CGG CGA TAA CGA CCA CCA CAC AGA CGA CGA CGT CGG CCG
Thr Ala Leu Ala Ala Ile Ala Gly Gly Val Ser Ala Ala Ala Ala Gly>
___c___c___RECOMBINANT LEUKOTOXIN PEPTIDE [SPLIT]_c___c___c___>
1010_d___d___1020d___d___d_1_PAA352__d__1040_d___d___1050d___d___>
```

FIG. 7D

```
 1060        1070        1080        1090        1100
   *     *     *     *     *     *     *     *     *
TCG GTT ATT GCT TCA CCG ATT GCC TTA TTA GTA TCT GGG ATT ACC GGT
AGC CAA TAA CGA AGT GGC TAA CGG AAT AAT CAT AGA CCC TAA TGG CCA
Ser Val Ile Ala Ser Pro Ile Ala Leu Leu Val Ser Gly Ile Thr Gly>
___c___c___RECOMBINANT LEUKOTOXIN PEPTIDE [SPLIT]_c___c___c___>
_1060__d___d__1070_d___d____PAA352_d___d_1090__d___d__1100_d___>

   1110        1120        1130        1140        1150
*     *     *     *     *     *     *     *     *     *
GTA ATT TCT ACG ATT CTG CAA TAT TCT AAA CAA GCA ATG TTT GAG CAC
CAT TAA AGA TGC TAA GAC GTT ATA AGA TTT GTT CGT TAC AAA CTC GTG
Val Ile Ser Thr Ile Leu Gln Tyr Ser Lys Gln Ala Met Phe Glu His>
___c___c___RECOMBINANT LEUKOTOXIN PEPTIDE [SPLIT]_c___c___c___>
___1110d___d___d_1120__d____PAA352_d___d___1140d___d___d_1150__>

      1160        1170        1180        1190        1200
  *     *     *     *     *     *     *     *     *     *
GTT GCA AAT AAA ATT CAT AAC AAA ATT GTA GAA TGG GAA AAA AAT AAT
CAA CGT TTA TTT TAA GTA TTG TTT TAA CAT CTT ACC CTT TTT TTA TTA
Val Ala Asn Lys Ile His Asn Lys Ile Val Glu Trp Glu Lys Asn Asn>
___c___c___RECOMBINANT LEUKOTOXIN PEPTIDE [SPLIT]_c___c___c___>
___d__1160_d___d___1170d____PAA352_80__d___d__1190_d___d___1200>

         1210        1220        1230        1240
     *     *     *     *     *     *     *     *     *
CAC GGT AAG AAC TAC TTT GAA AAT GGT TAC GAT GCC CGT TAT CTT GCG
GTG CCA TTC TTG ATG AAA CTT TTA CCA ATG CTA CGG GCA ATA GAA CGC
His Gly Lys Asn Tyr Phe Glu Asn Gly Tyr Asp Ala Arg Tyr Leu Ala>
___c___c___RECOMBINANT LEUKOTOXIN PEPTIDE [SPLIT]_c___c___c___>
___d___d_1210__d___d___1220__PAA352_1230d___d___d_1240__d___d___>

1250        1260        1270        1280        1290
   *     *     *     *     *     *     *     *     *     *
AAT TTA CAA GAT AAT ATG AAA TTC TTA CTG AAC TTA AAC AAA GAG TTA
TTA AAT GTT CTA TTA TAC TTT AAG AAT GAC TTG AAT TTG TTT CTC AAT
Asn Leu Gln Asp Asn Met Lys Phe Leu Leu Asn Leu Asn Lys Glu Leu>
___c___c___RECOMBINANT LEUKOTOXIN PEPTIDE [SPLIT]_c___c___c___>
1250_d___d___1260d___d___d_1_PAA352__d__1280_d___d___1290d___d___>

 1300        1310        1320        1330        1340
   *     *     *     *     *     *     *     *     *
CAG GCA GAA CGT GTC ATC GCT ATT ACT CAG CAG CAA TGG GAT AAC AAC
GTC CGT CTT GCA CAG TAG CGA TAA TGA GTC GTC GTT ACC CTA TTG TTG
Gln Ala Glu Arg Val Ile Ala Ile Thr Gln Gln Gln Trp Asp Asn Asn>
___c___c___RECOMBINANT LEUKOTOXIN PEPTIDE [SPLIT]_c___c___c___>
_1300__d___d__1310_d___d____PAA352_d___d_1330__d___d__1340_d___>
```

*FIG. 7E*

```
  1350          1360        1370        1380         1390
 *     *      *     *     *     *     *     *     *     *
ATT GGT GAT TTA GCT GGT ATT AGC CGT TTA GGT GAA AAA GTC CTT AGT
TAA CCA CTA AAT CGA CCA TAA TCG GCA AAT CCA CTT TTT CAG GAA TCA
Ile Gly Asp Leu Ala Gly Ile Ser Arg Leu Gly Glu Lys Val Leu Ser>
___c___c____RECOMBINANT LEUKOTOXIN PEPTIDE [SPLIT]_c___c___c___>
___1350d___d___d_1360__d____PAA352_d___d___1380d___d___d_1390__>

     1400        1410        1420        1430        1440
  *     *     *     *     *     *     *     *     *     *
GGT AAA GCC TAT GTG GAT GCG TTT GAA GAA GGC AAA CAC ATT AAA GCC
CCA TTT CGG ATA CAC CTA CGC AAA CTT CTT CCG TTT GTG TAA TTT CGG
Gly Lys Ala Tyr Val Asp Ala Phe Glu Glu Gly Lys His Ile Lys Ala>
___c___c____RECOMBINANT LEUKOTOXIN PEPTIDE [SPLIT]_c___c___c___>
___d__1400_d___d___1410d____PAA352_20__d___d__1430_d___d___1440>

        1450        1460        1470        1480
     *     *     *     *     *     *     *     *     *
GAT AAA TTA GTA CAG TTG GAT TCG GCA AAC GGT ATT ATT GAT GTG AGT
CTA TTT AAT CAT GTC AAC CTA AGC CGT TTG CCA TAA TAA CTA CAC TCA
Asp Lys Leu Val Gln Leu Asp Ser Ala Asn Gly Ile Ile Asp Val Ser>
___c___c____RECOMBINANT LEUKOTOXIN PEPTIDE [SPLIT]_c___c___c___>
___d___d_1450__d___d__1460__PAA352_1470d___d___d_1480__d___d___>

1490        1500        1510        1520        1530
  *     *     *     *     *     *     *     *     *     *
AAT TCG GGT AAA GCG AAA ACT CAG CAT ATC TTA TTC AGA ACG CCA TTA
TTA AGC CCA TTT CGC TTT TGA GTC GTA TAG AAT AAG TCT TGC GGT AAT
Asn Ser Gly Lys Ala Lys Thr Gln His Ile Leu Phe Arg Thr Pro Leu>
___c___c____RECOMBINANT LEUKOTOXIN PEPTIDE [SPLIT]_c___c___c___>
1490_d___d___1500d___d___d_1_PAA352__d__1520_d___d___1530d___d___>

 1540       1550        1560        1570        1580
     *     *     *     *     *     *     *     *     *
TTG ACG CCG GGA ACA GAG CAT CGT GAA CGC GTA CAA ACA GGT AAA TAT
AAC TGC GGC CCT TGT CTC GTA GCA CTT GCG CAT GTT TGT CCA TTT ATA
Leu Thr Pro Gly Thr Glu His Arg Glu Arg Val Gln Thr Gly Lys Tyr>
___c___c____RECOMBINANT LEUKOTOXIN PEPTIDE [SPLIT]_c___c___c___>
_1540__d___d__1550_d___d____PAA352_d___d_1570__d___d__1580_d___>

    1590        1600        1610        1620        1630
 *     *     *     *     *     *     *     *     *     *
GAA TAT ATT ACC AAG CTC AAT ATT AAC CGT GTA GAT AGC TGG AAA ATT
CTT ATA TAA TGG TTC GAG TTA TAA TTG GCA CAT CTA TCG ACC TTT TAA
Glu Tyr Ile Thr Lys Leu Asn Ile Asn Arg Val Asp Ser Trp Lys Ile>
___c___c____RECOMBINANT LEUKOTOXIN PEPTIDE [SPLIT]_c___c___c___>
___1590d___d___d_1600__d____PAA352_d___d___1620d___d___d_1630__>
```

*FIG. 7F*

```
        1640          1650           1660          1670          1680
   *      *      *      *      *      *      *      *      *      *
ACA GAT GGT GCA GCA AGT TCT ACC TTT GAT TTA ACT AAC GTT GTT CAG
TGT CTA CCA CGT CGT TCA AGA TGG AAA CTA AAT TGA TTG CAA CAA GTC
Thr Asp Gly Ala Ala Ser Ser Thr Phe Asp Leu Thr Asn Val Val Gln>
___c___c____RECOMBINANT LEUKOTOXIN PEPTIDE [SPLIT]_c___c___c___>
___d__1640_d___d___1650d____PAA352_60__d___d__1670_d___d___1680>

           1690          1700          1710          1720
      *      *      *      *      *      *      *      *      *
CGT ATT GGT ATT GAA TTA GAC AAT GCT GGA AAT GTA ACT AAA ACC AAA
GCA TAA CCA TAA CTT AAT CTG TTA CGA CCT TTA CAT TGA TTT TGG TTT
Arg Ile Gly Ile Glu Leu Asp Asn Ala Gly Asn Val Thr Lys Thr Lys>
___c___c____RECOMBINANT LEUKOTOXIN PEPTIDE [SPLIT]_c___c___c___>
___d___d_1690__d___d__1700__PAA352_1710d___d___d_1720__d___d___>

1730          1740          1750          1760          1770
   *      *      *      *      *      *      *      *      *      *
GAA ACA AAA ATT ATT GCC AAA CTT GGT GAA GGT GAT GAC AAC GTA TTT
CTT TGT TTT TAA TAA CGG TTT GAA CCA CTT CCA CTA CTG TTG CAT AAA
Glu Thr Lys Ile Ile Ala Lys Leu Gly Glu Gly Asp Asp Asn Val Phe>
___c___c____RECOMBINANT LEUKOTOXIN PEPTIDE [SPLIT]_c___c___c___>
1730_d___d___1740d___d___d_1_PAA352__d__1760_d___d___1770d___d___>

  1780          1790          1800          1810          1820
      *      *      *      *      *      *      *      *      *
GTT GGT TCT GGT ACG ACG GAA ATT GAT GGC GGT GAA GGT TAC GAC CGA
CAA CCA AGA CCA TGC TGC CTT TAA CTA CCG CCA CTT CCA ATG CTG GCT
Val Gly Ser Gly Thr Thr Glu Ile Asp Gly Gly Glu Gly Tyr Asp Arg>
___c___c____RECOMBINANT LEUKOTOXIN PEPTIDE [SPLIT]_c___c___c___>
_1780__d___d__1790_d___d____PAA352_d___d_1810__d___d__1820_d___>

   1830          1840          1850          1860          1870
*      *      *      *      *      *      *      *      *      *
GTT CAC TAT AGC CGT GGA AAC TAT GGT GCT TTA ACT ATT GAT GCA ACC
CAA GTG ATA TCG GCA CCT TTG ATA CCA CGA AAT TGA TAA CTA CGT TGG
Val His Tyr Ser Arg Gly Asn Tyr Gly Ala Leu Thr Ile Asp Ala Thr>
___c___c____RECOMBINANT LEUKOTOXIN PEPTIDE [SPLIT]_c___c___c___>
___1830d___d___d_1840__d____PAA352_d___d___1860d___d___d_1870__>

        1880          1890           1900          1910          1920
   *      *      *      *      *      *      *      *      *      *
AAA GAG ACC GAG CAA GGT AGT TAT ACC GTA AAT CGT TTC GTA GAA ACC
TTT CTC TGG CTC GTT CCA TCA ATA TGG CAT TTA GCA AAG CAT CTT TGG
Lys Glu Thr Glu Gln Gly Ser Tyr Thr Val Asn Arg Phe Val Glu Thr>
___c___c____RECOMBINANT LEUKOTOXIN PEPTIDE [SPLIT]_c___c___c___>
___d__1880_d___d___1890d____PAA352_00__d___d__1910_d___d___1920>
```

*FIG. 7G*

```
         1930       1940       1950       1960
      *     *    *     *     *     *     *     *     *
GGT AAA GCA CTA CAC GAA GTG ACT TCA ACC CAT ACC GCA TTA GTG GGC
CCA TTT CGT GAT GTG CTT CAC TGA AGT TGG GTA TGG CGT AAT CAC CCG
Gly Lys Ala Leu His Glu Val Thr Ser Thr His Thr Ala Leu Val Gly>
___c___c____RECOMBINANT LEUKOTOXIN PEPTIDE [SPLIT]_c___c___c___>
___d___d_1930__d___d__1940__PAA352_1950d___d___d_1960__d___d___>

1970       1980       1990       2000       2010
  *     *     *     *     *     *     *     *     *     *
AAC CGT GAA GAA AAA ATA GAA TAT CGT CAT AGC AAT AAC CAG CAC CAT
TTG GCA CTT CTT TTT TAT CTT ATA GCA GTA TCG TTA TTG GTC GTG GTA
Asn Arg Glu Glu Lys Ile Glu Tyr Arg His Ser Asn Asn Gln His His>
___c___c____RECOMBINANT LEUKOTOXIN PEPTIDE [SPLIT]_c___c___c___>
1970_d___d___1980d___d___d_1_PAA352__d__2000_d___d___2010d___d___>

 2020       2030       2040       2050       2060
    *     *     *     *     *     *     *     *     *
GCC GGT TAT TAC ACC AAA GAT ACC TTG AAA GCT GTT GAA GAA ATT ATC
CGG CCA ATA ATG TGG TTT CTA TGG AAC TTT CGA CAA CTT CTT TAA TAG
Ala Gly Tyr Tyr Thr Lys Asp Thr Leu Lys Ala Val Glu Glu Ile Ile>
___c___c____RECOMBINANT LEUKOTOXIN PEPTIDE [SPLIT]_c___c___c___>
_2020__d___d__2030_d___d____PAA352_d___d_2050__d___d__2060_d___>

    2070       2080       2090       2100       2110
*     *     *     *     *     *     *     *     *     *
GGT ACA TCA CAT AAC GAT ATC TTT AAA GGT AGT AAG TTC AAT GAT GCC
CCA TGT AGT GTA TTG CTA TAG AAA TTT CCA TCA TTC AAG TTA CTA CGG
Gly Thr Ser His Asn Asp Ile Phe Lys Gly Ser Lys Phe Asn Asp Ala>
___c___c____RECOMBINANT LEUKOTOXIN PEPTIDE [SPLIT]_c___c___c___>
___2070d___d___d_2080__d____PAA352_d___d___2100d___d___d_2110__>

      2120       2130       2140       2150       2160
  *     *     *     *     *     *     *     *     *     *
TTT AAC GGT GGT GAT GGT GTC GAT ACT ATT GAC GGT AAC GAC GGC AAT
AAA TTG CCA CCA CTA CCA CAG CTA TGA TAA CTG CCA TTG CTG CCG TTA
Phe Asn Gly Gly Asp Gly Val Asp Thr Ile Asp Gly Asn Asp Gly Asn>
___c___c____RECOMBINANT LEUKOTOXIN PEPTIDE [SPLIT]_c___c___c___>
___d__2120_d___d___2130d____PAA352_40__d___d__2150_d___d___2160>

         2170       2180       2190       2200
      *     *    *     *     *     *     *     *     *
GAC CGC TTA TTT GGT GGT AAA GGC GAT GAT ATT CTC GAT GGT GGA AAT
CTG GCG AAT AAA CCA CCA TTT CCG CTA CTA TAA GAG CTA CCA CCT TTA
Asp Arg Leu Phe Gly Gly Lys Gly Asp Asp Ile Leu Asp Gly Gly Asn>
___c___c____RECOMBINANT LEUKOTOXIN PEPTIDE [SPLIT]_c___c___c___>
___d___d_2170__d___d__2180__PAA352_2190d___d___d_2200__d___d___>
```

FIG. 7H

```
2210       2220       2230       2240       2250
  *     *     *     *     *     *     *     *     *     *
 GGT GAT GAT TTT ATC GAT GGC GGT AAA GGC AAC GAC CTA TTA CAC GGT
 CCA CTA CTA AAA TAG CTA CCG CCA TTT CCG TTG CTG GAT AAT GTG CCA
 Gly Asp Asp Phe Ile Asp Gly Gly Lys Gly Asn Asp Leu Leu His Gly>
 ___c___c____RECOMBINANT LEUKOTOXIN PEPTIDE [SPLIT]_c___c___c___>
2210_d___d___2220d___d___d_2_PAA352__d__2240_d___d___2250d___d___>

 2260       2270       2280       2290       2300
    *     *     *     *     *     *     *     *     *
 GGC AAG GGC GAT GAT ATT TTC GTT CAC CGT AAA GGC GAT GGT AAT GAT
 CCG TTC CCG CTA CTA TAA AAG CAA GTG GCA TTT CCG CTA CCA TTA CTA
 Gly Lys Gly Asp Asp Ile Phe Val His Arg Lys Gly Asp Gly Asn Asp>
 ___c___c____RECOMBINANT LEUKOTOXIN PEPTIDE [SPLIT]_c___c___c___>
 _2260__d___d__2270_d___d____PAA352_d___d_2290__d___d__2300_d___>

   2310       2320       2330       2340       2350
 *     *     *     *     *     *     *     *     *     *
 ATT ATT ACC GAT TCT GAC GGC AAT GAT AAA TTA TCA TTC TCT GAT TCG
 TAA TAA TGG CTA AGA CTG CCG TTA CTA TTT AAT AGT AAG AGA CTA AGC
 Ile Ile Thr Asp Ser Asp Gly Asn Asp Lys Leu Ser Phe Ser Asp Ser>
 ___c___c____RECOMBINANT LEUKOTOXIN PEPTIDE [SPLIT]_c___c___c___>
 ___2310d___d___d_2320__d____PAA352_d___d___2340d___d___d_2350__>

     2360       2370       2380       2390       2400
  *     *     *     *     *     *     *     *     *     *
 AAC TTA AAA GAT TTA ACA TTT GAA AAA GTT AAA CAT AAT CTT GTC ATC
 TTG AAT TTT CTA AAT TGT AAA CTT TTT CAA TTT GTA TTA GAA CAG TAG
 Asn Leu Lys Asp Leu Thr Phe Glu Lys Val Lys His Asn Leu Val Ile>
 ___c___c____RECOMBINANT LEUKOTOXIN PEPTIDE [SPLIT]_c___c___c___>
 ___d__2360_d___d___2370d____PAA352_80__d___d__2390_d___d___2400>

        2410       2420       2430       2440
     *     *     *     *     *     *     *     *     *
 ACG AAT AGC AAA AAA GAG AAA GTG ACC ATT CAA AAC TGG TTC CGA GAG
 TGC TTA TCG TTT TTT CTC TTT CAC TGG TAA GTT TTG ACC AAG GCT CTC
 Thr Asn Ser Lys Lys Glu Lys Val Thr Ile Gln Asn Trp Phe Arg Glu>
 ___c___c____RECOMBINANT LEUKOTOXIN PEPTIDE [SPLIT]_c___c___c___>
 ___d___d_2410__d___d__2420__PAA352_2430d___d___d_2440__d___d___>

2450       2460       2470       2480       2490
   *     *     *     *     *     *     *     *     *     *
 GCT GAT TTT GCT AAA GAA GTG CCT AAT TAT AAA GCA ACT AAA GAT GAG
 CGA CTA AAA CGA TTT CTT CAC GGA TTA ATA TTT CGT TGA TTT CTA CTC
 Ala Asp Phe Ala Lys Glu Val Pro Asn Tyr Lys Ala Thr Lys Asp Glu>
 ___c___c____RECOMBINANT LEUKOTOXIN PEPTIDE [SPLIT]_c___c___c___>
2450_d___d___2460d___d___d_2_PAA352__d__2480_d___d___2490d___d___>
```

FIG. 7I

```
 2500       2510       2520        2530       2540
   *    *     *     *    *     *     *    *     *
AAA ATC GAA GAA ATC ATC GGT CAA AAT GGC GAG CGG ATC ACC TCA AAG
TTT TAG CTT CTT TAG TAG CCA GTT TTA CCG CTC GCC TAG TGG AGT TTC
Lys Ile Glu Glu Ile Ile Gly Gln Asn Gly Glu Arg Ile Thr Ser Lys>
___c___c___RECOMBINANT LEUKOTOXIN PEPTIDE [SPLIT]_c___c___c___>
_2500_d___d__2510_d___d____PAA352_d___d_2530__d___d__2540_d___>

  2550       2560       2570       2580        2590
*    *     *     *    *     *     *    *     *    *
CAA GTT GAT GAT CTT ATC GCA AAA GGT AAC GGC AAA ATT ACC CAA GAT
GTT CAA CTA CTA GAA TAG CGT TTT CCA TTG CCG TTT TAA TGG GTT CTA
Gln Val Asp Asp Leu Ile Ala Lys Gly Asn Gly Lys Ile Thr Gln Asp>
___c___c___RECOMBINANT LEUKOTOXIN PEPTIDE [SPLIT]_c___c___c___>
___2550d___d___d_2560__d____PAA352_d___d___2580d___d___d_2590__>

    2600       2610       2620       2630       2640
  *    *     *     *    *     *     *    *     *    *
GAG CTA TCA AAA GTT GTT GAT AAC TAT GAA TTG CTC AAA CAT AGC AAA
CTC GAT AGT TTT CAA CAA CTA TTG ATA CTT AAC GAG TTT GTA TCG TTT
Glu Leu Ser Lys Val Val Asp Asn Tyr Glu Leu Leu Lys His Ser Lys>
___c___c___RECOMBINANT LEUKOTOXIN PEPTIDE [SPLIT]_c___c___c___>
___d__2600_d___d___2610d____PAA352_20__d___d__2630_d___d___2640>

       2650       2660       2670       2680
    *    *     *     *    *     *     *    *     *
AAT GTG ACA AAC AGC TTA GAT AAG TTA ATC TCA TCT GTA AGT GCA TTT
TTA CAC TGT TTG TCG AAT CTA TTC AAT TAG AGT AGA CAT TCA CGT AAA
Asn Val Thr Asn Ser Leu Asp Lys Leu Ile Ser Ser Val Ser Ala Phe>
___c___c___RECOMBINANT LEUKOTOXIN PEPTIDE [SPLIT]_c___c___c___>
___d___d_2650__d___d__2660__PAA352_2670d___d___d_2680__d___d___>

2690        2700       2710       2720       2730
  *    *     *     *    *     *     *    *     *    *
ACC TCG TCT AAT GAT TCG AGA AAT GTA TTA GTG GCT CCA ACT TCA ATG
TGG AGC AGA TTA CTA AGC TCT TTA CAT AAT CAC CGA GGT TGA AGT TAC
Thr Ser Ser Asn Asp Ser Arg Asn Val Leu Val Ala Pro Thr Ser Met>
___c___c___RECOMBINANT LEUKOTOXIN PEPTIDE [SPLIT]_c___c___c___>
2690_d___d___2700d___d___d_2_PAA352__d__2720_d___d___2730d___d___>

 2740       2750       2760        2770       2780
   *    *     *     *    *     *     *    *     *
TTG GAT CAA AGT TTA TCT TCT CTT CAA TTT GCT AGG GGA TC C CAG GGC
AAC CTA GTT TCA AAT AGA AGA GAA GTT AAA CGA TCC CCT AG G GTC CCG
Leu Asp Gln Ser Leu Ser Ser Leu Gln Phe Ala Arg Gly Ser>
___c___RECOMBINANT LEUKOTOXIN PEPTIDE [SPLIT]__c___c__>
                                                       Gln Gly>
                                                      _e___e___>
                                                       Gln Gly>
                                                      _f___f___>
_2740__d___d__2750_d___PAA352_0d___d___d_2770__d___d__>
                                                      _g___g___>
                                           _b___b__>

  2790       2800       2810       2820       2830
```

```
 *     *     *     *     *     *     *     *     *     *
CAA TTT TTT AGA GAA ATA GAA AAC TTA AAG GAG TAT TTT AAT GCA AGT
GTT AAA AAA TCT CTT TAT CTT TTG AAT TTC CTC ATA AAA TTA CGT TCA
Gln Phe Phe Arg Glu Ile Glu Asn Leu Lys Glu Tyr Phe Asn Ala Ser>
___e___e___e___e___e___e___e_______e___e___e___e___e___e___e___>
Gln Phe Phe Arg Glu Ile Glu Asn Leu Lys Glu Tyr Phe Asn Ala Ser>
___f___f___f___f___f___f___f_______f___f___f___f___f___f___f___>
170_g___g___g180g___g___g___BOVIFNG_g___200_g___g___g210g___g___>

        2840        2850         2860        2870        2880
   *     *     *     *     *     *     *     *     *     *
AGC CCA GAT GTA GCT AAG GGT GGG CCT CTC TTC TCA GAA ATT TTG AAG
TCG GGT CTA CAT CGA TTC CCA CCC GGA GAG AAG AGT CTT TAA AAC TTC
Ser Pro Asp Val Ala Lys Gly Gly Pro Leu Phe Ser Glu Ile Leu Lys>
___e___e___e___e___e___e___e_______e___e___e___e___e___e___e___>
Ser Pro Asp Val Ala Lys Gly Gly Pro Leu Phe Ser Glu Ile Leu Lys>
___f___f___f___f___f___f___f_______f___f___f___f___f___f___f___>
__220__g___g___230_g___g___BOVIFNG_g___g__250__g___g___260_g___>

           2890        2900        2910        2920
      *     *     *     *     *     *     *     *     *
AAT TGG AAA GAT GAA AGT GAC AAA AAA ATT ATT CAG AGC CAA ATT GTC
TTA ACC TTT CTA CTT TCA CTG TTT TTT TAA TAA GTC TCG GTT TAA CAG
Asn Trp Lys Asp Glu Ser Asp Lys Lys Ile Ile Gln Ser Gln Ile Val>
___e___e___e___e___e___e___e_______e___e___e___e___e___e___e___>
Asn Trp Lys Asp Glu Ser Asp Lys Lys Ile Ile Gln Ser Gln Ile Val>
___f___f___f___f___f___f___f_______f___f___f___f___f___f___f___>
___g270g___g___g__280__g___BOVIFNG_g___g___g300g___g___g__310__>

2930        2940        2950        2960        2970
 *     *     *     *     *     *     *     *     *     *
TCC TTC TAC TTC AAA CTC TTT GAA AAC CTC AAA GAT AAC CAG GTC ATT
AGG AAG ATG AAG TTT GAG AAA CTT TTG GAG TTT CTA TTG GTC CAG TAA
Ser Phe Tyr Phe Lys Leu Phe Glu Asn Leu Lys Asp Asn Gln Val Ile>
___e___e___e___e___e___e___e_______e___e___e___e___e___e___e___>
Ser Phe Tyr Phe Lys Leu Phe Glu Asn Leu Lys Asp Asn Gln Val Ile>
___f___f___f___f___f___f___f_______f___f___f___f___f___f___f___>
___g___320_g___g___g330g___BOVIFNG_40__g___g___350_g___g___g360>

 2980        2990        3000        3010        3020
    *     *     *     *     *     *     *     *     *
CAA AGG AGC ATG GAT ATC ATC AAG CAA GAC ATG TTT CAG AAG TTC TTG
GTT TCC TCG TAC CTA TAG TAG TTC GTT CTG TAC AAA GTC TTC AAG AAC
Gln Arg Ser Met Asp Ile Ile Lys Gln Asp Met Phe Gln Lys Phe Leu>
___e___e___e___e___e___e___e_______e___e___e___e___e___e___e___>
Gln Arg Ser Met Asp Ile Ile Lys Gln Asp Met Phe Gln Lys Phe Leu>
___f___f___f___f___f___f___f_______f___f___f___f___f___f___f___>
___g___g__370__g___g___380_BOVIFNG_g390g___g___g__400__g___g___>

    3030        3040        3050        3060        3070
 *     *     *     *     *     *     *     *     *     *
AAT GGC AGC TCT GAG AAA CTG GAG GAC TTC AAA AAG CTG ATT CAA ATT
TTA CCG TCG AGA CTC TTT GAC CTC CTG AAG TTT TTC GAC TAA GTT TAA
Asn Gly Ser Ser Glu Lys Leu Glu Asp Phe Lys Lys Leu Ile Gln Ile>
___e___e___e___e___e___e___e_______e___e___e___e___e___e___e___>
Asn Gly Ser Ser Glu Lys Leu Glu Asp Phe Lys Lys Leu Ile Gln Ile>
```

FIG. 7K

```
___f___f___f___f___f___f___f_______f___f___f___f___f___f___f___>
410_g___g___g420g___g___g___BOVIFNG_g___440_g___g___g450g___g___>

        3080          3090           3100          3110         3120
   *       *       *      *       *       *      *       *       *      *
CCG GTG GAT GAT CTG CAG ATC CAG CGC AAA GCC ATA AAT GAA CTC ATC
GGC CAC CTA CTA GAC GTC TAG GTC GCG TTT CGG TAT TTA CTT GAG TAG
Pro Val Asp Asp Leu Gln Ile Gln Arg Lys Ala Ile Asn Glu Leu Ile>
___e___e___e___e___e___e___e_______e___e___e___e___e___e___e___>
Pro Val Asp Asp Leu Gln Ile Gln Arg Lys Ala Ile Asn Glu Leu Ile>
___f___f___f___f___f___f___f_______f___f___f___f___f___f___f___>
__460__g___g___470_g___g___BOVIFNG_g___g__490__g___g___500_g___>

          3130          3140          3150          3160
      *       *      *       *       *      *       *       *      *
AAA GTG ATG AAT GAC CTG TCA CCA AAA TCT AAC CTC AGA AAG CGG AAG
TTT CAC TAC TTA CTG GAC AGT GGT TTT AGA TTG GAG TCT TTC GCC TTC
Lys Val Met Asn Asp Leu Ser Pro Lys Ser Asn Leu Arg Lys Arg Lys>
___e___e___e___e___e___e___e_______e___e___e___e___e___e___e___>
Lys Val Met Asn Asp Leu Ser Pro Lys Ser Asn Leu Arg Lys Arg Lys>
___f___f___f___f___f___f___f_______f___f___f___f___f___f___f___>
___g510g___g___g__520__g___BOVIFNG_g___g___g540g___g___g__550__>

3170          3180           3190          3200          3210
   *       *      *       *       *      *       *      *      *     *
AGA AGT CAG AAT CTC TTT CGA GGC CGG AGA GCA TCA ACG TAATGGTCC
TCT TCA GTC TTA GAG AAA GCT CCG GCC TCT CGT AGT TGC ATTACCAGG
Arg Ser Gln Asn Leu Phe Arg Gly Arg Arg Ala Ser Thr>
___e___e___e___e___e___e___e___e___e___e___e___e___>
Arg Ser Gln Asn Leu Phe Arg Gly Arg Arg Ala Ser Thr>
___f___f___f___f___f___f___f___f___f___f___f___f___>
___g___560_g___g___g570g__BOVIFNG_580__g___g___590_g_______600>

3220
   *      *
TCCTGCCTGCAAT
AGGACGGACGTTA
________610___>
```

*FIG. 7L*

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
(A) LENGTH: 3311 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 1..3294

(xi) SEQUENCE DESCRIPTION: SEQ ID NO:1:

```
ATG GCT ACT GTT AAT AGA TCT GCA CCT ACT TCA AGC TCT ACG GGG AAC        48
Met Ala Thr Val Asn Arg Ser Ala Pro Thr Ser Ser Ser Thr Gly Asn
  1               5                  10                  15

ACA ATG AAA GAA GTG AAG TCA TTG CTG CTG GAT TTA CAG TTG CTT TTG        96
Thr Met Lys Glu Val Lys Ser Leu Leu Leu Asp Leu Gln Leu Leu Leu
             20                  25                  30

GAG AAA GTT AAA AAT CCT GAG AAC CTC AAG CTC TCC AGG ATG CAT ACA       144
Glu Lys Val Lys Asn Pro Glu Asn Leu Lys Leu Ser Arg Met His Thr
         35                  40                  45

TTT GAC TTT TAC GTG CCC AAG GTT AAC GCT ACA GAA TTG AAA CAT CTT       192
Phe Asp Phe Tyr Val Pro Lys Val Asn Ala Thr Glu Leu Lys His Leu
     50                  55                  60

AAG TGT TTA CTA GAA GAA CTC AAA CTT CTA GAG GAA GTG CTA AAT TTA       240
Lys Cys Leu Leu Glu Glu Leu Lys Leu Leu Glu Glu Val Leu Asn Leu
 65                  70                  75                  80

GCT CCA AGC AAA AAC CTG AAC CCC AGA GAG ATC AAG GAT TCA ATG GAC       288
Ala Pro Ser Lys Asn Leu Asn Pro Arg Glu Ile Lys Asp Ser Met Asp
                 85                  90                  95

AAT ATC AAG AGA ATC GTT TTG GAA CTA CAG GGA TCT GAA ACA AGA TTC       336
Asn Ile Lys Arg Ile Val Leu Glu Leu Gln Gly Ser Glu Thr Arg Phe
            100                 105                 110

ACA TGT GAA TAT GAT GAT GCA ACA GTA AAC GCT GTA GAA TTT CTG AAC       384
Thr Cys Glu Tyr Asp Asp Ala Thr Val Asn Ala Val Glu Phe Leu Asn
        115                 120                 125

AAA TGG ATT ACC TTT TGT CAA AGC ATC TAC TCA ACA ATG ACT GGG GAT       432
Lys Trp Ile Thr Phe Cys Gln Ser Ile Tyr Ser Thr Met Thr Gly Asp
    130                 135                 140

CTA AGC TTC CCT AGA CTT ACA ACC CTA TCA AAT GGG CTA AAA AAC ACT       480
Leu Ser Phe Pro Arg Leu Thr Thr Leu Ser Asn Gly Leu Lys Asn Thr
145                 150                 155                 160

TTA ACG GCA ACC AAA AGT GGC TTA CAT AAA GCC GGT CAA TCA TTA ACC       528
Leu Thr Ala Thr Lys Ser Gly Leu His Lys Ala Gly Gln Ser Leu Thr
                165                 170                 175

CAA GCC GGC AGT TCT TTA AAA ACT GGG GCA AAA AAA ATT ATC CTC TAT       576
Gln Ala Gly Ser Ser Leu Lys Thr Gly Ala Lys Lys Ile Ile Leu Tyr
            180                 185                 190

ATT CCC CAA AAT TAC CAA TAT GAT ACT GAA CAA GGT AAT GGT TTA CAG       624
Ile Pro Gln Asn Tyr Gln Tyr Asp Thr Glu Gln Gly Asn Gly Leu Gln
        195                 200                 205

GAT TTA GTC AAA GCG GCC GAA GAG TTG GGG ATT GAG GTA CAA AGA GAA       672
Asp Leu Val Lys Ala Ala Glu Glu Leu Gly Ile Glu Val Gln Arg Glu
    210                 215                 220
```

-continued

```
GAA CGC AAT AAT ATT GCA ACA GCT CAA ACC AGT TTA GGC ACG ATT CAA       720
Glu Arg Asn Asn Ile Ala Thr Ala Gln Thr Ser Leu Gly Thr Ile Gln
225                 230                 235                 240

ACC GCT ATT GGC TTA ACT GAG CGT GGC ATT GTG TTA TCC GCT CCA CAA       768
Thr Ala Ile Gly Leu Thr Glu Arg Gly Ile Val Leu Ser Ala Pro Gln
                245                 250                 255

ATT GAT AAA TTG CTA CAG AAA ACT AAA GCA GGC CAA GCA TTA GGT TCT       816
Ile Asp Lys Leu Leu Gln Lys Thr Lys Ala Gly Gln Ala Leu Gly Ser
            260                 265                 270

GCC GAA AGC ATT GTA CAA AAT GCA AAT AAA GCC AAA ACT GTA TTA TCT       864
Ala Glu Ser Ile Val Gln Asn Ala Asn Lys Ala Lys Thr Val Leu Ser
        275                 280                 285

GGC ATT CAA TCT ATT TTA GGC TCA GTA TTG GCT GGA ATG GAT TTA GAT       912
Gly Ile Gln Ser Ile Leu Gly Ser Val Leu Ala Gly Met Asp Leu Asp
    290                 295                 300

GAG GCC TTA CAG AAT AAC AGC AAC CAA CAT GCT CTT GCT AAA GCT GGC       960
Glu Ala Leu Gln Asn Asn Ser Asn Gln His Ala Leu Ala Lys Ala Gly
305                 310                 315                 320

TTG GAG CTA ACA AAT TCA TTA ATT GAA AAT ATT GCT AAT TCA GTA AAA      1008
Leu Glu Leu Thr Asn Ser Leu Ile Glu Asn Ile Ala Asn Ser Val Lys
                325                 330                 335

ACA CTT GAC GAA TTT GGT GAG CAA ATT AGT CAA TTT GGT TCA AAA CTA      1056
Thr Leu Asp Glu Phe Gly Glu Gln Ile Ser Gln Phe Gly Ser Lys Leu
            340                 345                 350

CAA AAT ATC AAA GGC TTA GGG ACT TTA GGA GAC AAA CTC AAA AAT ATC      1104
Gln Asn Ile Lys Gly Leu Gly Thr Leu Gly Asp Lys Leu Lys Asn Ile
        355                 360                 365

GGT GGA CTT GAT AAA GCT GGC CTT GGT TTA GAT GTT ATC TCA GGG CTA      1152
Gly Gly Leu Asp Lys Ala Gly Leu Gly Leu Asp Val Ile Ser Gly Leu
    370                 375                 380

TTA TCG GGC GCA ACA GCT GCA CTT GTA CTT GCA GAT AAA AAT GCT TCA      1200
Leu Ser Gly Ala Thr Ala Ala Leu Val Leu Ala Asp Lys Asn Ala Ser
385                 390                 395                 400

ACA GCT AAA AAA GTG GGT GCG GGT TTT GAA TTG GCA AAC CAA GTT GTT      1248
Thr Ala Lys Lys Val Gly Ala Gly Phe Glu Leu Ala Asn Gln Val Val
                405                 410                 415

GGT AAT ATT ACC AAA GCC GTT TCT TCT TAC ATT TTA GCC CAA CGT GTT      1296
Gly Asn Ile Thr Lys Ala Val Ser Ser Tyr Ile Leu Ala Gln Arg Val
            420                 425                 430

GCA GCA GGT TTA TCT TCA ACT GGG CCT GTG GCT GCT TTA ATT GCT TCT      1344
Ala Ala Gly Leu Ser Ser Thr Gly Pro Val Ala Ala Leu Ile Ala Ser
        435                 440                 445

ACT GTT TCT CTT GCG ATT AGC CCA TTA GCA TTT GCC GGT ATT GCC GAT      1392
Thr Val Ser Leu Ala Ile Ser Pro Leu Ala Phe Ala Gly Ile Ala Asp
    450                 455                 460

AAA TTT AAT CAT GCA AAA AGT TTA GAG AGT TAT GCC GAA CGC TTT AAA      1440
Lys Phe Asn His Ala Lys Ser Leu Glu Ser Tyr Ala Glu Arg Phe Lys
465                 470                 475                 480

AAA TTA GGC TAT GAC GGA GAT AAT TTA TTA GCA GAA TAT CAG CGG GGA      1488
Lys Leu Gly Tyr Asp Gly Asp Asn Leu Leu Ala Glu Tyr Gln Arg Gly
                485                 490                 495

ACA GGG ACT ATT GAT GCA TCG GTT ACT GCA ATT AAT ACC GCA TTG GCC      1536
Thr Gly Thr Ile Asp Ala Ser Val Thr Ala Ile Asn Thr Ala Leu Ala
            500                 505                 510

GCT ATT GCT GGT GGT GTG TCT GCT GCT GCA GCC GGC TCG GTT ATT GCT      1584
Ala Ile Ala Gly Gly Val Ser Ala Ala Ala Ala Gly Ser Val Ile Ala
        515                 520                 525

TCA CCG ATT GCC TTA TTA GTA TCT GGG ATT ACC GGT GTA ATT TCT ACG      1632
Ser Pro Ile Ala Leu Leu Val Ser Gly Ile Thr Gly Val Ile Ser Thr
```

-continued

```
    530                 535                 540

ATT CTG CAA TAT TCT AAA CAA GCA ATG TTT GAG CAC GTT GCA AAT AAA     1680
Ile Leu Gln Tyr Ser Lys Gln Ala Met Phe Glu His Val Ala Asn Lys
545                 550                 555                 560

ATT CAT AAC AAA ATT GTA GAA TGG GAA AAA AAT AAT CAC GGT AAG AAC     1728
Ile His Asn Lys Ile Val Glu Trp Glu Lys Asn Asn His Gly Lys Asn
                565                 570                 575

TAC TTT GAA AAT GGT TAC GAT GCC CGT TAT CTT GCG AAT TTA CAA GAT     1776
Tyr Phe Glu Asn Gly Tyr Asp Ala Arg Tyr Leu Ala Asn Leu Gln Asp
            580                 585                 590

AAT ATG AAA TTC TTA CTG AAC TTA AAC AAA GAG TTA CAG GCA GAA CGT     1824
Asn Met Lys Phe Leu Leu Asn Leu Asn Lys Glu Leu Gln Ala Glu Arg
        595                 600                 605

GTC ATC GCT ATT ACT CAG CAG CAA TGG GAT AAC AAC ATT GGT GAT TTA     1872
Val Ile Ala Ile Thr Gln Gln Gln Trp Asp Asn Asn Ile Gly Asp Leu
    610                 615                 620

GCT GGT ATT AGC CGT TTA GGT GAA AAA GTC CTT AGT GGT AAA GCC TAT     1920
Ala Gly Ile Ser Arg Leu Gly Glu Lys Val Leu Ser Gly Lys Ala Tyr
625                 630                 635                 640

GTG GAT GCG TTT GAA GAA GGC AAA CAC ATT AAA GCC GAT AAA TTA GTA     1968
Val Asp Ala Phe Glu Glu Gly Lys His Ile Lys Ala Asp Lys Leu Val
                645                 650                 655

CAG TTG GAT TCG GCA AAC GGT ATT ATT GAT GTG AGT AAT TCG GGT AAA     2016
Gln Leu Asp Ser Ala Asn Gly Ile Ile Asp Val Ser Asn Ser Gly Lys
            660                 665                 670

GCG AAA ACT CAG CAT ATC TTA TTC AGA ACG CCA TTA TTG ACG CCG GGA     2064
Ala Lys Thr Gln His Ile Leu Phe Arg Thr Pro Leu Leu Thr Pro Gly
        675                 680                 685

ACA GAG CAT CGT GAA CGC GTA CAA ACA GGT AAA TAT GAA TAT ATT ACC     2112
Thr Glu His Arg Glu Arg Val Gln Thr Gly Lys Tyr Glu Tyr Ile Thr
    690                 695                 700

AAG CTC AAT ATT AAC CGT GTA GAT AGC TGG AAA ATT ACA GAT GGT GCA     2160
Lys Leu Asn Ile Asn Arg Val Asp Ser Trp Lys Ile Thr Asp Gly Ala
705                 710                 715                 720

GCA AGT TCT ACC TTT GAT TTA ACT AAC GTT GTT CAG CGT ATT GGT ATT     2208
Ala Ser Ser Thr Phe Asp Leu Thr Asn Val Val Gln Arg Ile Gly Ile
                725                 730                 735

GAA TTA GAC AAT GCT GGA AAT GTA ACT AAA ACC AAA GAA ACA AAA ATT     2256
Glu Leu Asp Asn Ala Gly Asn Val Thr Lys Thr Lys Glu Thr Lys Ile
            740                 745                 750

ATT GCC AAA CTT GGT GAA GGT GAT GAC AAC GTA TTT GTT GGT TCT GGT     2304
Ile Ala Lys Leu Gly Glu Gly Asp Asp Asn Val Phe Val Gly Ser Gly
        755                 760                 765

ACG ACG GAA ATT GAT GGC GGT GAA GGT TAC GAC CGA GTT CAC TAT AGC     2352
Thr Thr Glu Ile Asp Gly Gly Glu Gly Tyr Asp Arg Val His Tyr Ser
    770                 775                 780

CGT GGA AAC TAT GGT GCT TTA ACT ATT GAT GCA ACC AAA GAG ACC GAG     2400
Arg Gly Asn Tyr Gly Ala Leu Thr Ile Asp Ala Thr Lys Glu Thr Glu
785                 790                 795                 800

CAA GGT AGT TAT ACC GTA AAT CGT TTC GTA GAA ACC GGT AAA GCA CTA     2448
Gln Gly Ser Tyr Thr Val Asn Arg Phe Val Glu Thr Gly Lys Ala Leu
                805                 810                 815

CAC GAA GTG ACT TCA ACC CAT ACC GCA TTA GTG GGC AAC CGT GAA GAA     2496
His Glu Val Thr Ser Thr His Thr Ala Leu Val Gly Asn Arg Glu Glu
            820                 825                 830

AAA ATA GAA TAT CGT CAT AGC AAT AAC CAG CAC CAT GCC GGT TAT TAC     2544
Lys Ile Glu Tyr Arg His Ser Asn Asn Gln His His Ala Gly Tyr Tyr
        835                 840                 845

ACC AAA GAT ACC TTG AAA GCT GTT GAA GAA ATT ATC GGT ACA TCA CAT     2592
```

-continued

```
Thr Lys Asp Thr Leu Lys Ala Val Glu Glu Ile Ile Gly Thr Ser His
    850                 855                 860

AAC GAT ATC TTT AAA GGT AGT AAG TTC AAT GAT GCC TTT AAC GGT GGT      2640
Asn Asp Ile Phe Lys Gly Ser Lys Phe Asn Asp Ala Phe Asn Gly Gly
865                 870                 875                 880

GAT GGT GTC GAT ACT ATT GAC GGT AAC GAC GGC AAT GAC CGC TTA TTT      2688
Asp Gly Val Asp Thr Ile Asp Gly Asn Asp Gly Asn Asp Arg Leu Phe
                885                 890                 895

GGT GGT AAA GGC GAT GAT ATT CTC GAT GGT GGA AAT GGT GAT GAT TTT      2736
Gly Gly Lys Gly Asp Asp Ile Leu Asp Gly Gly Asn Gly Asp Asp Phe
            900                 905                 910

ATC GAT GGC GGT AAA GGC AAC GAC CTA TTA CAC GGT GGC AAG GGC GAT      2784
Ile Asp Gly Gly Lys Gly Asn Asp Leu Leu His Gly Gly Lys Gly Asp
        915                 920                 925

GAT ATT TTC GTT CAC CGT AAA GGC GAT GGT AAT GAT ATT ATT ACC GAT      2832
Asp Ile Phe Val His Arg Lys Gly Asp Gly Asn Asp Ile Ile Thr Asp
    930                 935                 940

TCT GAC GGC AAT GAT AAA TTA TCA TTC TCT GAT TCG AAC TTA AAA GAT      2880
Ser Asp Gly Asn Asp Lys Leu Ser Phe Ser Asp Ser Asn Leu Lys Asp
945                 950                 955                 960

TTA ACA TTT GAA AAA GTT AAA CAT AAT CTT GTC ATC ACG AAT AGC AAA      2928
Leu Thr Phe Glu Lys Val Lys His Asn Leu Val Ile Thr Asn Ser Lys
                965                 970                 975

AAA GAG AAA GTG ACC ATT CAA AAC TGG TTC CGA GAG GCT GAT TTT GCT      2976
Lys Glu Lys Val Thr Ile Gln Asn Trp Phe Arg Glu Ala Asp Phe Ala
            980                 985                 990

AAA GAA GTG CCT AAT TAT AAA GCA ACT AAA GAT GAG AAA ATC GAA GAA      3024
Lys Glu Val Pro Asn Tyr Lys Ala Thr Lys Asp Glu Lys Ile Glu Glu
        995                 1000                1005

ATC ATC GGT CAA AAT GGC GAG CGG ATC ACC TCA AAG CAA GTT GAT GAT      3072
Ile Ile Gly Gln Asn Gly Glu Arg Ile Thr Ser Lys Gln Val Asp Asp
    1010                1015                1020

CTT ATC GCA AAA GGT AAC GGC AAA ATT ACC CAA GAT GAG CTA TCA AAA      3120
Leu Ile Ala Lys Gly Asn Gly Lys Ile Thr Gln Asp Glu Leu Ser Lys
1025                1030                1035                1040

GTT GTT GAT AAC TAT GAA TTG CTC AAA CAT AGC AAA AAT GTG ACA AAC      3168
Val Val Asp Asn Tyr Glu Leu Leu Lys His Ser Lys Asn Val Thr Asn
                1045                1050                1055

AGC TTA GAT AAG TTA ATC TCA TCT GTA AGT GCA TTT ACC TCG TCT AAT      3216
Ser Leu Asp Lys Leu Ile Ser Ser Val Ser Ala Phe Thr Ser Ser Asn
            1060                1065                1070

GAT TCG AGA AAT GTA TTA GTG GCT CCA ACT TCA ATG TTG GAT CAA AGT      3264
Asp Ser Arg Asn Val Leu Val Ala Pro Thr Ser Met Leu Asp Gln Ser
        1075                1080                1085

TTA TCT TCT CTT CAA TTT GCT AGG GGA TCC TAGCTAGCTA GCCATGG          3311
Leu Ser Ser Leu Gln Phe Ala Arg Gly Ser
    1090                1095
```

(2) INFORMATION FOR SEQ ID NO:2:

(i) SEQUENCE CHARACTERISTICS:
(A) LENGTH: 1098 amino acids
(B) TYPE: amino acid
(D) TOPOLOGY: linear (ii) MOLECULE TYPE: protein (xi) SEQUENCE DESCRIPTION: SEQ ID NO:2:

```
Met Ala Thr Val Asn Arg Ser Ala Pro Thr Ser Ser Ser Thr Gly Asn
  1               5                  10                  15

Thr Met Lys Glu Val Lys Ser Leu Leu Leu Asp Leu Gln Leu Leu Leu
```

-continued

```
                20                  25                  30

Glu Lys Val Lys Asn Pro Glu Asn Leu Lys Leu Ser Arg Met His Thr
        35                  40                  45

Phe Asp Phe Tyr Val Pro Lys Val Asn Ala Thr Glu Leu Lys His Leu
    50                  55                  60

Lys Cys Leu Leu Glu Glu Leu Lys Leu Leu Glu Glu Val Leu Asn Leu
65                  70                  75                  80

Ala Pro Ser Lys Asn Leu Asn Pro Arg Glu Ile Lys Asp Ser Met Asp
                85                  90                  95

Asn Ile Lys Arg Ile Val Leu Glu Leu Gln Gly Ser Glu Thr Arg Phe
            100                 105                 110

Thr Cys Glu Tyr Asp Asp Ala Thr Val Asn Ala Val Glu Phe Leu Asn
        115                 120                 125

Lys Trp Ile Thr Phe Cys Gln Ser Ile Tyr Ser Thr Met Thr Gly Asp
    130                 135                 140

Leu Ser Phe Pro Arg Leu Thr Thr Leu Ser Asn Gly Leu Lys Asn Thr
145                 150                 155                 160

Leu Thr Ala Thr Lys Ser Gly Leu His Lys Ala Gly Gln Ser Leu Thr
                165                 170                 175

Gln Ala Gly Ser Ser Leu Lys Thr Gly Ala Lys Lys Ile Ile Leu Tyr
            180                 185                 190

Ile Pro Gln Asn Tyr Gln Tyr Asp Thr Glu Gln Gly Asn Gly Leu Gln
        195                 200                 205

Asp Leu Val Lys Ala Ala Glu Glu Leu Gly Ile Glu Val Gln Arg Glu
    210                 215                 220

Glu Arg Asn Asn Ile Ala Thr Ala Gln Thr Ser Leu Gly Thr Ile Gln
225                 230                 235                 240

Thr Ala Ile Gly Leu Thr Glu Arg Gly Ile Val Leu Ser Ala Pro Gln
                245                 250                 255

Ile Asp Lys Leu Leu Gln Lys Thr Lys Ala Gly Gln Ala Leu Gly Ser
            260                 265                 270

Ala Glu Ser Ile Val Gln Asn Ala Asn Lys Ala Lys Thr Val Leu Ser
        275                 280                 285

Gly Ile Gln Ser Ile Leu Gly Ser Val Leu Ala Gly Met Asp Leu Asp
    290                 295                 300

Glu Ala Leu Gln Asn Asn Ser Asn Gln His Ala Leu Ala Lys Ala Gly
305                 310                 315                 320

Leu Glu Leu Thr Asn Ser Leu Ile Glu Asn Ile Ala Asn Ser Val Lys
                325                 330                 335

Thr Leu Asp Glu Phe Gly Glu Gln Ile Ser Gln Phe Gly Ser Lys Leu
            340                 345                 350

Gln Asn Ile Lys Gly Leu Gly Thr Leu Gly Asp Lys Leu Lys Asn Ile
        355                 360                 365

Gly Gly Leu Asp Lys Ala Gly Leu Gly Leu Asp Val Ile Ser Gly Leu
    370                 375                 380

Leu Ser Gly Ala Thr Ala Ala Leu Val Leu Ala Asp Lys Asn Ala Ser
385                 390                 395                 400

Thr Ala Lys Lys Val Gly Ala Gly Phe Glu Leu Ala Asn Gln Val Val
                405                 410                 415

Gly Asn Ile Thr Lys Ala Val Ser Ser Tyr Ile Leu Ala Gln Arg Val
            420                 425                 430

Ala Ala Gly Leu Ser Ser Thr Gly Pro Val Ala Ala Leu Ile Ala Ser
        435                 440                 445
```

-continued

```
Thr Val Ser Leu Ala Ile Ser Pro Leu Ala Phe Ala Gly Ile Ala Asp
    450                 455                 460

Lys Phe Asn His Ala Lys Ser Leu Glu Ser Tyr Ala Glu Arg Phe Lys
465                 470                 475                 480

Lys Leu Gly Tyr Asp Gly Asp Asn Leu Leu Ala Glu Tyr Gln Arg Gly
                485                 490                 495

Thr Gly Thr Ile Asp Ala Ser Val Thr Ala Ile Asn Thr Ala Leu Ala
            500                 505                 510

Ala Ile Ala Gly Gly Val Ser Ala Ala Ala Gly Ser Val Ile Ala
        515                 520                 525

Ser Pro Ile Ala Leu Leu Val Ser Gly Ile Thr Gly Val Ile Ser Thr
    530                 535                 540

Ile Leu Gln Tyr Ser Lys Gln Ala Met Phe Glu His Val Ala Asn Lys
545                 550                 555                 560

Ile His Asn Lys Ile Val Glu Trp Glu Lys Asn Asn His Gly Lys Asn
                565                 570                 575

Tyr Phe Glu Asn Gly Tyr Asp Ala Arg Tyr Leu Ala Asn Leu Gln Asp
            580                 585                 590

Asn Met Lys Phe Leu Leu Asn Leu Asn Lys Glu Leu Gln Ala Glu Arg
        595                 600                 605

Val Ile Ala Ile Thr Gln Gln Gln Trp Asp Asn Asn Ile Gly Asp Leu
    610                 615                 620

Ala Gly Ile Ser Arg Leu Gly Glu Lys Val Leu Ser Gly Lys Ala Tyr
625                 630                 635                 640

Val Asp Ala Phe Glu Glu Gly Lys His Ile Lys Ala Asp Lys Leu Val
                645                 650                 655

Gln Leu Asp Ser Ala Asn Gly Ile Ile Asp Val Ser Asn Ser Gly Lys
            660                 665                 670

Ala Lys Thr Gln His Ile Leu Phe Arg Thr Pro Leu Leu Thr Pro Gly
        675                 680                 685

Thr Glu His Arg Glu Arg Val Gln Thr Gly Lys Tyr Glu Tyr Ile Thr
    690                 695                 700

Lys Leu Asn Ile Asn Arg Val Asp Ser Trp Lys Ile Thr Asp Gly Ala
705                 710                 715                 720

Ala Ser Ser Thr Phe Asp Leu Thr Asn Val Val Gln Arg Ile Gly Ile
                725                 730                 735

Glu Leu Asp Asn Ala Gly Asn Val Thr Lys Thr Lys Glu Thr Lys Ile
            740                 745                 750

Ile Ala Lys Leu Gly Glu Gly Asp Asp Asn Val Phe Val Gly Ser Gly
        755                 760                 765

Thr Thr Glu Ile Asp Gly Gly Glu Gly Tyr Asp Arg Val His Tyr Ser
    770                 775                 780

Arg Gly Asn Tyr Gly Ala Leu Thr Ile Asp Ala Thr Lys Glu Thr Glu
785                 790                 795                 800

Gln Gly Ser Tyr Thr Val Asn Arg Phe Val Glu Thr Gly Lys Ala Leu
                805                 810                 815

His Glu Val Thr Ser Thr His Thr Ala Leu Val Gly Asn Arg Glu Glu
            820                 825                 830

Lys Ile Glu Tyr Arg His Ser Asn Asn Gln His His Ala Gly Tyr Tyr
        835                 840                 845

Thr Lys Asp Thr Leu Lys Ala Val Glu Glu Ile Ile Gly Thr Ser His
    850                 855                 860
```

-continued

```
Asn Asp Ile Phe Lys Gly Ser Lys Phe Asn Asp Ala Phe Asn Gly Gly
865                 870                 875                 880

Asp Gly Val Asp Thr Ile Asp Gly Asn Asp Gly Asn Asp Arg Leu Phe
                885                 890                 895

Gly Gly Lys Gly Asp Asp Ile Leu Asp Gly Gly Asn Gly Asp Asp Phe
            900                 905                 910

Ile Asp Gly Gly Lys Gly Asn Asp Leu Leu His Gly Gly Lys Gly Asp
        915                 920                 925

Asp Ile Phe Val His Arg Lys Gly Asp Gly Asn Asp Ile Ile Thr Asp
    930                 935                 940

Ser Asp Gly Asn Asp Lys Leu Ser Phe Ser Asp Ser Asn Leu Lys Asp
945                 950                 955                 960

Leu Thr Phe Glu Lys Val Lys His Asn Leu Val Ile Thr Asn Ser Lys
                965                 970                 975

Lys Glu Lys Val Thr Ile Gln Asn Trp Phe Arg Glu Ala Asp Phe Ala
            980                 985                 990

Lys Glu Val Pro Asn Tyr Lys Ala Thr Lys Asp Glu Lys Ile Glu Glu
        995                 1000                1005

Ile Ile Gly Gln Asn Gly Glu Arg Ile Thr Ser Lys Gln Val Asp Asp
    1010                1015                1020

Leu Ile Ala Lys Gly Asn Gly Lys Ile Thr Gln Asp Glu Leu Ser Lys
1025                1030                1035                1040

Val Val Asp Asn Tyr Glu Leu Leu Lys His Ser Lys Asn Val Thr Asn
                1045                1050                1055

Ser Leu Asp Lys Leu Ile Ser Ser Val Ser Ala Phe Thr Ser Ser Asn
            1060                1065                1070

Asp Ser Arg Asn Val Leu Val Ala Pro Thr Ser Met Leu Asp Gln Ser
        1075                1080                1085

Leu Ser Ser Leu Gln Phe Ala Arg Gly Ser
    1090                1095
```

(2) INFORMATION FOR SEQ ID NO:3:

(i) SEQUENCE CHARACTERISTICS:
(A) LENGTH: 3229 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 1..3207

(xi) SEQUENCE DESCRIPTION: SEQ ID NO:3:

```
ATG GCT ACT GTT ATA GAT CTA AGC TTC CCA AAA ACT GGG GCA AAA AAA       48
Met Ala Thr Val Ile Asp Leu Ser Phe Pro Lys Thr Gly Ala Lys Lys
  1               5                  10                  15

ATT ATC CTC TAT ATT CCC CAA AAT TAC CAA TAT GAT ACT GAA CAA GGT       96
Ile Ile Leu Tyr Ile Pro Gln Asn Tyr Gln Tyr Asp Thr Glu Gln Gly
             20                  25                  30

AAT GGT TTA CAG GAT TTA GTC AAA GCG GCC GAA GAG TTG GGG ATT GAG      144
Asn Gly Leu Gln Asp Leu Val Lys Ala Ala Glu Glu Leu Gly Ile Glu
         35                  40                  45

GTA CAA AGA GAA GAA CGC AAT AAT ATT GCA ACA GCT CAA ACC AGT TTA      192
Val Gln Arg Glu Glu Arg Asn Asn Ile Ala Thr Ala Gln Thr Ser Leu
     50                  55                  60

GGC ACG ATT CAA ACC GCT ATT GGC TTA ACT GAG CGT GGC ATT GTG TTA      240
```

-continued

```
Gly Thr Ile Gln Thr Ala Ile Gly Leu Thr Glu Arg Gly Ile Val Leu
 65                 70                  75                  80

TCC GCT CCA CAA ATT GAT AAA TTG CTA CAG AAA ACT AAA GCA GGC CAA       288
Ser Ala Pro Gln Ile Asp Lys Leu Leu Gln Lys Thr Lys Ala Gly Gln
                 85                  90                  95

GCA TTA GGT TCT GCC GAA AGC ATT GTA CAA AAT GCA AAT AAA GCC AAA       336
Ala Leu Gly Ser Ala Glu Ser Ile Val Gln Asn Ala Asn Lys Ala Lys
            100                 105                 110

ACT GTA TTA TCT GGC ATT CAA TCT ATT TTA GGC TCA GTA TTG GCT GGA       384
Thr Val Leu Ser Gly Ile Gln Ser Ile Leu Gly Ser Val Leu Ala Gly
        115                 120                 125

ATG GAT TTA GAT GAG GCC TTA CAG AAT AAC AGC AAC CAA CAT GCT CTT       432
Met Asp Leu Asp Glu Ala Leu Gln Asn Asn Ser Asn Gln His Ala Leu
    130                 135                 140

GCT AAA GCT GGC TTG GAG CTA ACA AAT TCA TTA ATT GAA AAT ATT GCT       480
Ala Lys Ala Gly Leu Glu Leu Thr Asn Ser Leu Ile Glu Asn Ile Ala
145                 150                 155                 160

AAT TCA GTA AAA ACA CTT GAC GAA TTT GGT GAG CAA ATT AGT CAA TTT       528
Asn Ser Val Lys Thr Leu Asp Glu Phe Gly Glu Gln Ile Ser Gln Phe
                165                 170                 175

GGT TCA AAA CTA CAA AAT ATC AAA GGC TTA GGG ACT TTA GGA GAC AAA       576
Gly Ser Lys Leu Gln Asn Ile Lys Gly Leu Gly Thr Leu Gly Asp Lys
            180                 185                 190

CTC AAA AAT ATC GGT GGA CTT GAT AAA GCT GGC CTT GGT TTA GAT GTT       624
Leu Lys Asn Ile Gly Gly Leu Asp Lys Ala Gly Leu Gly Leu Asp Val
        195                 200                 205

ATC TCA GGG CTA TTA TCG GGC GCA ACA GCT GCA CTT GTA CTT GCA GAT       672
Ile Ser Gly Leu Leu Ser Gly Ala Thr Ala Ala Leu Val Leu Ala Asp
    210                 215                 220

AAA AAT GCT TCA ACA GCT AAA AAA GTG GGT GCG GGT TTT GAA TTG GCA       720
Lys Asn Ala Ser Thr Ala Lys Lys Val Gly Ala Gly Phe Glu Leu Ala
225                 230                 235                 240

AAC CAA GTT GTT GGT AAT ATT ACC AAA GCC GTT TCT TCT TAC ATT TTA       768
Asn Gln Val Val Gly Asn Ile Thr Lys Ala Val Ser Ser Tyr Ile Leu
                245                 250                 255

GCC CAA CGT GTT GCA GCA GGT TTA TCT TCA ACT GGG CCT GTG GCT GCT       816
Ala Gln Arg Val Ala Ala Gly Leu Ser Ser Thr Gly Pro Val Ala Ala
            260                 265                 270

TTA ATT GCT TCT ACT GTT TCT CTT GCG ATT AGC CCA TTA GCA TTT GCC       864
Leu Ile Ala Ser Thr Val Ser Leu Ala Ile Ser Pro Leu Ala Phe Ala
        275                 280                 285

GGT ATT GCC GAT AAA TTT AAT CAT GCA AAA AGT TTA GAG AGT TAT GCC       912
Gly Ile Ala Asp Lys Phe Asn His Ala Lys Ser Leu Glu Ser Tyr Ala
    290                 295                 300

GAA CGC TTT AAA AAA TTA GGC TAT GAC GGA GAT AAT TTA TTA GCA GAA       960
Glu Arg Phe Lys Lys Leu Gly Tyr Asp Gly Asp Asn Leu Leu Ala Glu
305                 310                 315                 320

TAT CAG CGG GGA ACA GGG ACT ATT GAT GCA TCG GTT ACT GCA ATT AAT      1008
Tyr Gln Arg Gly Thr Gly Thr Ile Asp Ala Ser Val Thr Ala Ile Asn
                325                 330                 335

ACC GCA TTG GCC GCT ATT GCT GGT GGT GTG TCT GCT GCT GCA GCC GGC      1056
Thr Ala Leu Ala Ala Ile Ala Gly Gly Val Ser Ala Ala Ala Ala Gly
            340                 345                 350

TCG GTT ATT GCT TCA CCG ATT GCC TTA TTA GTA TCT GGG ATT ACC GGT      1104
Ser Val Ile Ala Ser Pro Ile Ala Leu Leu Val Ser Gly Ile Thr Gly
        355                 360                 365

GTA ATT TCT ACG ATT CTG CAA TAT TCT AAA CAA GCA ATG TTT GAG CAC      1152
Val Ile Ser Thr Ile Leu Gln Tyr Ser Lys Gln Ala Met Phe Glu His
    370                 375                 380
```

-continued

```
GTT GCA AAT AAA ATT CAT AAC AAA ATT GTA GAA TGG GAA AAA AAT AAT      1200
Val Ala Asn Lys Ile His Asn Lys Ile Val Glu Trp Glu Lys Asn Asn
385                 390                 395                 400

CAC GGT AAG AAC TAC TTT GAA AAT GGT TAC GAT GCC CGT TAT CTT GCG      1248
His Gly Lys Asn Tyr Phe Glu Asn Gly Tyr Asp Ala Arg Tyr Leu Ala
                405                 410                 415

AAT TTA CAA GAT AAT ATG AAA TTC TTA CTG AAC TTA AAC AAA GAG TTA      1296
Asn Leu Gln Asp Asn Met Lys Phe Leu Leu Asn Leu Asn Lys Glu Leu
            420                 425                 430

CAG GCA GAA CGT GTC ATC GCT ATT ACT CAG CAG CAA TGG GAT AAC AAC      1344
Gln Ala Glu Arg Val Ile Ala Ile Thr Gln Gln Gln Trp Asp Asn Asn
        435                 440                 445

ATT GGT GAT TTA GCT GGT ATT AGC CGT TTA GGT GAA AAA GTC CTT AGT      1392
Ile Gly Asp Leu Ala Gly Ile Ser Arg Leu Gly Glu Lys Val Leu Ser
    450                 455                 460

GGT AAA GCC TAT GTG GAT GCG TTT GAA GAA GGC AAA CAC ATT AAA GCC      1440
Gly Lys Ala Tyr Val Asp Ala Phe Glu Glu Gly Lys His Ile Lys Ala
465                 470                 475                 480

GAT AAA TTA GTA CAG TTG GAT TCG GCA AAC GGT ATT ATT GAT GTG AGT      1488
Asp Lys Leu Val Gln Leu Asp Ser Ala Asn Gly Ile Ile Asp Val Ser
                485                 490                 495

AAT TCG GGT AAA GCG AAA ACT CAG CAT ATC TTA TTC AGA ACG CCA TTA      1536
Asn Ser Gly Lys Ala Lys Thr Gln His Ile Leu Phe Arg Thr Pro Leu
            500                 505                 510

TTG ACG CCG GGA ACA GAG CAT CGT GAA CGC GTA CAA ACA GGT AAA TAT      1584
Leu Thr Pro Gly Thr Glu His Arg Glu Arg Val Gln Thr Gly Lys Tyr
        515                 520                 525

GAA TAT ATT ACC AAG CTC AAT ATT AAC CGT GTA GAT AGC TGG AAA ATT      1632
Glu Tyr Ile Thr Lys Leu Asn Ile Asn Arg Val Asp Ser Trp Lys Ile
    530                 535                 540

ACA GAT GGT GCA GCA AGT TCT ACC TTT GAT TTA ACT AAC GTT GTT CAG      1680
Thr Asp Gly Ala Ala Ser Ser Thr Phe Asp Leu Thr Asn Val Val Gln
545                 550                 555                 560

CGT ATT GGT ATT GAA TTA GAC AAT GCT GGA AAT GTA ACT AAA ACC AAA      1728
Arg Ile Gly Ile Glu Leu Asp Asn Ala Gly Asn Val Thr Lys Thr Lys
                565                 570                 575

GAA ACA AAA ATT ATT GCC AAA CTT GGT GAA GGT GAT GAC AAC GTA TTT      1776
Glu Thr Lys Ile Ile Ala Lys Leu Gly Glu Gly Asp Asp Asn Val Phe
            580                 585                 590

GTT GGT TCT GGT ACG ACG GAA ATT GAT GGC GGT GAA GGT TAC GAC CGA      1824
Val Gly Ser Gly Thr Thr Glu Ile Asp Gly Gly Glu Gly Tyr Asp Arg
        595                 600                 605

GTT CAC TAT AGC CGT GGA AAC TAT GGT GCT TTA ACT ATT GAT GCA ACC      1872
Val His Tyr Ser Arg Gly Asn Tyr Gly Ala Leu Thr Ile Asp Ala Thr
    610                 615                 620

AAA GAG ACC GAG CAA GGT AGT TAT ACC GTA AAT CGT TTC GTA GAA ACC      1920
Lys Glu Thr Glu Gln Gly Ser Tyr Thr Val Asn Arg Phe Val Glu Thr
625                 630                 635                 640

GGT AAA GCA CTA CAC GAA GTG ACT TCA ACC CAT ACC GCA TTA GTG GGC      1968
Gly Lys Ala Leu His Glu Val Thr Ser Thr His Thr Ala Leu Val Gly
                645                 650                 655

AAC CGT GAA GAA AAA ATA GAA TAT CGT CAT AGC AAT AAC CAG CAC CAT      2016
Asn Arg Glu Glu Lys Ile Glu Tyr Arg His Ser Asn Asn Gln His His
            660                 665                 670

GCC GGT TAT TAC ACC AAA GAT ACC TTG AAA GCT GTT GAA GAA ATT ATC      2064
Ala Gly Tyr Tyr Thr Lys Asp Thr Leu Lys Ala Val Glu Glu Ile Ile
        675                 680                 685

GGT ACA TCA CAT AAC GAT ATC TTT AAA GGT AGT AAG TTC AAT GAT GCC      2112
Gly Thr Ser His Asn Asp Ile Phe Lys Gly Ser Lys Phe Asn Asp Ala
    690                 695                 700
```

-continued

```
TTT AAC GGT GGT GAT GGT GTC GAT ACT ATT GAC GGT AAC GAC GGC AAT     2160
Phe Asn Gly Gly Asp Gly Val Asp Thr Ile Asp Gly Asn Asp Gly Asn
705                 710                 715                 720

GAC CGC TTA TTT GGT GGT AAA GGC GAT GAT ATT CTC GAT GGT GGA AAT     2208
Asp Arg Leu Phe Gly Gly Lys Gly Asp Asp Ile Leu Asp Gly Gly Asn
                725                 730                 735

GGT GAT GAT TTT ATC GAT GGC GGT AAA GGC AAC GAC CTA TTA CAC GGT     2256
Gly Asp Asp Phe Ile Asp Gly Gly Lys Gly Asn Asp Leu Leu His Gly
            740                 745                 750

GGC AAG GGC GAT GAT ATT TTC GTT CAC CGT AAA GGC GAT GGT AAT GAT     2304
Gly Lys Gly Asp Asp Ile Phe Val His Arg Lys Gly Asp Gly Asn Asp
        755                 760                 765

ATT ATT ACC GAT TCT GAC GGC AAT GAT AAA TTA TCA TTC TCT GAT TCG     2352
Ile Ile Thr Asp Ser Asp Gly Asn Asp Lys Leu Ser Phe Ser Asp Ser
    770                 775                 780

AAC TTA AAA GAT TTA ACA TTT GAA AAA GTT AAA CAT AAT CTT GTC ATC     2400
Asn Leu Lys Asp Leu Thr Phe Glu Lys Val Lys His Asn Leu Val Ile
785                 790                 795                 800

ACG AAT AGC AAA AAA GAG AAA GTG ACC ATT CAA AAC TGG TTC CGA GAG     2448
Thr Asn Ser Lys Lys Glu Lys Val Thr Ile Gln Asn Trp Phe Arg Glu
                805                 810                 815

GCT GAT TTT GCT AAA GAA GTG CCT AAT TAT AAA GCA ACT AAA GAT GAG     2496
Ala Asp Phe Ala Lys Glu Val Pro Asn Tyr Lys Ala Thr Lys Asp Glu
            820                 825                 830

AAA ATC GAA GAA ATC ATC GGT CAA AAT GGC GAG CGG ATC ACC TCA AAG     2544
Lys Ile Glu Glu Ile Ile Gly Gln Asn Gly Glu Arg Ile Thr Ser Lys
        835                 840                 845

CAA GTT GAT GAT CTT ATC GCA AAA GGT AAC GGC AAA ATT ACC CAA GAT     2592
Gln Val Asp Asp Leu Ile Ala Lys Gly Asn Gly Lys Ile Thr Gln Asp
    850                 855                 860

GAG CTA TCA AAA GTT GTT GAT AAC TAT GAA TTG CTC AAA CAT AGC AAA     2640
Glu Leu Ser Lys Val Val Asp Asn Tyr Glu Leu Leu Lys His Ser Lys
865                 870                 875                 880

AAT GTG ACA AAC AGC TTA GAT AAG TTA ATC TCA TCT GTA AGT GCA TTT     2688
Asn Val Thr Asn Ser Leu Asp Lys Leu Ile Ser Ser Val Ser Ala Phe
                885                 890                 895

ACC TCG TCT AAT GAT TCG AGA AAT GTA TTA GTG GCT CCA ACT TCA ATG     2736
Thr Ser Ser Asn Asp Ser Arg Asn Val Leu Val Ala Pro Thr Ser Met
            900                 905                 910

TTG GAT CAA AGT TTA TCT TCT CTT CAA TTT GCT AGG GGA TCC CAG GGC     2784
Leu Asp Gln Ser Leu Ser Ser Leu Gln Phe Ala Arg Gly Ser Gln Gly
        915                 920                 925

CAA TTT TTT AGA GAA ATA GAA AAC TTA AAG GAG TAT TTT AAT GCA AGT     2832
Gln Phe Phe Arg Glu Ile Glu Asn Leu Lys Glu Tyr Phe Asn Ala Ser
    930                 935                 940

AGC CCA GAT GTA GCT AAG GGT GGG CCT CTC TTC TCA GAA ATT TTG AAG     2880
Ser Pro Asp Val Ala Lys Gly Gly Pro Leu Phe Ser Glu Ile Leu Lys
945                 950                 955                 960

AAT TGG AAA GAT GAA AGT GAC AAA AAA ATT ATT CAG AGC CAA ATT GTC     2928
Asn Trp Lys Asp Glu Ser Asp Lys Lys Ile Ile Gln Ser Gln Ile Val
                965                 970                 975

TCC TTC TAC TTC AAA CTC TTT GAA AAC CTC AAA GAT AAC CAG GTC ATT     2976
Ser Phe Tyr Phe Lys Leu Phe Glu Asn Leu Lys Asp Asn Gln Val Ile
            980                 985                 990

CAA AGG AGC ATG GAT ATC ATC AAG CAA GAC ATG TTT CAG AAG TTC TTG     3024
Gln Arg Ser Met Asp Ile Ile Lys Gln Asp Met Phe Gln Lys Phe Leu
        995                 1000                1005

AAT GGC AGC TCT GAG AAA CTG GAG GAC TTC AAA AAG CTG ATT CAA ATT     3072
Asn Gly Ser Ser Glu Lys Leu Glu Asp Phe Lys Lys Leu Ile Gln Ile
```

-continued

```
    1010                1015                1020

CCG GTG GAT GAT CTG CAG ATC CAG CGC AAA GCC ATA AAT GAA CTC ATC      3120
Pro Val Asp Asp Leu Gln Ile Gln Arg Lys Ala Ile Asn Glu Leu Ile
1025                1030                1035                1040

AAA GTG ATG AAT GAC CTG TCA CCA AAA TCT AAC CTC AGA AAG CGG AAG      3168
Lys Val Met Asn Asp Leu Ser Pro Lys Ser Asn Leu Arg Lys Arg Lys
                1045                1050                1055

AGA AGT CAG AAT CTC TTT CGA GGC CGG AGA GCA TCA ACG TAATGGTCCT      3217
Arg Ser Gln Asn Leu Phe Arg Gly Arg Arg Ala Ser Thr
            1060                1065

CCTGCCTGCA AT                                                        3229
```

(2) INFORMATION FOR SEQ ID NO:4:

(i) SEQUENCE CHARACTERISTICS:
(A) LENGTH: 1069 amino acids
(B) TYPE: amino acid
(D) TOPOLOGY: linear (ii) MOLECULE TYPE: protein (xi) SEQUENCE DESCRIPTION: SEQ ID NO:4:

```
Met Ala Thr Val Ile Asp Leu Ser Phe Pro Lys Thr Gly Ala Lys Lys
  1               5                  10                  15

Ile Ile Leu Tyr Ile Pro Gln Asn Tyr Gln Tyr Asp Thr Glu Gln Gly
             20                  25                  30

Asn Gly Leu Gln Asp Leu Val Lys Ala Ala Glu Glu Leu Gly Ile Glu
         35                  40                  45

Val Gln Arg Glu Glu Arg Asn Asn Ile Ala Thr Ala Gln Thr Ser Leu
     50                  55                  60

Gly Thr Ile Gln Thr Ala Ile Gly Leu Thr Glu Arg Gly Ile Val Leu
 65                  70                  75                  80

Ser Ala Pro Gln Ile Asp Lys Leu Leu Gln Lys Thr Lys Ala Gly Gln
                 85                  90                  95

Ala Leu Gly Ser Ala Glu Ser Ile Val Gln Asn Ala Asn Lys Ala Lys
            100                 105                 110

Thr Val Leu Ser Gly Ile Gln Ser Ile Leu Gly Ser Val Leu Ala Gly
        115                 120                 125

Met Asp Leu Asp Glu Ala Leu Gln Asn Asn Ser Asn Gln His Ala Leu
    130                 135                 140

Ala Lys Ala Gly Leu Glu Leu Thr Asn Ser Leu Ile Glu Asn Ile Ala
145                 150                 155                 160

Asn Ser Val Lys Thr Leu Asp Glu Phe Gly Glu Gln Ile Ser Gln Phe
                165                 170                 175

Gly Ser Lys Leu Gln Asn Ile Lys Gly Leu Gly Thr Leu Gly Asp Lys
            180                 185                 190

Leu Lys Asn Ile Gly Gly Leu Asp Lys Ala Gly Leu Gly Leu Asp Val
        195                 200                 205

Ile Ser Gly Leu Leu Ser Gly Ala Thr Ala Ala Leu Val Leu Ala Asp
    210                 215                 220

Lys Asn Ala Ser Thr Ala Lys Lys Val Gly Ala Gly Phe Glu Leu Ala
225                 230                 235                 240

Asn Gln Val Val Gly Asn Ile Thr Lys Ala Val Ser Ser Tyr Ile Leu
                245                 250                 255

Ala Gln Arg Val Ala Ala Gly Leu Ser Ser Thr Gly Pro Val Ala Ala
            260                 265                 270
```

-continued

```
Leu Ile Ala Ser Thr Val Ser Leu Ala Ile Ser Pro Leu Ala Phe Ala
        275                 280                 285

Gly Ile Ala Asp Lys Phe Asn His Ala Lys Ser Leu Glu Ser Tyr Ala
    290                 295                 300

Glu Arg Phe Lys Lys Leu Gly Tyr Asp Gly Asp Asn Leu Leu Ala Glu
305                 310                 315                 320

Tyr Gln Arg Gly Thr Gly Thr Ile Asp Ala Ser Val Thr Ala Ile Asn
                325                 330                 335

Thr Ala Leu Ala Ala Ile Ala Gly Gly Val Ser Ala Ala Ala Ala Gly
            340                 345                 350

Ser Val Ile Ala Ser Pro Ile Ala Leu Leu Val Ser Gly Ile Thr Gly
        355                 360                 365

Val Ile Ser Thr Ile Leu Gln Tyr Ser Lys Gln Ala Met Phe Glu His
    370                 375                 380

Val Ala Asn Lys Ile His Asn Lys Ile Val Glu Trp Glu Lys Asn Asn
385                 390                 395                 400

His Gly Lys Asn Tyr Phe Glu Asn Gly Tyr Asp Ala Arg Tyr Leu Ala
                405                 410                 415

Asn Leu Gln Asp Asn Met Lys Phe Leu Leu Asn Leu Asn Lys Glu Leu
            420                 425                 430

Gln Ala Glu Arg Val Ile Ala Ile Thr Gln Gln Gln Trp Asp Asn Asn
        435                 440                 445

Ile Gly Asp Leu Ala Gly Ile Ser Arg Leu Gly Glu Lys Val Leu Ser
    450                 455                 460

Gly Lys Ala Tyr Val Asp Ala Phe Glu Glu Gly Lys His Ile Lys Ala
465                 470                 475                 480

Asp Lys Leu Val Gln Leu Asp Ser Ala Asn Gly Ile Ile Asp Val Ser
                485                 490                 495

Asn Ser Gly Lys Ala Lys Thr Gln His Ile Leu Phe Arg Thr Pro Leu
            500                 505                 510

Leu Thr Pro Gly Thr Glu His Arg Glu Arg Val Gln Thr Gly Lys Tyr
        515                 520                 525

Glu Tyr Ile Thr Lys Leu Asn Ile Asn Arg Val Asp Ser Trp Lys Ile
    530                 535                 540

Thr Asp Gly Ala Ala Ser Ser Thr Phe Asp Leu Thr Asn Val Val Gln
545                 550                 555                 560

Arg Ile Gly Ile Glu Leu Asp Asn Ala Gly Asn Val Thr Lys Thr Lys
                565                 570                 575

Glu Thr Lys Ile Ile Ala Lys Leu Gly Glu Gly Asp Asp Asn Val Phe
            580                 585                 590

Val Gly Ser Gly Thr Thr Glu Ile Asp Gly Gly Glu Gly Tyr Asp Arg
        595                 600                 605

Val His Tyr Ser Arg Gly Asn Tyr Gly Ala Leu Thr Ile Asp Ala Thr
    610                 615                 620

Lys Glu Thr Glu Gln Gly Ser Tyr Thr Val Asn Arg Phe Val Glu Thr
625                 630                 635                 640

Gly Lys Ala Leu His Glu Val Thr Ser Thr His Thr Ala Leu Val Gly
                645                 650                 655

Asn Arg Glu Glu Lys Ile Glu Tyr Arg His Ser Asn Asn Gln His His
            660                 665                 670

Ala Gly Tyr Tyr Thr Lys Asp Thr Leu Lys Ala Val Glu Glu Ile Ile
        675                 680                 685

Gly Thr Ser His Asn Asp Ile Phe Lys Gly Ser Lys Phe Asn Asp Ala
```

-continued

```
    690                 695                 700

Phe Asn Gly Gly Asp Gly Val Asp Thr Ile Asp Gly Asn Asp Gly Asn
705                 710                 715                 720

Asp Arg Leu Phe Gly Gly Lys Gly Asp Asp Ile Leu Asp Gly Gly Asn
                725                 730                 735

Gly Asp Asp Phe Ile Asp Gly Gly Lys Gly Asn Asp Leu Leu His Gly
            740                 745                 750

Gly Lys Gly Asp Asp Ile Phe Val His Arg Lys Gly Asp Gly Asn Asp
        755                 760                 765

Ile Ile Thr Asp Ser Asp Gly Asn Asp Lys Leu Ser Phe Ser Asp Ser
    770                 775                 780

Asn Leu Lys Asp Leu Thr Phe Glu Lys Val Lys His Asn Leu Val Ile
785                 790                 795                 800

Thr Asn Ser Lys Lys Glu Lys Val Thr Ile Gln Asn Trp Phe Arg Glu
                805                 810                 815

Ala Asp Phe Ala Lys Glu Val Pro Asn Tyr Lys Ala Thr Lys Asp Glu
            820                 825                 830

Lys Ile Glu Glu Ile Ile Gly Gln Asn Gly Glu Arg Ile Thr Ser Lys
        835                 840                 845

Gln Val Asp Asp Leu Ile Ala Lys Gly Asn Gly Lys Ile Thr Gln Asp
    850                 855                 860

Glu Leu Ser Lys Val Val Asp Asn Tyr Glu Leu Leu Lys His Ser Lys
865                 870                 875                 880

Asn Val Thr Asn Ser Leu Asp Lys Leu Ile Ser Ser Val Ser Ala Phe
                885                 890                 895

Thr Ser Ser Asn Asp Ser Arg Asn Val Leu Val Ala Pro Thr Ser Met
            900                 905                 910

Leu Asp Gln Ser Leu Ser Ser Leu Gln Phe Ala Arg Gly Ser Gln Gly
        915                 920                 925

Gln Phe Phe Arg Glu Ile Glu Asn Leu Lys Glu Tyr Phe Asn Ala Ser
    930                 935                 940

Ser Pro Asp Val Ala Lys Gly Gly Pro Leu Phe Ser Glu Ile Leu Lys
945                 950                 955                 960

Asn Trp Lys Asp Glu Ser Asp Lys Lys Ile Ile Gln Ser Gln Ile Val
                965                 970                 975

Ser Phe Tyr Phe Lys Leu Phe Glu Asn Leu Lys Asp Asn Gln Val Ile
            980                 985                 990

Gln Arg Ser Met Asp Ile Ile Lys Gln Asp Met Phe Gln Lys Phe Leu
        995                 1000                1005

Asn Gly Ser Ser Glu Lys Leu Glu Asp Phe Lys Lys Leu Ile Gln Ile
    1010                1015                1020

Pro Val Asp Asp Leu Gln Ile Gln Arg Lys Ala Ile Asn Glu Leu Ile
1025                1030                1035                1040

Lys Val Met Asn Asp Leu Ser Pro Lys Ser Asn Leu Arg Lys Arg Lys
                1045                1050                1055

Arg Ser Gln Asn Leu Phe Arg Gly Arg Arg Ala Ser Thr
            1060                1065
```

(2) INFORMATION FOR SEQ ID NO:5:

(i) SEQUENCE CHARACTERISTICS:
(A) LENGTH: 6 amino acids
(B) TYPE: amino acid
(C) STRANDEDNESS: single
(D) TOPOLOGY: linear -continued

```
    (ii) MOLECULE TYPE: peptide

    (ix) FEATURE:
          (A) NAME/KEY: Modified-site
          (B) LOCATION: 3
          (D) OTHER INFORMATION: /note= "X is Lys, Asp, Val or Asn."

    (ix) FEATURE:
          (A) NAME/KEY: Modified-site
          (B) LOCATION: 5
          (D) OTHER INFORMATION: /note= "X is Asn or Asp."

    (xi) SEQUENCE DESCRIPTION: SEQ ID NO:5:

Gly Gly Xaa Gly Xaa Asp
1               5


(2) INFORMATION FOR SEQ ID NO:6:

     (i) SEQUENCE CHARACTERISTICS:
          (A) LENGTH: 20 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO:6:

Gly Gly Asn Gly Asp Asp Phe Ile Asp Gly Gly Lys Gly Asn Asp Leu
1               5                   10                  15

Leu His Gly Gly
            20
```

VACCINES WITH CHIMERIC PROTEIN COMPRISING GAMMA-INTERFERON AND LEUKOTOXIN DERIVED FROM PASTEURELLA HAEMOLYTICA

CROSS-REFERENCE TO RELATED APPLICATION

This application is a continuation of application Ser. No. 08/681,479 filed on Jul. 22, 1996 now abandoned, which is a divisional of Ser. No. 08/170,126 filed on Dec. 20, 1993 now U.S. Pat. No. 5,594,107, which is a continuation-in-part of Ser. No. 07/777,715 filed on Oct. 16, 1991 (now U.S. Pat. No. 5,273,889) which is a continuation-in-part of Ser. No. 07/571,301 filed on Aug. 22, 1990 (now U.S. Pat. No. 5,238,823).

DESCRIPTION

TECHNICAL FIELD

The present invention relates generally to subunit antigens, vaccine compositions, and methods of administering the same. More particularly, the present invention relates to cytokine-cytotoxin gene fusion products and the use of the same for stimulating immunity against pneumonia.

BACKGROUND OF THE INVENTION

Respiratory disease affecting feedlot cattle causes tremendous losses yearly to the cattle industry. Calves are the most severely affected, and a large number of these calves die. This disease is associated with pathogenic microorganisms, particularly Pasteurallae species, and various stresses, such as transportation and overcrowding.

Shipping fever is the most economically important respiratory disease associated with Pasteurella species. The disease is characterized by sudden onset, usually within two weeks of stress. The symptoms include dyspnea, cough, ocular and nasal discharge, inappetence and rapid weight loss, fever, increased lung sounds, immunosuppression, general depression, viral and/or bacterial infection of the lungs. Various bacteria and viruses have been isolated from affected animals including Pasteurella spp., bovine herpes virus 1, parainfluenza-3 virus, bovine-respiratory syncytial virus and Mycoplasma species. The disease typically affects 15–30% of exposed animals and the resulting deaths are typically 2–5% of the exposed population.

Exposure of the animal to stress, plus infection with a variety of viruses, as described above, appears to make the animal susceptible to fibrinous pneumonia caused by *P. haemolytica*, and to a lesser extent, *P. multocida*. For a general background on shipping fever see Yates, W. D. G. (1982) *Can. J. Comp. Med.* 46:225–263.

*P. haemolytica* also causes enzootic pneumonia and can infect a wide range of animals, in addition to cattle, including economically important species such as sheep, swine, horses and fowl. *P. haemolytica* is also frequently found in the upper respiratory tract of healthy animals. Pneumonia develops when the bacteria infect the lungs of these animals. Protection against Pasteurella-associated diseases is therefore economically important to the agricultural industry.

There are two known biotypes of *P. haemolytica* designated A and T. There are also 12 recognized serotypes which have been isolated from ruminants. Biotype A, serotype 1 (referred to hereinafter as "A1") predominates in bovine pneumonia in North America. Shewen, P. E., and Wilkie, B. N. (1983) *Am. J. Vet. Res.* 44:715–719. However, antigens isolated from different serotypes appear to be somewhat cross-reactive. See, e.g., Donanchie et al. (1984) *J. Gen. Micro.* 130:1209–1216.

Previous Pasteurellosis vaccines have utilized whole cell preparations of either live or heat killed bacteria of various serotypes as described in U.S. Pat. Nos. 4,328,210, 4,171,354, 3,328,252, 4,167,560 and 4,346,074. Traditional vaccine preparations, however, have not been effective in protecting against Pasteurella infections. Indeed, vaccinated animals are frequently more susceptible to the disease than their non-vaccinated counterparts. Martin et al. (1980) *Can. J. Comp. Med.* 44:1–10. The lack of protection offered by traditional vaccines is probably due to the absence of important antigens, virulence determinants, or the presence of immunosuppressive components in the preparations.

Other vaccine preparations have included crude supernatant extracts from *P. haemolytica*. See, e.g., Shewen, P. E., and Wilkie, B. N. (1988) in *Can. J. Vet. Res.* 52:30–36. These culture supernatants, however, contain various soluble surface antigens of the bacterium and produce variable results when administered to animals. Other preparations include capsular extracts obtained via sodium salicylate extraction (see, e.g., Donanchie et al. (1984) 130:1209–1216; U.S. Pat. No. 4,346,074), saline extracted antigens (see, e.g., Lessley et al. (1985) *Veterinary Immunology and Immunopathology* 10:279–296; Himmel et al. (1982) *Am. J. Vet. Res.* 43:764–767), and modified live Pasteurella mutants.

Still other attempts at immunization have included the use of a purified cytotoxin from *P. haemolytica*. See, e.g. Gentry et al. (1985) *Vet. Immunology and Immunopathology* 9:239–250. This cytotoxin, which is a leukotoxin, is secreted by actively growing bacteria. Shewen, P. E., and Wilkie, B. N. (1987) *Infect. Immun.* 55:3233–3236. The gene encoding this leukotoxin has been cloned and expressed in bacterial cells. Lo et al. (1985) *Infect. Immun.* 50:667–671. Calves which survive *P. haemolytica* infections possess toxin-neutralizing antibody. Cho, H. J., and Jericho, K. W. F. (1986) *Can. J. Vet. Res.* 50:27–31; Cho et al. (1984) *Can. J. Comp. Med.* 48:151–155.

Cytokines are a group of hormone-like mediators produced by leukocytes. Cytokines serve as endogenous signals that act in conjunction with antigens to amplify both localized and systemic host defense mechanisms involving macrophages, lymphocytes, and other cell types. Representative lympokines include interleukin-1 (IL1), interleukin-2 (IL2), interleukin-3 (IL3), interleukin-4 (IL4), and gamma-interferon (γIFN).

IL1 and IL2 both exhibit thymocyte mitogenic activity and IL2 stimulates T lymphocyte proliferation. IL3 stimulates the growth of hematopoietic progenitor cells and multipotential stem cells, and IL4 acts as an induction factor on resting B cells and as a B cell growth and differentiation factor. IL4 also exhibits T cell stimulatory activity.

γIFN is predominantly produced by antigen- or mitogen-stimulated T lymphocytes. γIFN has been shown to be a potent immunomodulator and appears to enhance natural killer cell activity, antibody-dependent cellular cytotoxicity, and cytotoxic T lymphocyte activity (Lawman et al. (1989) "Recombinant Cytokines and their Potential Therapeutic Value in Veterinary Medicine" in *Comprehensive Biotech, First Supplement, Animal Biotechnology*, Pages 63–106 (Pergamon Press, London).

Gene fusions provide a convenient method for the production of chimeric proteins. The expression of a chimeric protein, such as a cytokine linked to an antigenic polypeptide, allows the simultaneous delivery of both agents to a desired recipient. PCT Publication No. WO 88/00971 (publication date of Feb. 11, 1988) describes the fusion of an IL2 gene with the influenza hemagglutinin coding sequence and the subsequent administration of the fusion protein using a viral vector. The application nowhere contemplates the use of a cytokine fused to leukotoxin for the treatment of pneumonia in animals.

DISCLOSURE OF THE INVENTION

The present invention is based on the construction of novel gene fusions between sequences encoding certain cytokines and sequences encoding a cytotoxin derived from the RTX family of toxins, such as the *P. haemolytica* leukotoxin gene. These constructs produce fusion proteins that can be used to protect cattle and other animals from a number of diseases, depending on the particular fusion, including but not limited to respiratory diseases such as pneumonia, including shipping fever pneumonia.

In one embodiment, the present invention is directed to a DNA construct comprising a first nucleotide sequence encoding a cytokine, or an active fragment thereof, operably linked to a second nucleotide sequence encoding at least one epitope of an RTX cytotoxin. In particularly preferred embodiments, the first nucleotide sequence encodes IL2 or γIFN, or active fragments thereof and the second nucleotide sequence encodes a leukotoxin.

In another embodiment, the subject invention is directed to expression cassettes comprised of (a) the DNA constructs above and (b) control sequences that direct the transcription of the constructs whereby the constructs can be transcribed and translated in a host cell.

In yet another embodiment, the invention is directed to host cells transformed with these expression cassettes.

Another embodiment of the invention provides a method of producing a recombinant polypeptide comprising (a) providing a population of host cells described above and (b) growing the population of cells under conditions whereby the polypeptide encoded by the expression cassette is expressed.

In still another embodiment, the invention is directed to an immunogenic chimeric protein comprising a cytokine, or an active fragment thereof, linked to at least one epitope of an RTX cytotoxin. In particularly preferred embodiments, the cytokine is derived from bovine IL2 or bovine γIFN and the RTX cytotoxin is a leukotoxin.

Also disclosed are vaccine compositions comprising the chimeric proteins and a pharmaceutically acceptable vehicle and methods of vaccinating a subject using the same.

These and other embodiments of the present invention will readily occur to those of ordinary skill in the art in view of the disclosure herein.

BRIEF DESCRIPTION OF THE FIGURES

FIGS. 3A–3K (SEQ ID NOS:1–2) show the nucleotide sequence and predicted amino acid sequence of the bovine IL2-LKT chimeric protein from pAA356.

FIG. 4A shows the changes in IgG anti-LKT in nonimmunized calves; FIG. 4B shows the changes in IgG anti-LKT in LKT-immunized calves; and FIG. 4C shows the changes in IgG anti-LKT in calves immunized with an IL2-LKT fusion protein.

FIGS. 7A–7L (SEQ ID NOS:3–4) depict the nucleotide sequence and predicted amino acid sequence of the bovine γIFN-LKT chimeric protein from pAA497.

DETAILED DESCRIPTION

Figure 1:
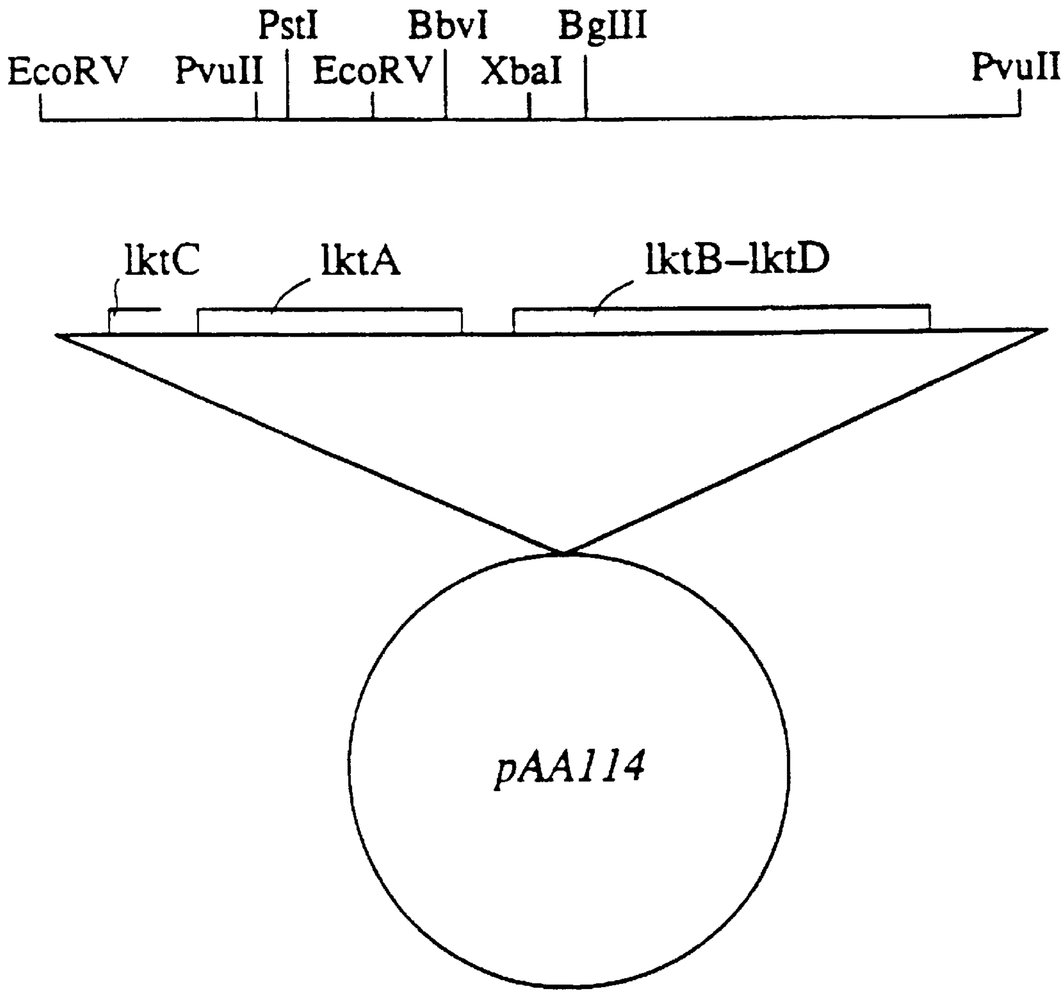
FIG. 1 depicts the structure of the leukotoxin gene of *P. haemolytica* as found in plasmid pAA114.

The practice of the present invention will employ, unless otherwise indicated, conventional techniques of molecular biology, microbiology, virology, recombinant DNA technology, and immunology, which are within the skill of the art. Such techniques are explained fully in the literature. See, e.g., Sambrook, Fritsch & Maniatis, *Molecular Cloning: A Laboratory Manual*, Second Edition (1989); Maniatis, Fritsch & Sambrook, *Molecular Cloning: A Laboratory Manual* (1982); *DNA Cloning*, Vols. I and II (D. N. Glover ed. 1985); *Oligonucleotide Synthesis* (M. J. Gait ed. 1984); *Nucleic Acid Hybridization* (B. D. Hames & S. J. Higgins eds. 1984); *Animal Cell Culture* (R. K. Freshney ed. 1986); *Immobilized Cells and Enzymes* (IRL press, 1986); B. Perbal, *A Practical Guide to Molecular Cloning* (1984); the series, *Methods In Enzymology* (S. Colowick and N. Kaplan eds., Academic Press, Inc.); and *Handbook of Experimental Immunology*, Vols. I–IV (D. M. Weir and C. C. Blackwell eds., 1986, Blackwell Scientific Publications).

All patents, patent applications, and publications mentioned herein, whether supra or infra, are hereby incorporated by reference in their entirety.

A. Definitions

In describing the present invention, the following terms will be employed, and are intended to be defined as indicated below.

By "cytokine" is meant any one of the group of hormone-like mediators produced by T and B lymphocytes. Representative cytokines include but are not limited to IL1, IL2, IL3, IL4 and γIFN. An "active" fragment of a cytokine is a fragment of a cytokine which retains activity as determined using standard in vitro and in vivo assays. For example, assays for determining IL2 and γIFN activity are described in the Examples. See also Campos, M. (1989) *Cell. Immun.* 120:259–269 and Czarniecki, C. W. (1986) *J. Interferon Res.* 6:29–37. Assays for determining the activity of other cytokines are known and can readily be conducted by those having ordinary skill in the art.

The term "RTX cytotoxin" intends a cytotoxin belonging to the family of cytolytic toxins known as the RTX proteins. The toxins are characterized by a series of repeated amino acid domains near the carboxy terminus. The consensus amino acid sequence is Gly-Gly-X-Gly-(Asn/Asp)-Asp (SEQ ID NO:5), where X is Lys, Asp, Val or Asn. Such proteins include, among others, leukotoxins derived from Pasteurella and Actinobacillus, such as those found in *P. haemolytica, Actinobacillus pleuropneumoniae, A. actinomycetemcomitans, A. suis*, as well as the cytotoxins found in *Proteus vulgaris, Morganella morganii, Moraxella bovis, Neisseria meningitidis, H. influenzae* type B, *E. coli* alpha hemolysin and *Bordetella pertussis* adenylate cyclase hemolysin. (For further descriptions of these toxins, see, e.g., Strathdee, C. A., and Lo, R. Y. C. (1987) *Infect. Immun.* 55:3233–3236; Lo, R. Y. C. (1990) *Can. J. Vet. Res.* 54:S33–S35; Welch, R. A. (1991) *Mol. Microbiol.* 5:521–528); Lo et al. (1987) *Infect. Immun.* 55:1987–1996; Glaser et al. (1988) *Molec. Microbiol.* 2:19–30; Lally et al. (1989) *J. Biol. Chem.* 254:15451–15456; Kolodrubetz et al. (1989) *Infect. Immun.* 57:1465–1469; Chang et al. (1989) *DNA* 8:635–647; Frey, J. and Nicolet, J. (1988) *Infect. Immun.* 56:2570–2575; Devenish et al. (1989) *Infect. Immun.* 57:3210–3213; Koronakis et al. (1987) *J. Bacteriol.* 169:1509–1515 and Highlander et al. (1989) *DNA* 8:15–28). The desired cytotoxin may be chemically synthesized, isolated from an organism expressing the same, or recombinantly produced.

Furthermore, the term intends an immunogenic protein having an amino acid sequence substantially homologous to a contiguous amino acid sequence found in the particular native cytotoxin molecule. Thus, the term includes both full-length and partial sequences, as well as analogs. Although the native full-length cytotoxins described above display cytolytic activity, the term "cytotoxin" also intends molecules which remain immunogenic yet lack the cytotoxic character of the native toxins. Thus, for example, with respect to the leukotoxins described above, molecules which lack leukotoxic activity yet remain immunogenic, would be captured by the term "leukotoxin." Such a molecule is present in plasmid pAA356, described further below. The nucleotide sequences and corresponding amino acid sequences for several leukotoxins are known. See, e.g., U.S. Pat. Nos. 4,957,739 and 5,055,400; Lo et al. (1985) *Infect. Immun.* 50:667–67; Lo et al. (1987) *Infect. Immun.* 55:1987–1996; Strathdee, C. A., and Lo, R. Y. C. (1987) *Infect. Immun.* 55:3233–3236; Highlander et al. (1989) *DNA* 8:15–28; Welch, R. A. (1991) *Mol. Microbiol.* 5:521–528.

An "antigen" refers to a molecule containing one or more epitopes that will stimulate a host's immune system to make a humoral and/or cellular antigen-specific response. The term is also used interchangeably with "immunogen."

The term "epitope" refers to the site on an antigen or hapten to which a specific antibody molecule binds. The term is also used interchangeably with "antigenic determinant" or "antigenic determinant site." One such epitope is the consensus sequence found among the RTX family of toxins described above. This sequence is Gly-Gly-X-Gly-(Asn/Asp)-Asp (SEQ ID NO:5), where X is preferably Lys, Asp, Val or Asn. Other substitutions for X in the consensus sequence are also contemplated including substitutions with an aliphatic amino acid, such as Gly, Ala, Val, Leu, Ile, a charged amino acid such as Asp, Glu, Arg, His or Lys, or a corresponding neutral amino acid such as Asn or Gln.

An "immunological response" to a composition or vaccine is the development in the host of a cellular and/or antibody-mediated immune response to the composition or vaccine of interest. Usually, such a response includes but is not limited to one or more of the following effects; the production of antibodies, B cells, helper T cells, suppressor T cells, and/or cytotoxic T cells and/or $\gamma\delta$ T cells, directed specifically to an antigen or antigens included in the composition or vaccine of interest.

The terms "immunogenic" protein, polypeptide or amino acid sequence refer to an amino acid sequence which elicits an immunological response as described above. An "immunogenic" protein, polypeptide-or amino acid sequence, as used herein, includes the full-length (or near full-length) sequence of the protein in question, analogs thereof, or immunogenic fragments thereof. By "immunogenic fragment" is meant a fragment of a polypeptide which includes one or more epitopes and thus elicits the immunological response described above. Such fragments will usually be at least about 2 amino acids in length, more preferably about 5 amino acids in length, and most preferably at least about 10 to 15 amino acids in length. There is no critical upper limit to the length of the fragment, which could comprise nearly the full-length of the protein sequence, or even a fusion protein comprising two or more epitopes of the protein.

The term "protein" is used herein to designate a naturally occurring polypeptide. The term "polypeptide" is used in its broadest sense, i.e., any polymer of amino acids (dipeptide or greater) linked through peptide bonds. Thus, the term "polypeptide" includes proteins, oligopeptides, protein fragments, analogs, muteins, fusion proteins and the like.

"Native" proteins or polypeptides refer to proteins or polypeptides recovered from a source occurring in nature. Thus, the term "native leukotoxin" would include naturally occurring leukotoxin and fragments thereof.

"Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

A "rotavirus VP6 protein" refers to the art-recognized major viral protein of the inner capsid from any species or strain within the family Reoviridae. See, e.g., Kapikian et al., 1985. Examples of rotavirus strains from which the VP6 protein can be isolated and employed in the present invention include, but are not limited to, Simian SA-11, human D rotavirus, bovine UK rotavirus, human Wa or W rotavirus, human DS-1 rotavirus, rhesus rotavirus, the "O" agent, bovine NCDV rotavirus, human S2 rotavirus, human KUN rotavirus, human 390 rotavirus, human P rotavirus, human M rotavirus, human Walk 57/14 rotavirus, human Mo rotavirus, human Ito rotavirus, human Nemoto rotavirus, human YO rotavirus, human McM2 rotavirus, rhesus monkey MMU18006 rotavirus, canine CU-1 rotavirus, feline Taka rotavirus, equine H-2 rotavirus, human St. Thomas No. 3 and No. 4 rotaviruses, human Hosokawa rotavirus, human Hochi rotavirus, porcine SB-2 rotavirus, porcine Gottfried rotavirus, porcine SB-1A rotavirus, porcine OSU rotavirus, equine H-1 rotavirus, chicken Ch.2 rotavirus, turkey Ty.1 rotavirus, bovine C486 rotavirus, and strains derived from them. Thus the present invention encompasses the use of VP6 from any rotavirus strain, whether from subgroup I, subgroup II, or any as yet unidentified subgroup, as well as from any of the serotypes 1–7, as well as any as yet unidentified serotypes. Such VP6 proteins can be used as immunologic carriers of polypeptides. These carrier molecules comprise amino acid sequences of rotavirus VP6 amino acid sequences which are unique to the class, or any member of the class, of VP6 polypeptides. Such unique sequences of VP6 proteins are referred to as a "rotavirus VP6 inner capsid protein amino acid sequence."

A carrier that is "substantially homologous to a rotavirus VP6 inner capsid protein or a functional fragment thereof" is one in which at least about 85%, preferably at least about 90%, and most preferably at least about 95%, of the amino acids match over a defined length of the molecule. A "functional fragment" of a rotavirus VP6 inner capsid protein is a fragment with the capability of acting as a carrier molecule for the novel chimeric proteins of the instant invention.

A DNA "coding sequence" or a "nucleotide sequence encoding" a particular protein, is a DNA sequence which is transcribed and translated into a polypeptide in a host cell when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A transcription termination sequence will usually be located 3' to the coding sequence.

A "promoter sequence" is a DNA regulatory region capable of binding RNA polymerase in a cell and initiating transcription of a downstream (3' direction) coding sequence. For purposes of defining the present invention, the promoter sequence is bound at the 3' terminus by the translation start codon (ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eucaryotic promoters will often, but not always, contain "TATA" boxes and "CAT" boxes. Procaryotic promoters contain Shine-Dalgarno sequences in addition to the −10 and −35 consensus sequences.

DNA "control sequences" refer collectively to promoter sequences, ribosome binding sites, polyadenylation signals, transcription termination sequences, upstream regulatory domains, enhancers, and the like, which collectively provide for the transcription and translation of a coding sequence in a host cell.

A coding sequence is "operably linked to" another coding sequence when RNA polymerase will transcribe the two coding sequences into MRNA, which is then translated into a chimeric polypeptide encoded by the two coding sequences. The coding sequences need not be contiguous to one another so long as the transcribed sequence is ultimately processed to produce the desired chimeric protein.

A control sequence "directs the transcription" of a coding sequence in a cell when RNA polymerase will bind the promoter sequence and transcribe the coding sequence into mRNA, which is then translated into the polypeptide encoded by the coding sequence.

A "host cell" is a cell which has been transformed, or is capable of transformation, by an exogenous DNA sequence.

A cell has been "transformed" by exogenous DNA when such exogenous DNA has been introduced inside the cell membrane. Exogenous DNA may or may not be integrated (covalently linked) to chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cell containing the exogenous DNA.

Two DNA or polypeptide sequences are "substantially homologous" when at least about 80% (preferably at least about 90%, and most preferably at least about 95%) of the nucleotides or amino acids match over a defined length of the molecule. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, vols I & II, supra; *Nucleic Acid Hybridization*, supra. A "substantially homologous" sequence also intends a sequence that encodes a protein which is functionally equivalent to the depicted sequences. By "functionally equivalent" is meant that the amino acid sequence of the subject fusion protein is one that will elicit an immunological response, as defined above, equivalent to the response elicited by the unmodified chimeric protein.

A "heterologous" region of a DNA construct is an identifiable segment of DNA within or attached to another DNA molecule that is not found in association with the other molecule in nature. Thus, when the heterologous region encodes a bacterial gene, the gene will usually be flanked by DNA that does not flank the bacterial gene in the genome of the source bacteria. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

A composition containing A is "substantially free of" B when at least about 85% by weight of the total of A+B in the composition is A. Preferably, A comprises at least about 90% by weight of the total of A+B in the composition, more preferably at least about 95%, or even 99% by weight.

The term "treatment" as used herein refers to either (i) the prevention of infection or reinfection (prophylaxis), or (ii) the reduction or elimination of symptoms or the disease of interest (therapy).

B. General Methods

Central to the instant invention is the production of a chimeric protein comprising a cytokine and a cytotoxin belonging to the RTX family of proteins, preferably leukotoxin. This chimeric protein can be used in a vaccine composition to protect animals against a variety of diseases, including respiratory diseases such as pneumonia, including shipping fever pneumonia.

As explained above, cytotoxins contemplated for use in the instant chimeric proteins include any of the various toxins derived from the RTX family of molecules. It is to be understood that modifications of the native amino acid sequence of these toxins which result in proteins which have substantially equivalent or enhanced activity as compared to the native sequences, are also contemplated. These modifications may be deliberate, as through site-directed mutagenesis, or may be accidental, such as through mutation of hosts which produce the cytotoxins. All of these modifications are included, so long as immunogenic activity is retained. Additionally, both full-length cytotoxins, immunogenic fragments thereof, and fusion proteins comprising the same, are intended for use in the subject vaccines.

Particularly useful in the subject chimeric proteins are leukotoxins, and in particular, leukotoxin derived from *P. haemolytica*. The sequence of the various full-length RTX leukotoxins are known and have been described (see, e.g., U.S. Pat. Nos. 4,957,739 and 5,055,400; Lo et al. (1985) *Infect. Immun.* 50:667–67; Lo et al. (1987) *Infect. Immun.* 55:1987–1996; Strathdee, C. A., and Lo, R. Y. C. (1987)

*Infect. Immun.* 55:3233–3236; Highlander et al. (1989) *DNA* 8:15–28; Welch, R. A. (1991) *Mol. Microbiol.* 5:521–528. However, useful leukotoxins include both full-length and truncated forms of the molecule which eliminate the cytotoxic activity thereof. For example, the truncated leukotoxin, LKT 352, derived from the lktA gene present in plasmid pAA352 (ATCC Accession No. 68283), and found in plasmid pAA497 (described further below), will find use in the present chimeras. The cloning strategy for this leukotoxin is described in the examples herein as well as in International Publication No. W091/15237. LKT 352 is a leukotoxin having 931 amino acids, which lacks the cytotoxic portion of the molecule. of course, the gene encoding LKT 352 need not be physically derived from the sequence present in plasmid pAA352. Rather, it may be generated in any manner, including for example, by chemical synthesis or recombinant production. In addition, sequence variations may be present so long as the protein is immunogenic.

Similarly, the coding sequences for numerous cytokines have been elucidated. See, e.g., published EPA 088,622 and EPA 230,119 (both describing sequences for bovine γIFN); Maliszewski et al. (1988) *Molec. Immun.* 25:429–437 and Ceretti et al. (1986) *Proc. Natl. Acad. Sci.*, U.S.A. 83:2332–2337. Again, these cytokines can be purified using standard techniques.

Purification of the above proteins permits the sequencing of the same by any of the various methods known to those skilled in the art. For example, the amino acid sequences of the subject proteins can be determined from the purified proteins by repetitive cycles of Edman degradation, followed by amino acid analysis by HPLC. Other methods of amino acid sequencing are also known in the art. Furthermore, fragments of the proteins can be tested for biological activity and active fragments used in compositions in lieu of the entire protein.

Once the amino acid sequences are determined, oligonucleotide probes which contain the codons for a portion of the determined amino acid sequences can be prepared and used to screen DNA libraries for genes encoding the subject proteins or for analogous genes in related species. The basic strategies for preparing oligonucleotide probes and DNA libraries, as well as their screening by nucleic acid hybridization, are well known to those of ordinary skill in the art. See, e.g., *DNA Cloning*: Vol. I, supra; *Nucleic Acid Hybridization*, supra; *Oligonucleotide Synthesis*, supra; Sambrook et al., supra.

First, a DNA library is prepared. The library can consist of a genomic DNA library from the bacteria of interest (for the isolation of the cytotoxin gene) or from appropriate T cells (for the isolation of the desired cytokine gene). Once the library is constructed, oligonucleotides to probe the library are prepared and used to isolate the gene encoding the desired protein. The oligonucleotides are synthesized by any appropriate method. The particular nucleotide sequences selected are chosen so as to correspond to the codons encoding a known amino acid sequence from the desired protein. Since the genetic code is degenerate, it will often be necessary to synthesize several oligonucleotides to cover all, or a reasonable number, of the possible nucleotide sequences which encode a particular region of the protein. Thus, it is generally preferred in selecting a region upon which to base the probes, that the region not contain amino acids whose codons are highly degenerate. In certain circumstances, it may be desirable to prepare probes that are fairly long, and/or encompass regions of the amino acid sequence which would have a high degree of redundancy in corresponding nucleic acid sequences, particularly if this lengthy and/or redundant region is highly characteristic of the protein of interest. It may also be desirable to use two probes (or sets of probes), each to different regions of the gene, in a single hybridization experiment. Automated oligonucleotide synthesis has made the preparation of large families of probes relatively straightforward. While the exact length of the probe employed is not critical, generally it is recognized in the art that probes from about 14 to about 20 base pairs are usually effective. Longer probes of about 25 to about 60 base pairs are also used.

The selected oligonucleotide probes are labeled with a marker, such as a radionucleotide or biotin using standard procedures. The labeled set of probes is then used in the screening step, which consists of allowing the single-stranded probe to hybridize to isolated ssDNA from the library, according to standard techniques. Either stringent or permissive hybridization conditions could be appropriate, depending upon several factors, such as the length of the probe and whether the probe is derived from the same species as the library, or an evolutionarily close or distant species. The selection of the appropriate conditions is within the skill of the art. See, generally, *Nucleic Acid hybridization*, supra. The basic requirement is that hybridization conditions be of sufficient stringency so that selective hybridization occurs; i.e., hybridization is due to a sufficient degree of nucleic acid homology (e.g., at least about 75%), as opposed to nonspecific binding. Once a clone from the screened library has been identified by positive hybridization, it can be confirmed by restriction enzyme analysis and DNA sequencing that the particular library insert contains a gene for the desired protein.

Alternatively, DNA sequences encoding the proteins of interest can be prepared synthetically rather than cloned. The DNA sequence can be designed with the appropriate codons for the particular amino acid sequence. In general, one will select preferred codons for the intended host if the sequence will be used for expression. The complete sequence is assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

Once coding sequences for the desired proteins have been prepared or isolated, they can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage lambda (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), YCp19 (Saccharomyces) and bovine papilloma virus (mammalian cells). See, Generally, *DNA Cloning*: Vols. I & II, supra; T. Maniatis et al., supra; B. Perbal, supra.

Suitable restriction enzymes can then be employed to isolate the appropriate cytokine gene or cytotoxin gene and these sequences can be ligated together, using standard techniques (see, e.g., Sambrook et al., supra) and cloned to form a cytokine-cytotoxin fusion gene. It has been found that the cytokine gene can be fused either 5' or 3' to the particular cytotoxin gene in question. For example, the IL2-leukotoxin fusion described in the examples includes the IL2 gene fused to the 5'-end of the full-length lktA leukotoxin gene, whereas the γIFN-leukotoxin fusion includes the γIFN gene linked to the 3'-end of the truncated lktA gene.

The fusion gene can be placed under the control of a promoter, ribosome binding site (for bacterial expression) and, optionally, an operator (collectively referred to herein as "control" elements), so that the DNA sequence encoding the chimeric protein is transcribed into RNA in the host cell transformed by a vector containing this expression construction. The coding sequence may or may not contain a signal peptide or leader sequence. The chimeric proteins of the present invention can be expressed using, for example, native *P. haemolytica* promoter, the *E. coli* tac promoter or the protein A gene (spa) promoter and signal sequence. Leader sequences can be removed by the bacterial host in post-translational processing. See, e.g., U.S. Pat. Nos. 4,431,739; 4,425,437; 4,338,397.

In addition to control sequences, it may be desirable to add regulatory sequences which allow for regulation of the expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

An expression vector is constructed so that the particular fusion coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the particular chimeric protein of interest may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases, it may be desirable to add sequences which cause the secretion of the polypeptide from the host organism, with subsequent cleavage of the secretory signal. It may also be desirable to produce mutants or analogs of the chimeric proteins of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., T. Maniatis et al., supra; *DNA Cloning*, Vols. I and II, supra; *Nucleic Acid Hybridization*, supra.

A number of procaryotic expression vectors are known in the art. See, e.g., U.S. Pat. Nos. 4,440,859; 4,436,815; 4,431,740; 4,431,739; 4,428,941; 4,425,437; 4,418,149; 4,411,994; 4,366,246; 4,342,832; see also U.K. Patent Applications GB 2,121,054; GB 2,008,123; GB 2,007,675; and European Patent Application 103,395. Yeast expression vectors are also known in the art. See, e.g., U.S. Pat. Nos. 4,446,235; 4,443,539; 4,430,428; see also European Patent Applications 103,409; 100,561; 96,491.

Depending on the expression system and host selected, the proteins of the present invention are produced by growing host cells transformed by an expression vector described above under conditions whereby the protein of interest is expressed. The chimeric protein is then isolated from the host cells and purified. If the expression system secretes the protein into growth media, the protein can be purified directly from the media. If the protein is not secreted, it is isolated from cell lysates. The selection of the appropriate growth conditions and recovery methods are within the skill of the art.

An alternative method to identify proteins of the present invention is by constructing gene libraries, using the resulting clones to transform an appropriate microorganism and pooling and screening individual colonies using polyclonal serum or monoclonal antibodies to the desired antigen.

The chimeric proteins of the present invention may also be produced by chemical synthesis such as solid phase peptide synthesis, using known amino acid sequences or amino acid sequences derived from the DNA sequence of the genes of interest. Such methods are known to those skilled in the art. Chemical synthesis of peptides may be preferable if a small fragment of the antigen in question is capable of raising an immunological response in the subject of interest.

The proteins of the present invention or their fragments can be used to produce antibodies, both polyclonal and monoclonal. If polyclonal antibodies are desired, a selected mammal, (e.g., mouse, rabbit, goat, horse, etc.) is immunized with an antigen of the present invention, or its fragment, or a mutated antigen. Serum from the immunized animal is collected and treated according to known procedures. If serum containing polyclonal antibodies is used, the polyclonal antibodies can be purified by immunoaffinity chromatography, using known procedures.

Monoclonal antibodies to the proteins of the present invention, and to the fragments thereof, can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al., *Hybridoma Techniques* (1980); Hammerling et al., *Monoclonal Antibodies and T-cell Hybridomas* (1981); Kennett et al., *Monoclonal Antibodies* (1980); see also U.S. Pat. Nos. 4,341,761; 4,399,121; 4,427,783; 4,444,887; 4,452,570; 4,466,917; 4,472,500, 4,491,632; and 4,493,890. Panels of monoclonal antibodies produced against the antigen of interest, or fragment thereof, can be screened for various properties; i.e., for isotype, epitope, affinity, etc. Monoclonal antibodies are useful in purification, using immunoaffinity techniques, of the individual antigens which they are directed against.

Animals can be immunized with the compositions of the present invention by administration of the chimeric protein, or a fragment thereof, or an analog thereof. The chimeric protein can consist of an epitope of an RTX cytotoxin fused to an active fragment of a cytokine, as defined above. Thus, if the fragment or analog of the fusion protein is used, it will include the amino acid sequence of an epitope of the desired cytotoxin which interacts with the immune system to immunize the animal to that and structurally similar epitopes, and an active fragment of a cytokine as defined above.

Chimeric proteins used to immunize a subject contain at least 6–30 amino acids which form the sequence of the desired chimeric protein, and include a cytotoxin epitope and an active cytokine fragment.

Prior to immunization, it may be desirable to increase the immunogenicity of the particular chimeric protein, or an analog of the protein, or particularly fragments of the protein. This can be accomplished in any one of several ways known to those of skill in the art. For example, the antigenic peptide may be administered linked to a carrier. For example, a fragment may be conjugated with a macromolecular carrier. Suitable carriers are typically large, slowly metabolized macromolecules such as: proteins; polysaccharides, such as sepharose, agarose, cellulose, cellulose beads and the like; polymeric amino acids such as polyglutamic acid, polylysine, and the like; amino acid copolymers; and inactive virus particles. Especially usefusubsotein substrates are serum albumins, keyhole limpet hemocyanin, immunoglobulin molecules, thyroglobulin, ovalbumin, and other proteins well known to those skilled in the art.

The protein substrates may be used in their native form or their functional group content may be modified by, for example, succinylation of lysine residues or reaction with Cys-thiolactone. A sulfhydryl group may also be incorporated into the carrier (or antigen) by, for example, reaction of amino functions with 2-iminothiolane or the N-hydroxysuccinimide ester of 3-(4-dithiopyridyl propionate. Suitable carriers may also be modified to incorporate spacer arms (such as hexamethylene diamine or other bifunctional molecules of similar size) for attachment of peptides.

Other suitable carriers for the chimeric proteins of the present invention include VP6 polypeptides of rotaviruses, or functional fragments thereof, as disclosed in allowed U.S. patent application Ser. No. 07/489,790, filed Mar. 2, 1990, and incorporated herein by reference. Also useful is a fusion product of a viral protein and the subject cytokine-cytotoxin immunogen made by methods disclosed in U.S. Pat. No. 4,722,840. Still other suitable carriers include cells, such as lymphocytes, since presentation in this form mimics the natural mode of presentation in the subject, which gives rise to the immunized state. Alternatively, the fusion proteins of the present invention may be coupled to erythrocytes, preferably the subject's own erythrocytes. Methods of coupling peptides to proteins or cells are known to those of skill in the art.

The novel chimeric proteins of the instant invention can also be administered via a carrier virus which expresses the same. Carrier viruses which will find use with the instant invention include but are not limited to the vaccinia and other pox viruses, adenovirus, and herpes virus. By way of example, vaccinia virus recombinants expressing the novel chimeric proteins can be constructed as follows. The DNA encoding the particular cytokine-cytotoxin chimeric protein is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the instant chimeric protein into the viral genome. The resulting TK-recombinant can be selected by culturing the cells in the presence of 5-bromodeoxyuridine and picking viral plaques resistant thereto.

It is also possible to immunize a subject with a protein of the present invention, or a protective fragment thereof, or an analog thereof, which is administered alone, or mixed with a pharmaceutically acceptable vehicle or excipient. Typically, vaccines are prepared as injectables, either as liquid solutions or suspensions; solid forms suitable for solution in, or suspension in, liquid vehicles prior to injection may also be prepared. The preparation may also be emulsified or the active ingredient encapsulated in liposome vehicles. The active immunogenic ingredient is often mixed with vehicles containing excipients which are pharmaceutically acceptable and compatible with the active ingredient. Suitable vehicles are, for example, water, saline, dextrose, glycerol, ethanol, or the like, and combinations thereof. In addition, if desired, the vehicle may contain minor amounts of auxiliary substances such as wetting or emulsifying agents, pH buffering agents, or adjuvants which enhance the effectiveness of the vaccine. Adjuvants may include for example, muramyl dipeptides, avridine, aluminum hydroxide, oils, saponins and other substances known in the art. Actual methods of preparing such dosage forms are known, or will be apparent, to those skilled in the art. See, e.g., Remington's Pharmaceutical Sciences, Mack Publishing Company, Easton, Pa., 15th edition, 1975. The composition or formulation to be administered will, in any event, contain a quantity of the protein adequate to achieve the desired immunized state in the individual being treated.

Additional vaccine formulations which are suitable for other modes of administration include suppositories and, in some cases, aerosol, intranasal, oral formulations, and sustained release formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium, stearate, sodium saccharin cellulose, magnesium carbonate, and the like. These oral vaccine compositions may be taken in the form of solutions, suspensions, tablets, pills, capsules, sustained release formulations, or powders, and contain from about 10% to about 95% of the active ingredient, preferably about 25% to about 70%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Controlled or sustained release formulations are made by incorporating the chimeric protein into carriers or vehicles such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. The chimeric proteins can also be delivered using implanted mini-pumps, well known in the art.

Furthermore, the chimeric proteins (or complexes thereof) may be formulated into vaccine compositions in either neutral or salt forms. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

To immunize a subject, the polypeptide of interest, or an immunologically active fragment thereof, is administered parenterally, usually by intramuscular injection in an appropriate vehicle. Other modes of administration, however, such as subcutaneous, intravenous injection and intranasal delivery, are also acceptable. Injectable vaccine formulations will contain an effective amount of the active ingredient in a vehicle, the exact amount being readily determined by one skilled in the art. The active ingredient may typically range from about 1% to about 95% (w/w) of the composition, or even higher or lower if appropriate. The quantity to be administered depends on the animal to be treated, the capacity of the animal's immune system to synthesize antibodies, and the degree of protection desired. With the present vaccine formulations, 50 μg of active ingredient per ml of injected solution should be adequate to raise an immunological response when a dose of 1 to 5 ml per animal is administered. Other effective dosages can be readily established by one of ordinary skill in the art through routine trials establishing dose response curves. The subject is immunized by administration of the particular antigen or fragment thereof, or analog thereof, in at least one dose, and preferably two doses. Moreover, the animal may be administered as many doses as is required to maintain a state of immunity to pneumonia.

Below are examples of specific embodiments for carrying out the present invention. The examples are offered for illustrative purposes only, and are not intended to limit the scope of the present invention in any way.

Deposits of Strains Useful in Practicing the Invention

A deposit of biologically pure cultures of the following strains was made with the American Type Culture Collection, 12301 Parklawn Drive, Rockville, Md. The accession number indicated was assigned after successful viability testing, and the requisite fees were paid. Access to said cultures will be available during pendency of the patent application to one determined by the Commissioner to be entitled thereto under 37 CFR 1.14 and 35 USC 122. All restriction on availability of said cultures to the public will be irrevocably removed upon the granting of a patent based upon the application. Moreover, the designated deposits will be maintained for a period of thirty (30) years from the date of deposit, or for five (5) years after the last request for the deposit; or for the enforceable life of the U.S. patent, whichever is longer. Should a culture become nonviable or be inadvertently destroyed, or, in the case of plasmid-containing strains, lose its plasmid, it will be replaced with a viable culture(s) of the same taxonomic description.

| Strain | Deposit Date | ATCC No. |
|---|---|---|
| *P. haemolytica* serotype 1 B122 | February 1, 1989 | 53863 |
| pAA356 in *E. coli* W1485 | August 14, 1990 | 68386 |
| pAA352 in *E. coli* W1485 | March 30, 1990 | 68283 |

C. Experimental

Materials and Methods

Enzymes were purchased from commercial sources, and used according to the manufacturers' directions. Radionucleotides and nitrocellulose filters were also purchased from commercial sources.

In the cloning of DNA fragments, except where noted, all DNA manipulations were done according to standard procedures. See Sambrook et al., supra. Restriction enzymes, $T^4$ DNA ligase, *E. coli*, DNA polymerase I, Klenow fragment, and other biological reagents were purchased from commercial suppliers and used according to the manufacturers' directions. Double-stranded DNA fragments were separated on agarose gels.

CDNA and genomic libraries were prepared by standard techniques in pUC13 and the bacteriophage lambda gt11, respectively. See *DNA Cloning*: Vols I and II, supra.

*P. haemolytica* biotype A, serotype 1 ("A1") strain B122 was isolated from the lung of a calf which died of pneumonic pasteurellosis and was stored at −70° C. in defibrinated blood. Routine propagation was carried out on blood agar plates or in brain heart infusion broth (Difco Laboratories, Detroit, Mich.) supplemented with 5% (v/v) horse serum (Gibco Canada Ltd., Burlington, Canada). All cultures were incubated at 37° C.

EXAMPLE 1

Construction of an IL2-leukotoxin Gene Fusion

1. Modification of the Bovine IL2 Gene

The bovine IL2 gene, in the plasmid pBOVIL2 (CIBA-GEIGY, Basel, Switzerland), was digested to completion with the restriction endonuclease BclI and the single-stranded ends removed by Mung Bean nuclease treatment. The DNA was then digested with EcoRI in order to excise the IL2 gene fragment. This fragment was ligated into the cloning vector pTZ19R (Pharmacia, Canada) (EcoRI/SmaI-digested). Sequence analysis revealed two populations of clones which differed only in the reading frame at the 3'-end of the gene. The first, pAA284, had a terminal sequence of 5'-TCA ACA ATG ACT <u>GGGATC C</u>TC-3' (BamHI site in vector underlined) while the second, pAA285, had a terminal sequence of 5'-TCA ACA ATG ACT GG<u>G GAT CC</u>T-3'. The sequences shown in bold face are from the IL2 gene. Because of the differences in reading frame, heterologous genes in two out of three reading frames can be fused to the bovine IL2 gene.

2. Construction of IL2-LKT Fusions

To isolate the leukotoxin gene, gene libraries of *P. haemolytica* A1 (strain B122) were constructed using standard techniques. See Lo et al., *Infect. Immun.*, supra; *DNA Cloning*: Vols. I and II, supra; and Sambrook et al., supra. A genomic library was constructed in the plasmid vector pUC13 and a DNA library constructed in the bacteriophage lambda gt11. The resulting clones were used to transform *E. coli* and-individual colonies were pooled and screened for reaction with serum from a calf which had survived a *P. haemolytica* infection and that had been boosted with a concentrated culture supernatant of *P. haemolytica* to increase anti-leukotoxin antibody levels. Positive colonies were screened for their ability to produce leukotoxin by incubating cell lysates with bovine neutrophils and subsequently measuring release of lactate dehydrogenase from the latter.

Several positive colonies were identified and these recombinants were analyzed by restriction endonuclease mapping. One clone appeared to be identical to a leukotoxin gene cloned previously. See Lo et al., *Infect. Immun.*, supra. To confirm this, smaller fragments were recloned and the restriction maps compared. It was determined that approximately 4 kilobase pairs of DNA had been cloned. Progressively larger clones were isolated by carrying out a chromosome walk (5' to 3' direction) in order to isolate full-length recombinants which were approximately 8 kb in length. The final construct was termed pAA114. This construct contained the entire leukotoxin gene sequence. The structure of this plasmid is shown in FIG. 1.

lktA, a MaeI restriction endonuclease fragment from pAA114 which contained the entire leukotoxin gene, was treated with the Klenow fragment of DNA polymerase I plus nucleotide triphosphates and ligated into the SmaI site of the cloning vector pUC13. This plasmid was named pAA179. From this, an expression construct was made in the ptac-based vector pGH432: lacI digested with SmaI. This construct was termed pAA345 and contained the entire MaeI fragment described above. This plasmid expresses full-length leukotoxin.

Figure 2:
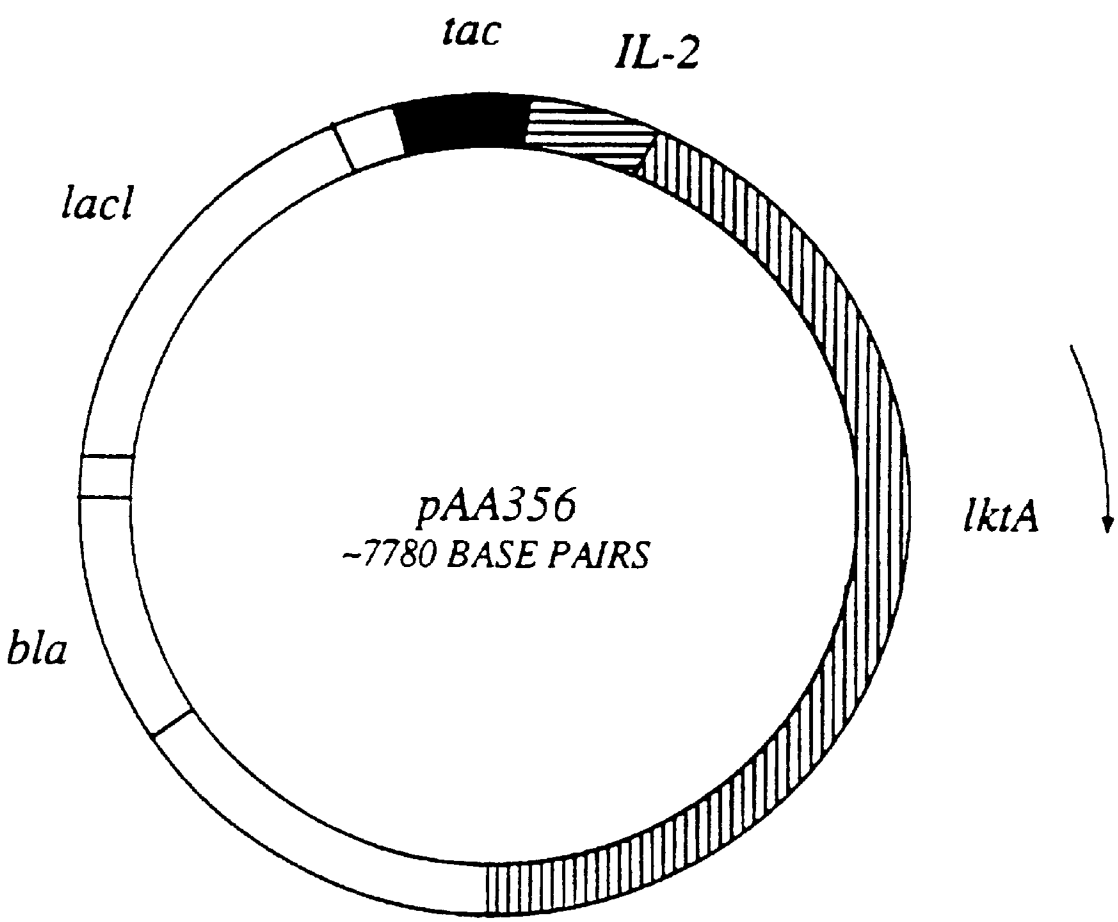
FIG. 2 shows the structure of plasmid pAA356 carrying a bovine IL2-leukotoxin (IL2-LKT) gene fusion wherein tac is the hybrid trp::lac promoter from *E. coli*; bla represents the β-lactamase gene (ampicillin resistance); lktA is the *P. haemolytica* leukotoxin structural gene; IL2 is the bovine interleukin-2 structural gene; and lacl is the *E. coli* lac operon repressor.

The plasmid pAA345 containing the *P. haemolytica* leukotoxin gene lktA was digested with BamHI and BglII, and the 2.75 kilobase fragment was ligated into BamHI-digested pAA285 (above). The resulting plasmid, pAA354, was digested with ApaLI, the 5'-overhang filled in with the Klenow fragment of DNA polymerase I, and finally digested with BamHI. The IL2-LKT fragment was gel purified and ligated into the expression vector pGH433 lacI which had been cut with BglII, filled in with Klenow polymerase and digested with BamHI. The resulting clone, pAA356 (ATCC No. 68386), contained the IL2-LKT gene fusion under the control of the *E. coli* tac promoter. FIG. 2 shows the structure of pAA356 while FIG. 3 (SEQ ID NO:1–2) shows the nucleotide sequence and corresponding amino acid sequence of the fusion protein expressed by this plasmid. The resulting fusion is a gene fusion of bovine IL2 to the 5'-end of the full-length lktA gene (approximately 750 bp).

3. Purification of Recombinant IL2-LKT

Recombinant IL2-LKT was purified using the following procedure. Five to ten colonies of *E. coli* W1485/pAA356 (ATCC no. 68386) were inoculated into 10 ml of TB broth supplemented with 100 micrograms/ml of ampicillin and incubated at 37° C. for 6 hours on a G10 shaker, 220 rpm. Four ml of this culture was diluted into each of two baffled Fernbach flasks containing 400 ml of TB broth+ampicillin and incubated overnight as described above. Cells were harvested by centrifugation for 10 minutes at 4,000 rpm in polypropylene bottles, 500 ml volume, using a Sorvall GS3 rotor. The pellet was resuspended in an equal volume of TB broth containing ampicillin which had been prewarmed to 37° C. (i.e., 2×400 ml), and the cells were incubated for 2 hours as described above.

3.2 ml of isopropyl-B,D-thiogalactopyranoside (IPTG, Gibco/BRL), 500 mM in water (final concentration=4 mM), was added to each culture in order to induce synthesis of recombinant IL2-LKT. Cultures were incubated for two hours. Cells were harvested by centrifugation as described above, resuspended in 30 ml of 50 mM Tris-hydrochloride, 25% (w/v) sucrose, pH 8.0, and frozen at −70° C. The frozen cells were thawed at room temperature after 60 minutes at −70° C., and 5 ml of lysozyme (Sigma, 20 mg/ml in 250 mM Tris-HCl, pH 8.0) was added. The mixture was vortexed at high speed for 10 seconds and then placed on ice for 15 minutes. The cells were then added to 500 ml of lysis buffer in a 1000 ml beaker and mixed by stirring with a 2 ml pipette. The beaker containing the lysed cell suspension was placed on ice and sonicated for a total of 2.5 minutes (5–30 second bursts with 1 minute cooling between each) with a Braun sonicator, large probe, set at 100 watts power. Equal volumes of the solution were placed in Teflon SS34 centrifuge tubes and centrifuged for 20 minutes at 10,000 rpm in a Sorvall SS34 rotor. The pellets were resuspended in a total of 100 ml of sterile double distilled water by vortexing at high speed, and the centrifugation step repeated. Supernatants were discarded and the pellets combined in 20 ml of 10 mM Tris-HCl, 150 mM NaCl, pH 8.0 (Tris-buffered saline) and the suspension frozen overnight at −20° C.

The recombinant suspension was thawed at room temperature and added to 100 ml of 8 M Guanidine HCl (Sigma) in Tris-buffered saline and mixed vigorously. A magnetic stir bar was placed in the bottle and the solubilized sample was mixed at room temperature for 30 minutes. The solution was transferred to a 2000 ml Ehrlenmyer flask and 1200 ml of Tris-buffered saline was quickly added. This mixture was stirred at room temperature for an additional 2 hours. 500 ml aliquots were placed in dialysis bags (Spectrum, 63.7 mm diameter, 6,000–8,000 MW cutoff, #132670, from Fisher scientific) and these were placed in 4,000 ml beakers containing 3,500 ml of Tris-buffered saline+0.5 M Guanidine HCl. The beakers were placed in a 4° C. room on a magnetic stirrer overnight after which dialysis buffer was replaced with Tris-buffered saline+0.1 M Guanidine HCl and dialysis continued for 12 hours. The buffer was then replaced with Tris-buffered saline+0.05 M Guanidine HCl and dialysis continued overnight. The buffer was replaced with Tris-buffered saline (no guanidine), and dialysis continued for 12 hours. This was repeated three more times. The final solution was poured into a 2000 ml plastic roller bottle (Corning) and 13 ml of 100 mM PMSF (in ethanol) was added to inhibit protease activity. The solution was stored at −20° C. in 100 ml aliquots.

EXAMPLE 2

Measurement of IL2 Activity

Cell-free lysates were prepared by detergent lysis from *E. coli* carrying pAA356 as described above and an isogenic strain carrying the pGH433 vector without IL2-LKT. The IL2-LKT molecule was evident on polyacrylamide gel electrophoresis. IL2 activity was measured using an IL2-dependent T-cell line derived from Con-A-stimulated peripheral blood mononuclear cells. The recombinant lysates were added to IL2-dependent cells and proliferation was measured after 48 hours incubation at 37° C. The proliferative response to IL2 was compared to T lymphocytes cultured in medium alone or cells stimulated with recombinant human IL2 (specific activity=$3.6\times10^6$ U/mg). Recombinant leukotoxin without IL2 was also included as a control. The results, shown in Table 1, confirm the IL2 activity of the fusion protein.

TABLE 1

IL2 Activity of IL2-LKT Fusion Product Tested on an IL2-Dependent T-Cell Line[a]

| | Counts Per Minute | | |
|---|---|---|---|
| Sample | $10^{-2}$ | $10^{-3}$ | $10^{-4}$ |
| Recombinant Leukotoxin | 357 | 372 | 383 |
| Vector Only (pGH433) | 487 | 598 | 506 |
| IL2-LKT (pAA356) | 28,634 | 22,329 | 9,961 |

[a]Activity induced by recombinant human IL2 standards: 25 U/ml = 30,159 cpm; 12 U/ml = 23,666 cpm; 6 U/ml = 22,837 cpm; 3 U/ml = 15,828 cpm; 1.5 U/ml = 8,944 cpm; 0.6 U/ml = 3,233 cpm.

Thus, it is evident that the chimeric protein retains IL2 cell proliferative activity.

EXAMPLE 3

Serological Response to *P. haemolytica* LKT and the IL2-LKT Chimeric Molecule To test whether the serological activity of the chimeric molecule differed from the serological activity of leukotoxin alone, the following experiment was done.

Calves (three per group) were immunized at time 0 with 100 μg of: (1) full-length recombinant *P. haemolytica* leukotoxin (LKT), (2) an equivalent molar ratio of the IL2-LKT chimeric protein, or (3) PBS. All of these were formulated in phosphate-buffered saline with Emulsigen as the adjuvant. Serological assessment of immune responsiveness to LKT or the chimera was carried out at -15, -7, -3 days and immediately prior to immunization on day 0, and daily for 20 days post-immunization. Serum antibody of the IgG class was assessed by enzyme-linked immunosorbent assay, using leukotoxin as the antigen.

Figure 4A:
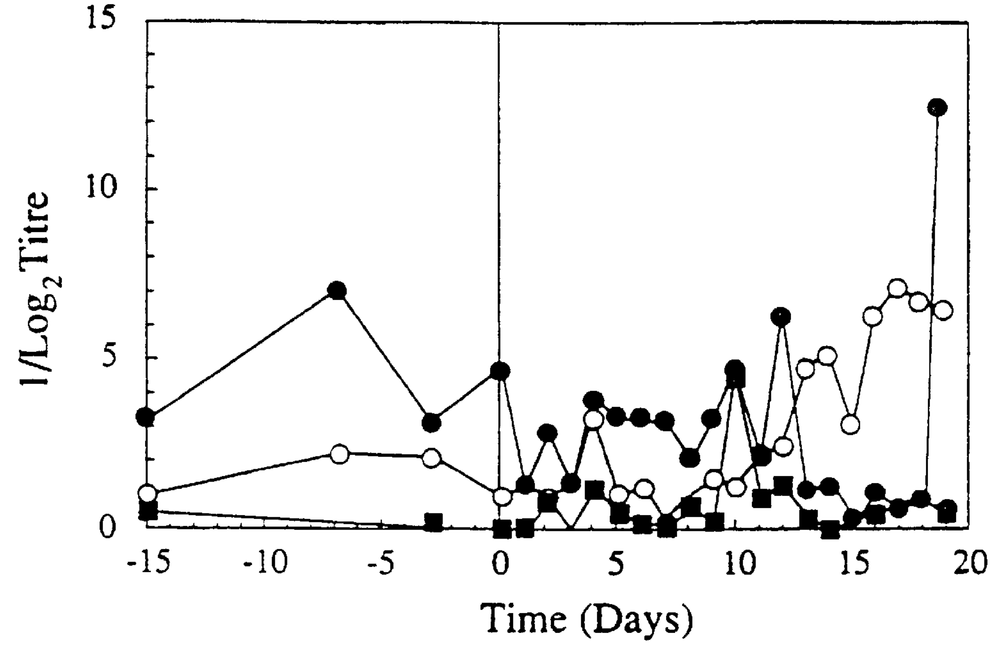
FIGS. 4A–4C depict the serological response to *P. haemolytica* LKT and the IL2-LKT chimeric molecule.
Figure 4B:
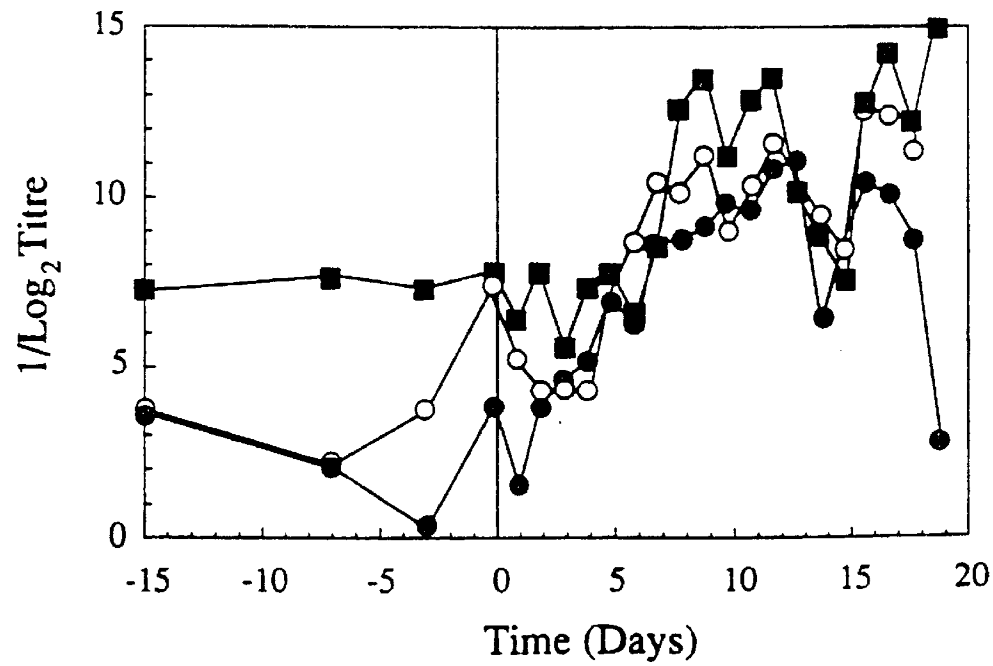
Figure 4C:
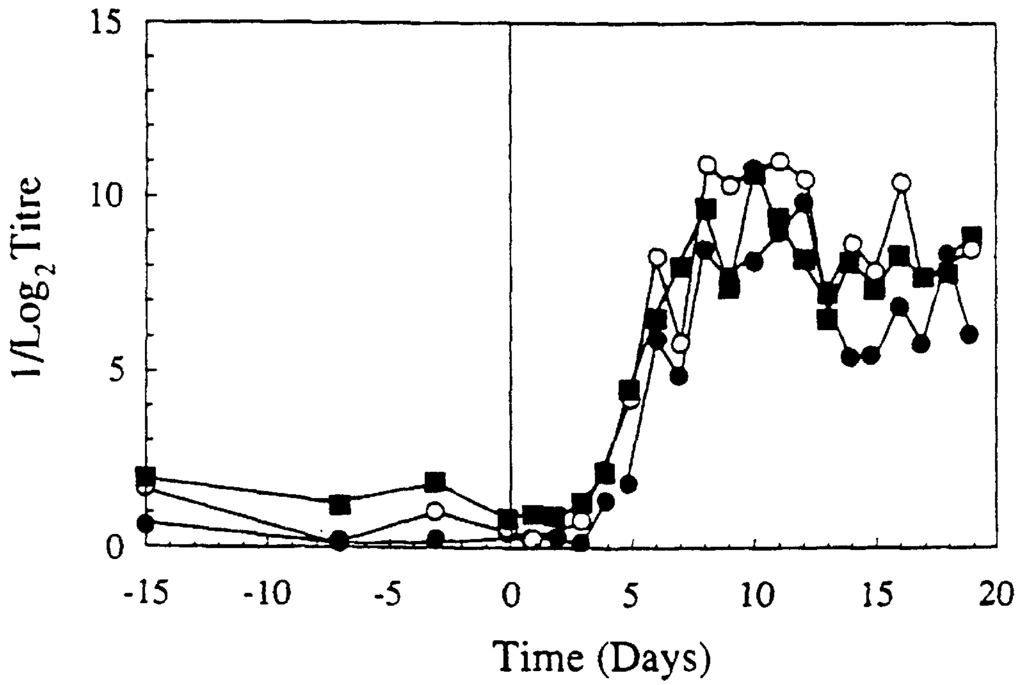

As can be seen in FIGS. 4A–4C, the mean of individual serological titers in the nonimmunized group (FIG. 4A) remained at levels below 1/32 ($log_2$ 5). One of the three calves in this group seroconverted to leukotoxin positive at day 20 because of natural infection with *P. haemolytica*. In the LKT-immunized group (4B), titers began to rise at day 6 after immunization, reaching a maximum (1/1024–1/8192; $log_2$ 10–14) on day 8–10, where they remained for the duration of the experiment. In the chimera-immunized animals (4C), responses to LKT began to rise after day 4 postimmunization, reaching a maximum (1/1024–1/4096 $log_2$ 10–12) on day 8 after immunization.

Thus, the serological activity of the chimeric molecule when compared to the activity of leukotoxin alone was not significantly different, both with respect to kinetics and magnitude. Serum antibody from one animal in the leukotoxin immunized group appeared to react with leukotoxin prior to immunization (with titers>1/128; $log_2$ 7), and while it is unlikely that this animal suffered a *P. haemolytica* infection, serum antibodies against another bacterial toxin could be cross-reacting with leukotoxin. The conclusion from this experiment is that when IL2 is genetically chimerized to the leukotoxin molecule, it does not affect the ability of the LKT to induce a normal IgG antibody response when compared to the administration of recombinant leukotoxin alone.

EXAMPLE 4

Immunization of Calves with LKT and the IL2-LKT Chimeric Molecule

Calves were immunized at time 0 according to the protocols in Table 2. 117 micrograms of IL2-LKT were given (molar equivalent) and 100 micrograms of LKT given (molar equivalent).

TABLE 2

| Calf Immunization Protocols | | | |
|---|---|---|---|
| Antigen | Adjuvant | Number of Doses | Interval |
| LKT | Emulsigen-plus | 5 | 12 H |
| IL2-LKT | Emulsigen-plus | 5 | 12 H |
| IL2-LKT | Emulsigen-plus | 1 | |
| IL2-LKT | None | 5 | 12 H |

LKT refers to full-length leukotoxin.
IL2-LKT refers to LKT chimerized to bovine IL2.
In multiple-dose regimes, five doses were given at 12 h intervals over 2.5 days.

1. Precursor Frequency Analysis

The number of cells capable of responding to LKT following immunization was assessed using limiting dilution analysis (LDA). At the times indicated following immunization, T and B lymphocytes were isolated from peripheral blood by passing through Sephadex G-10 columns. Monocyte depletion was confirmed by flow cytometry. This cell population was diluted to various concentrations ($10^5$ to $10^2$/ml) and added to 96-well plates in the presence of feeder cells (autologous 1500 rad irradiated PBMC) and antigen (LKT) at a previously determined optimal concentration (20 μg/ml). In some experiments, cells were stimulated with IL2-LKT (LKT356) or an equimolar concentration of IL2. Following incubation at 37° C. for 5 to 7 days, $^3$H-thymidine was added to wells and cultures were harvested after an additional 24 hours incubation, counted and the percent negative cultures assessed following comparison with control cultures (i.e., cells cultured in the absence of antigen). Semi-$Log_{10}$ plots were done of $Log_{10}$ Percent negative cultures (Y) against number of cells plated (X). The number of cells responding at 37% negative cultures was calculated from an equation derived from the regression curve of Y versus X.

Figure 5:
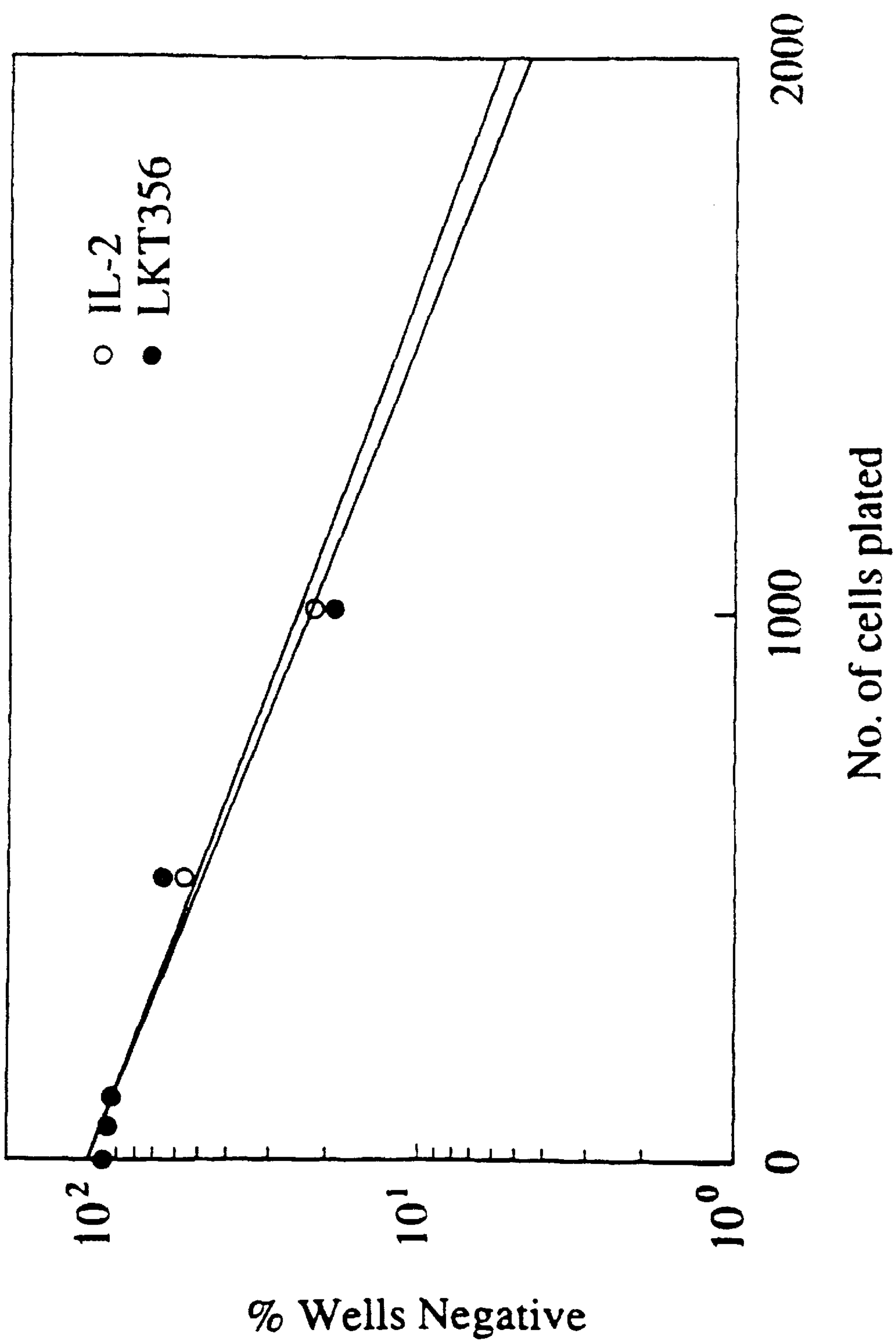
FIG. 5 shows precursor frequency analysis of PBMC responding to recombinant bovine IL2-LKT chimeric protein.

As can be seen in FIG. 5, the chimerization of LKT to IL2 does not affect the ability of PBMC to respond to the IL2 component of the molecule. Furthermore, precursor frequency analysis of cells responding to LKT or IL2-LKT yielded the following results: After immunization with LKT or IL2-LKT, with or without the adjuvant Emulsigen-plus, there was a dramatic increase in the number of cells responding to LKT. Following a single immunizing dose of IL2-LKT with Emulsigen-plus, there was no detectable increase in precursor frequency (Table 3).

2. Serology

Serum from the immunized calves was assessed for antibodies against LKT at the times indicated in Table 3. LKT antibodies were detected using standard ELISAs.

All animals showed an increased antibody titer against LKT following immunization. Increases were more marked in those animals given Emulsigen-plus in the formulation. Specifically, animals immunized with the chimera had a titer of 1/700 15 days after immunization, whereas when the same immunization was done with Emulsigen-plus, the titer was 1/35,000. Furthermore, even following one dose of IL2-LKT with Emulsigen-plus, the serological titer was 1/2500 (Table 3).

TABLE 3

| Immunization[a] | | Adjuvant[b] | Time (D)[c] | F[d] | Serology[e] |
|---|---|---|---|---|---|
| LKT | (M) | Emulsigen-plus | 0 | 1:55657 | 1/150 |
| | | | 15 | 1:11087 | 1/6000 |
| IL2-LKT | (M) | None | 0 | 1:16728 | 1/200 |
| | | | 15 | 1:8976 | 1/700 |
| IL2-LKT | (S) | Emulsigen-plus | 0 | 1:50755 | 1/300 |
| | | | 15 | 1:117317 | 1/2500 |
| IL2-LKT | (M) | None*** | 0 | 1:20728 | 1/1000 |
| | | | 15 | 1:16882 | 1/35000 |

[a]M: multiple dose regimen; S: single bonus dose.
[b]Adjuvant given with all doses. ***High values at time 0 may indicate a prior infection or x-reactivity.
[c]Time following first inoculation.
[d]Precursor frequency of B and T cells proliferating in response to LKT.
[e]Serology determined by ELISA using LKT as antigen.

Thus, this study demonstrated the ability of LKT and IL2-LKT formulations to elicit cellular and humoral immunity responses following single or multiple immunization. When Emulsigen-plus was used as an adjuvant, there was a high serological response. This was regardless of whether LKT or IL2-LKT was given as a single or multiple immunization regimen. The single dose inoculum gave a high humoral response (antibody titer) in the near absence of any detectable cellular response. The animal that elicited the highest cellular response after immunization was that which was given IL2-LKT alone. Therefore, IL2-LKT can elicit the highest state of cellular reactivity. A higher humoral response can also be elicited by combining the chimeric protein with an adjuvant.

EXAMPLE 5

Construction of a γIFN-Leukotoxin Gene Fusion

To isolate the leukotoxin gene, gene libraries of *P. haemolytica* A1 (strain B122) were constructed using standard techniques. See Lo et al., *Infect. Immun.*, supra; *DNA Cloning*: Vols. I and II, supra; and T. MANIATIS et al., supra. A genomic library was constructed in the plasmid vector pUC13 and a DNA library constructed in the bacteriophage lambda gt11. The resulting clones were used to transform *E. coli* and individual colonies were pooled and screened for reaction with serum from a calf which had survived a *P. haemolytica* infection and that had been boosted with a concentrated culture supernatant of *P. haemolytica* to increase anti-leukotoxin antibody levels. Positive colonies were screened for their ability to produce leukotoxin by incubating cell lysates with bovine neutrophils and subsequently measuring release of lactate dehydrogenase from the latter.

Several positive colonies were identified and these recombinants were analyzed by restriction endonuclease mapping. One clone appeared to be identical to a leukotoxin gene cloned previously. See Lo et al., *Infect. Immun.*, supra. To confirm this, smaller fragments were recloned and the restriction maps compared. It was determined that approximately 4 kilobase pairs of DNA had been cloned. Progressively larger clones were isolated by carrying out a chromosome walk (5' to 3' direction) in order to isolate full-length recombinants which were approximately 8 kb in length. The final construct was termed pAA114. This construct contained the entire leukotoxin gene sequence. The structure of this plasmid is shown in FIG. 1.

lktA, a MaeI restriction endonuclease fragment from pAA114 which contained the entire leukotoxin gene, was treated with the Klenow fragment of DNA polymerase I plus nucleotide triphosphates and ligated into the SmaI site of the cloning vector pUC13. This plasmid was named pAA179. From this, two expression constructs were made in the ptac-based vector pGH432: laci digested with SmaI. One, pAA342, consisted of the 5'-AhaIII fragment of the lktA gene while the other, pAA345, contained the entire MaeI fragment described above. The clone pAA342 expressed a truncated leukotoxin peptide at high levels while pAA345 expressed full length leukotoxin at very low levels. Therefore, the 3' end of the lktA gene (StyI BamHI fragment from pAA345) was ligated to StyI BamHI-digested pAA342, yielding the plasmid pAA352, which also expressed the truncated leukotoxin, termed LKT 352.

Figure 6:
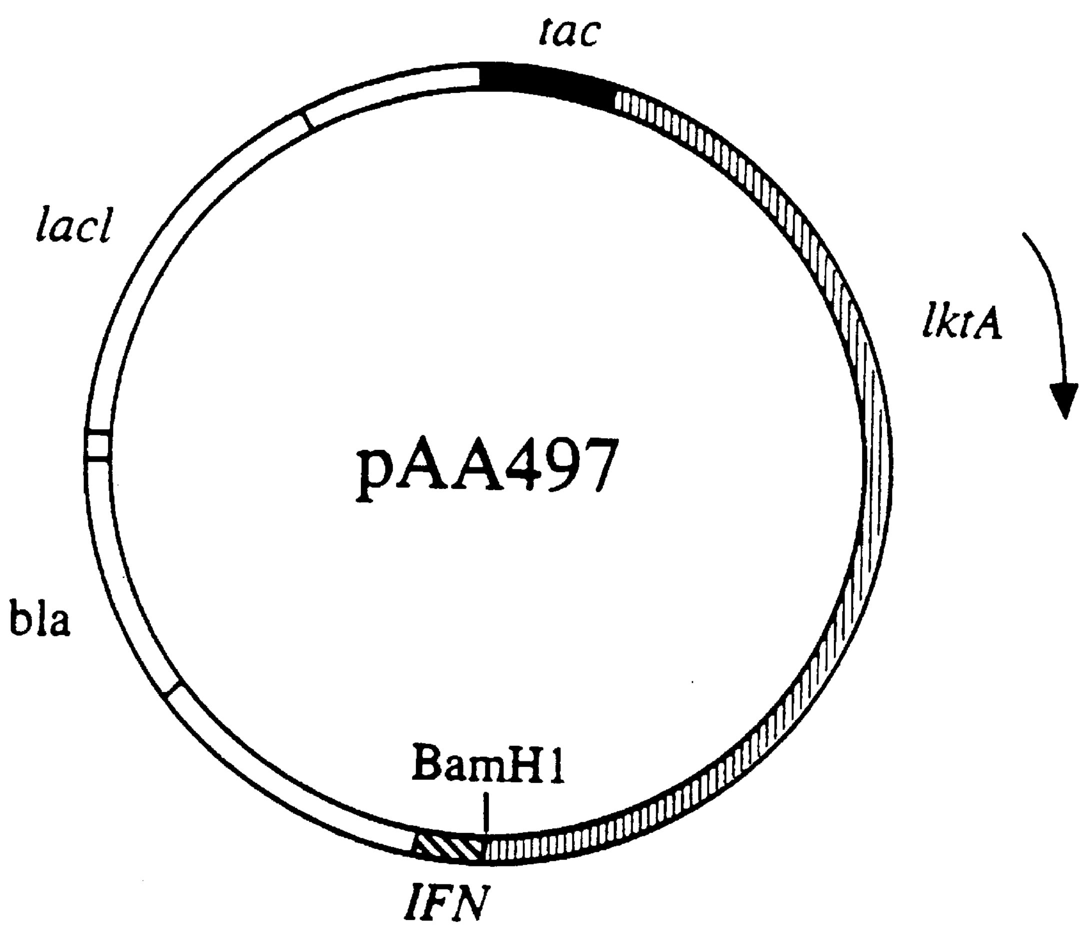
FIG. 6 shows the structure of plasmid pAA497 carrying a bovine γIFN-LKT gene fusion wherein tac is the hybrid trp::lac promoter from *E. coli*; bla represents the β-lactamase gene (ampicillin resistance); lktA is the *P. haemolytica* leukotoxin structural gene; IFN is the bovine gamma-interferon structural gene; and lac1 is the *E. coli* lac operon repressor.

The coding sequence of the bovine γIFN gene from the plasmid pBOVIFNγ (CIBA-GEIGY, Basel, Switzerland), was cloned as a BalI/SspI fragment into pAA352 digested with BamHI and filled in with Klenow DNA Polymerase. The ligation mixture was transformed into *E. coli* strain JM105 and ampicillin-resistant transformants were selected. DNA from four transformants was analyzed by restriction endonuclease digestion and one plasmid, pAA497 (FIG. 6), was found to contain the interferon gene in the correct orientation. The nucleotide sequence and corresponding amino acid sequence of the fusion is shown in FIG. 7 (SEQ ID NO:3–4). The resulting fusion is a gene fusion of bovine γIFN to the 3'-end of the truncated lktA gene.

The recombinant fusion protein was purified as described in Example 1.3.

EXAMPLE 6

Measurement of γIFN Activity

Purified recombinant γIFN-LKT was prepared as described above. IFN activity was tested using three different assays:

1) Expression of MHC class II on monocytes and macrophages.
2) Inhibition of T cell proliferation.
3) Ability to inhibit viral replication.

1. Expression of MHC Class II on Monocytes and MacroPhages

Peripheral blood mononuclear cells (PBMC) were isolated from bovine venous blood and incubated at 37° C. for 18 hours with different concentrations of the γIFN-LKT chimera and molar equivalent amounts of recombinant bovine γIFN. Cells were then washed and resuspended in PBS-gelatin containing $NaN_3$. Cells were incubated with mouse monoclonal anti-MHC Class II antibody for 30 minutes followed by 30 minutes incubation with FITC labelled goat anti-mouse antibody. The percent positive and peak fluorescence was estimated using a Becton-Dickenson FACScan. Results are shown in Table 4. An elevation of peak fluorescence is an indication of interferon activity.

TABLE 4

| | Peak Fluorescence | | |
|---|---|---|---|
| Source Cells | Medium | γIFN | γIFN-LKT |
| Animal #1 | 114 | 153 | 140 |
| Animal #2 | 120 | 139 | 140 |

2. Inhibition of T-Cell-Proliferation

Cells were incubated with Con-A in the presence of LKT, γIFN-LKT, or LKT+γIFN, and the proliferative response assessed following three days of incubation. Results are shown in Table 5. A decrease in this response is indicative of IFN activity.

TABLE 5

| | Increased Proliferative Response | | |
|---|---|---|---|
| Source Cells | Medium | γIFN-LKT | LKT + γIFN |
| Animal #1 | ++++ | +/− | ++ |
| Animal #2 | ++++ | − | ++ |

3. Ability to Inhibit Viral Replication

The activity of γIFN-LKT was directly compared to the activity of equimolar quantities of γIFN in a standard VSV plaque inhibition assay using GBK cells as previously reported (Babiuk, L. A. and Rouse, B. T. (1976) *Infect. Immun.* 13:1567). Briefly, GBK cells growing in 96-well flat-bottom tissue culture plates (NUNC, Roskilde, DK)

were treated with two-fold dilutions of recombinant γIFN. After overnight incubation, the culture media was removed and 100 μl of fresh culture media containing 100 PFU of VSV was added to each well. After 2 hr of incubation, this virus inoculum was removed and the wells were overlayed with 200 μl of methyl cellulose/MEM. Culture plates were further incubated for 2 hr and stained with crystal violet. The antiviral titer was taken as the dilution of supernatants at which 50% of the cells were protected against VSV. The specific activity of the chimera was estimated as 78,000 units per mg protein.

EXAMPLE 7

Identification of Neutralizing Epitopes of Leukotoxin

As explained above, the *P. haemolytica* leukotoxin protein is a member of the RTX family of toxins and contains a series of repeated amino acid domains near the carboxy terminus. These domains are likely to be epitopes useful in the subject chimeric proteins. The consensus amino acid sequence is Gly-Gly-X-Gly-(Asn or Asp)-Asp, (SEQ ID NO:5) where X is Lys, Asp, Val or Asn. (Highlander et al. (1989) *DNA* 8:15–28; Welch, R. A. (1991) *Molec. Microbiol.* 5:521–528). However, other substitutions likely to render immunologically active peptides include substitutions with an aliphatic amino acid, such as Gly, Ala, Val, Leu, Ile, a charged amino acid such as Asp, Glu, Arg, His or Lys, or a corresponding neutral amino acid such as Asn or Gln.

Based on this information, a synthetic peptide of the sequence GGNGDDFIDGGKGNDLLHGG (SEQ ID NO:6) was constructed by standard solid phase technology on an Applied Biosystems peptide synthesizer. Mice were immunized with authentic leukotoxins prepared from either *P. haemolytica*, or *Actinobacillus pleuropneumoniae* (serotypes 1 and 5) at 100 μg per dose with Freund's Complete Adjuvant (first vaccination) or Freund's Incomplete Adjuvant (all subsequent vaccinations). High titer serum samples from immunized mice were tested, in a standard ELISA, for the following: (1) their ability to react with recombinant and authentic *P. haemolytica* leukotoxin; (2) their ability to react with the toxin produced by *A. pleuropneumoniae*; and (3) their ability to react with the synthetic peptide described above. The results, summarized in Table 6, are expressed as the relative reactivity at a serum dilution of 1 in 100,000.

TABLE 6

Presence of Synthetic Peptide Epitopes in Toxins from *P. haemolytica* and *A. pleuropneumonia* serotypes 1 and 5

| | Relative Serological Response To: | | |
|---|---|---|---|
| Toxin Prepared From: | Synthetic Peptide | Actinobacillus Toxin | Pasteurella Toxin |
| *A. pleuropneumoniae* sero. 5 | +++ | ++++ | ++ |
| *A. pleuropneumoniae* sero. 1 | + | ++++ | + |
| *P. haemolytica* | +++ | not determined | ++++ |

This data indicated that animals vaccinated with either of the three leukotoxins developed antibodies which reacted with all toxins and a synthetic peptide based on a portion of the *P. haemolytica* toxin. Once an appropriate level of anti-peptide serum antibody was reached (ELISA titer of 100,000 or greater), spleen cells were fused with NS1 cells and monoclonal antibody-producing clones were isolated by standard techniques. Culture supernatants from these clones were tested for their ability to react with the synthetic peptide (above) and the respective toxins in an ELISA assay. The results for 2 clones are shown in Table 7.

TABLE 7

| | | Relative Reaction With: | | |
|---|---|---|---|---|
| Clone | Immunogen | Pasteurella Toxin | Synthetic Peptide | Actinobacillus Toxin |
| ET122-6A4-3 | Pasteurella toxin | ++++ | +++++ | ND[1] |
| N37-3F9-6 | Actinobacillus toxin | ND | ++++ | +++++ |

[1]Not determined

These results demonstrate that each of these monoclonal antibodies react with an epitope which is shared by the *P. haemolytica* and *A. pleuropneumoniae* toxins, and that this epitope is structurally similar to that of the synthetic peptide. This peptide is also structurally similar to a bovine rotavirus synthetic peptide of the sequence TMNGNEFQTGGIGNLPIRNWNAC, representing amino acids 40–60 of the VP6 protein. The monoclonal antibodies described above can therefore be used to determine the degree of their cross-reactivity with rotavirus proteins based on the epitope represented by the synthetic peptides. Furthermore, the immunologically active leukotoxin fragments might prove useful in immunizing against rotavirus.

These leukotoxin epitopes can be fused to cytokines such as IL2 and γIFN, or active fragments thereof, to form chimeric proteins for use in vaccine compositions.

Thus, chimeric proteins for use in stimulating immunity against pneumonia and other respiratory diseases have been disclosed. Although preferred embodiments of the subject invention have been described in some detail, it is understood that obvious variations can be made without departing from the spirit and the scope of the invention as defined by the appended claims.

We claim:

1. A vaccine composition comprising an immunogenic chimeric protein that comprises gamma-interferon (γIFN), or an active fragment thereof, linked to at least one epitope of a leukotoxin derived from *Pasteurella haemolytica*, and a pharmaceutically acceptable vehicle.

2. The vaccine composition of claim 1 wherein said chimeric protein is linked to carrier.

3. A method of preventing or ameliorating respiratory disease comprising administering to a subject ruminant an effective amount of a vaccine composition according to claim 1.

4. The vaccine composition of claim 1, wherein said leukotoxin is full-length *P. haemolytica* leukotoxin.

5. The vaccine composition of claim 1, wherein said leukotoxin is a truncated leukotoxin that lacks cytotoxic activity.

6. The vaccine composition of claim 5, wherein said truncated leukotoxin is LKT 352.

7. The vaccine composition of claim 1, wherein said γIFN is bovine γIFN, or an active fragment thereof.

8. The vaccine composition of claim 7, wherein said chimeric protein comprises an amino acid sequence (a) encoded by a polynucleotide that encodes the LKT-γIFN amino acid sequence of SEQ ID NO:4, or (b) encoded by a polynucleotide that hybridizes to the polynucleotide of (a) under stringent hybridization conditions.

9. The vaccine composition of claim 1, further comprising an adjuvant.

10. The vaccine composition of claim 8, further comprising an adjuvant.

11. A method of preventing or ameliorating respiratory disease comprising administering to a subject ruminant an effective amount of a vaccine composition according to claim 8.

12. The vaccine composition of claim 8, wherein said chimeric protein comprises the LKT-γIFN amino acid sequence of SEQ ID NO:4.

13. A method of preventing or ameliorating respiratory disease comprising administering to a subject ruminant an effective amount of a vaccine composition according to claim 12.

* * * * *